(12) United States Patent
Powers et al.

(10) Patent No.: US 7,482,379 B2
(45) Date of Patent: Jan. 27, 2009

(54) PROPENOYL HYDRAZIDES

(75) Inventors: James C. Powers, Atlanta, GA (US);
Juliana Asgian, Fullerton, CA (US);
Özlem Dogan Ekici, Columbus, OH (US); Marion Gabriele Gotz, Hirschau (DE); Karen Ellis James, Cumming, GA (US); Zhao Zhao Li, Norcross, GA (US); Brian Rukamp, Greenleaf, WI (US)

(73) Assignee: Georgia Tech Research Corporation, Atlanta, GA (US)

( * ) Notice: Subject to any disclaimer, the term of this patent is extended or adjusted under 35 U.S.C. 154(b) by 601 days.

(21) Appl. No.: 11/062,017

(22) Filed: Feb. 18, 2005

(65) Prior Publication Data

US 2005/0256058 A1    Nov. 17, 2005

Related U.S. Application Data

(60) Provisional application No. 60/545,354, filed on Feb. 18, 2004.

(51) Int. Cl.
*A61K 31/15* (2006.01)
*C07C 243/10* (2006.01)

(52) U.S. Cl. ..................................... 514/614; 564/151

(58) Field of Classification Search ....................... None
See application file for complete search history.

(56) References Cited

U.S. PATENT DOCUMENTS

| 4,596,822 | A | 6/1986 | Powers et al. |
|---|---|---|---|
| 5,109,018 | A | 4/1992 | Powers et al. |
| 5,281,721 | A | 1/1994 | Powers et al. |
| 5,554,767 | A | 9/1996 | Wang et al. |
| 5,760,048 | A | 6/1998 | Wang et al. |
| 6,376,468 | B1 | 4/2002 | Overkleeft et al. |
| 6,387,908 | B1 | 5/2002 | Nomura et al. |
| 6,479,676 | B1 | 11/2002 | Wolf |
| 2004/0048327 | A1 | 3/2004 | Powers et al. |
| 2004/0127427 | A1 | 7/2004 | Powers et al. |

OTHER PUBLICATIONS

Aza-Peptide Michael Acceptors: A New Class of Inhibitors Specific for Caspases and Other Clan CD Cysteine Proteases, Ozlem Dogan Ekici, et al.; J. Med. Chem. 2004, 47, pp. 1889-1892.

*Primary Examiner*—Zinna N Davis
(74) *Attorney, Agent, or Firm*—Thomas, Kayden, Horstemeyer & Risley, LLP; Todd Deveau

(57) ABSTRACT

The present disclosure provides compositions for inhibiting proteases, methods for synthesizing the compositions, and methods of using the disclosed protease inhibitors. Aspects of the disclosure include a peptidyl propenoyl hydrazide compositions that inhibit proteases, for example cysteine proteases, either in vivo or in vitro.

9 Claims, 1 Drawing Sheet

PROPENOYL HYDRAZIDES

CROSS-REFERENCE TO RELATED APPLICATION

Figure 1:
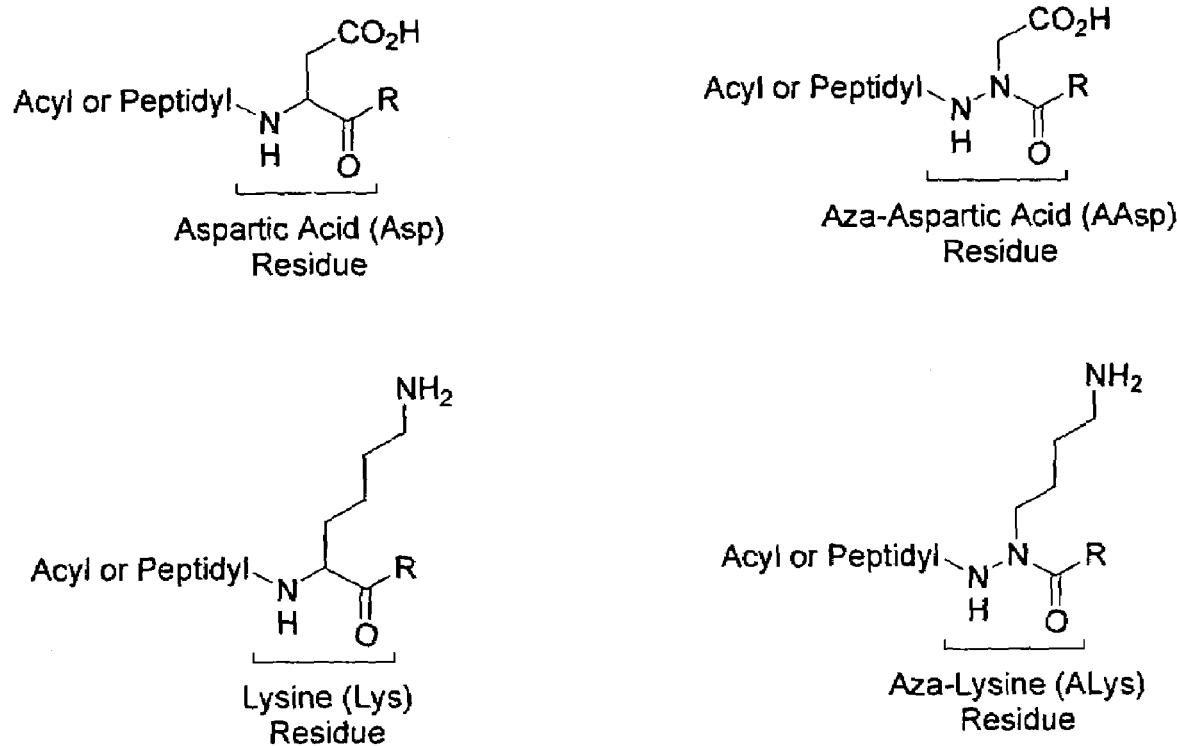

This application claims benefit of and priority to U.S. Provisional Patent Application No. 60/545,354 filed on Feb. 18, 2004, and which is incorporated by reference in its entirety where permissible.

STATEMENT REGARDING FEDERALLY SPONSORED RESEARCH OR DEVELOPMENT

Aspects of the work disclosed herein were support in part by the National Institutes of Health. Therefore, the U.S. government may have rights in the claimed subject matter.

BACKGROUND

1. Technical Field

This disclosure relates generally to protease inhibitors and applications thereof, more specifically to peptide inhibitors of cysteine proteases, even more specifically to propenoyl hydrazides, methods of their use, and methods of their production.

2. Related Art

Protease inhibitors are important therapeutics in the treatment of a variety of disease conditions including viral infections such as HIV infection. Proteases are enzymes that cleave proteins or peptides and are classified into several groups. For example, cysteine proteases form a group of enzymes involved in numerous disease states, and inhibitors of these enzymes can be used therapeutically for the treatment of diseases involving cysteine proteases.

Cysteine Proteases.

Cysteine proteases employ a thiolate residue, which performs a nucleophilic attack on the amide bond of the peptide backbone to form a tetrahedral intermediate. The intermediate collapses to release the first product and the resulting acyl enzyme then undergoes hydrolysis. Based on their sequence homology cysteine proteases are divided into several clans and families. Clan CA and clan CD contain the majority of cysteine proteases. The majority of cysteine proteases, such as papain, calpains, cathepsins, and cruzain belong to the clan CA. According to the crystal structure of papain, clan CA proteases are unique for their catalytic triad formed by Cys, His, and Asn. The oxyanion hole is created by a preceding Gln residue. Clan CA enzymes are inhibited by E-64, a natural inhibitor of cysteine proteases, and cystatin. The substrate specificity of clan CA enzymes is primarily controlled by the S2 enzyme subsite. Clan CD enzymes are unique for their lack of inhibition by E-64 and their specificity for the P1 amino acid residue. Even though clan CD is the smallest of the clans, it contains some very important enzymes. Among them are caspases, legumains, gingipains, clostripain, and separase.

Caspases are a recently discovered family of cysteine endoproteases, which are highly selective for Asp at the P1 residue. As a result, this newly emerging family of proteases has been called caspases (cysteinyl aspartate—specific protease). All caspases contain the conserved pentapeptide active site motif Gln-Ala-Cys-X-Gly (QACXG)(SEQ. ID NO. 1), where X=Arg, Gln, Gly (R, Q, G), and are synthesized as inactive proenzymes. The only other mammalian protease with specificity for Asp is the lymphocyte serine protease, granzyme B. Many of the proteolytic cleavages that are observed during apoptosis and cytokine maturation are due to the action of various caspases. Indeed, many of the procaspases are activated by other caspases, which selectively cleave at P1 Asp residues in their recognition sites.

At present, there are 11 homologous members of the caspase family in humans. Some caspases are important mediators of inflammation, where they are involved in the production of inflammatory cytokines, and others are involved in apoptosis, where they participate in signaling and effector pathways. Group I caspases (caspases-1,-4, -5, -11, -12, -13, and -14) are primarily mediators of inflammation and are involved in proteolytic activation of proinflammatory cytokines. Caspase-1 is also involved in the Fas and TNFR apoptotic pathway. Group II caspases (caspases-2, -3, and -7) are late phase effectors of apoptosis and are involved in the cleavage of key structural and homeostatic proteins. Caspase-3, also known as CPP32 (cysteine protease protein 32-kDa), Yama or apopain, is believed to be one of the major effectors in apoptosis. This enzyme is a key executioner because it is responsible either partially or totally for proteolytic cleavage of key apoptotic proteins. It functions to decrease or destroy essential homeostatic pathways during the effector phase of apoptosis. Caspase-3 cleaves or activates nuclear enzymes, such as poly(ADP-ribose)polymerase (PARP), the 70 kDa subunit of the U1 small ribonucleoprotein, the catalytic subunit of DNA-dependent protein kinase, and protein kinase Cδ. Group III caspases (caspases-6, -8, -9, -10) are involved in the upstream early activation of effector caspases. Studies have shown that caspase-8 and -10 can cleave radiolabeled precursors for caspase-3. Caspase-6 is the only known caspase that cleaves the lamins, the major structural proteins in the nuclear envelope. Proteolysis of lamins is observed in cells undergoing apoptosis. Caspase-8 (MACH/FLICE), which can cleave all other known caspases, is suggested to lie in the pinnacle of the apoptotic cascade, at least when apoptosis is initiated by some stimuli such as Fas-L and TNF. Accordingly, the present disclosure encompasses compositions and methods of altering, inhibiting, or reducing the formation of enzymatic reaction products involving cysteine proteases. Inhibiting the formation of cysteine protease reaction products in vivo can provide therapeutic effects to patients suffering from unregulated or undesired protease activity.

Caspases have a specificity for at least four amino acids to the left of the cleavage site (P side). The S4 subsite is the single most important determinant of specificity among caspases after the P1 Asp. The optimal sequences of the caspases were obtained using a positional-scanning combinatorial substrate library (PS-CSL). The optimal recognition sequences for these enzymes are closely related to the sequences found in known macromolecular substrates. Group I caspases' optimal sequence is Trp-Glu-His-Asp (WEHD) (SEQ. ID NO. 2) with S4 favoring hydrophobic amino acids. Group II caspases' optimal sequence is Asp-Glu-X-Asp (DEXD) (SEQ. ID NO. 3) with a requirement for Asp in S4. Group III caspases' optimal sequence is N-Glu-X-Asp where N=Val or Leu, and X can be any amino acid ((V,L)EXD) (SEQ. ID NO. 4) with a preference for branched, aliphatic side chains in S4. The S3 subsite prefers glutamic acid (E) in most of the caspases, which could be explained by the salt link between Arg-341 (involved in stabilization of the P1 aspartic acid) and the glutamic acid in P3.

Legumains (EC.3.4.22.34, asparaginyl endopeptidase) form a another important family (C13) of clan CD proteases. They are related to caspases and other clan CD enzymes by a shared catalytic-site motif and a common scaffold within their catalytic domains. They were first identified in leguminous plants, and later in mammalian cells. In mammalian cells legumain has been linked to osteoclast formation and bone resorption, and the processing of bacterial antigens and the potential autoantigen, myelin basic protein, in the major histocompatability (MHC) class II system. In *S. mansoni* the legumain protease (SmAE, Sm32) is dissimilar to the other proteinases and may process gut-associated clan CA zymogens to their active forms, thus facilitating the digestion of ingested host serum proteins. *S. mansoni* legumain is not inhibited by the clan CA cysteine protease inhibitor E-64 or the diazomethane inhibitor Cbz-Phe-Ala-CHN$_2$. Irreversible protease inhibitors would have great potential for the short-term therapeutic administration against parasitic infections. So far there has been no success in the determination of a crystal structure of the asparaginyl endopeptidase. Like all clan CD proteases, the substrate specificity of legumain is controlled by the interactions of the S1 subsite. Legumains selectively hydrolyze substrates with an asparaginyl residue in the P1 position. Legumain is less selective with respect to the P2 and P3 positions, but prefers Ala or Thr. The synthetic substrate Cbz-Ala-Ala-Asn-AMC was effectively cleaved by *S. mansoni* legumain and human legumain with $K_M$'s of 90 and 80 µM respectively.

Next to caspases and legumains, the family of separases has gained increasing attention among the clan CD enzymes. Separases play an important role during mitosis at the metaphase to anaphase transition. When the sister chromatids are aligned at the onset of the anaphase, separase initiates the segregation of the chromosomes by facilitating the breakdown of a cohesion complex between the individual sister chromatides.

Neural tissues, including brain, are known to possess a large variety of proteases, including at least two calcium-stimulated proteases termed calpains. Calpains are present in many tissues in addition to the brain. Calpain I is activated by micromolar concentrations of calcium while calpain II is activated by millimolar concentrations. In the brain, calpain II is the predominant form, but calpain I is found at synaptic endings and is thought to be the form involved in long term potentiation, synaptic plasticity, and cell death. Other Ca$^{2+}$ activated cysteine proteases may exist, and the term "calpain" is used to refer to all Ca$^{2+}$ activated cysteine proteases, including calpain I and calpain II. The terms "calpain I" and "calpain II" are used herein to refer to the micromolar and millimolar activated calpains, respectively, as described above. While calpains degrade a wide variety of protein substrates, cytoskeletal proteins seem to be particularly susceptible to attack. In some cases, the products of the proteolytic digestion of these proteins by calpain are distinctive and persistent over time. Since cytoskeletal proteins are major components of certain types of cells, this provides a simple method of detecting calpain activity in cells and tissues. Activation of calpains and/or accumulation of breakdown products of cytoskeletal elements have been observed in neural tissues of mammals exposed to a wide variety of neurodegenerative diseases and conditions. For example, these phenomena have been observed following ischemia in gerbils and rats, following stroke in humans, following administration of the toxins kainate, trimethyltin, or colchicine in rats, and in human Alzheimer's disease.

Cathepsin B is involved in muscular dystrophy, myocardial tissue damage, tumor metastasis, and bone resorption. In addition, a number of viral processing enzymes, which are essential for viral infection, are cysteine proteases. Inhibitors of cysteine proteases would have multiple therapeutic uses.

Other important cysteine proteases are the bacterial enzymes clostripain and gingipain. Gingipain causes tissue destruction during periodontal diseases.

Cysteine Protease Inhibitors.

To date, a structurally diverse variety of cysteine protease inhibitors have been identified. Palmer, (1995) J. Med. Chem., 38, 3193, discloses certain vinyl sulfones, which act as cysteine protease inhibitors for cathepsins B, L, S, O2 and cruzain. Other classes of compounds, such as aldehydes, niitriles, α-ketocarbonyl compounds, halomethyl ketones, diazomethyl ketones, (acyloxy)methyl ketones, ketomethylsulfonium salts and epoxy succinyl compounds have also been reported to inhibit cysteine proteases. See Palmer, id, and references cited therein. Many irreversible cysteine protease inhibitors have been described in the review by Powers, Asgian, Ekici, and James (2002) Chemical Reviews, 102, 4639. See Powers, id, and references cited therein. However, most of these known inhibitors are not considered suitable for use as therapeutic agents in animals, especially humans, because they suffer from various shortcomings. These shortcomings include lack of selectivity, cytotoxicity, poor solubility, and overly rapid plasma clearance.

Several types of Michael acceptor warheads have been employed as inhibitors for cysteine proteases. Among the most effective inhibitors are vinyl sulfones and α,β-unsaturated carbonyl derivatives against various cysteine proteases. Hanzlik, (1984) J. Med. Chem., 27, 711 has replaced the carbonyl group of a good substrate with a moiety, that would trap the enzymatic nucleophile (Ser-OH or Cys-OH) without altering the structural features required for enzyme recognition and binding. The fumarate derivative of the epoxy succinate E-64c, which is one of the first Michael acceptor inhibitors reported, extends the α,β-unsaturated carbonyl by an additional carbonyl for possible structural recognition and binding requirements within the enzyme active site. The fumarate derivative of E-64c (trans-HOOCCH═CH—CO-Leu-NH(CH$_2$)$_2$CH(CH$_3$)$_2$) inhibits cathepsin B ($k_{app}$=625 M$^{-1}$s$^{-1}$), cathepsin H ($k_{app}$=M$^{-1}$s$^{-1}$), and cathepsin L ($k_{app}$=2272 M$^{-1}$s$^{-1}$) irreversibly. Both the fumarate analog of E-64c and the epoxide parent compound do not inhibit clan CD proteases. Caspases, legumains, gingipains and clostripain are members of clan CD, while papain, cathepsins, and calpains are members of clan CA. Therefore, because of the aforementioned deficiencies in the art, there is a need for new compounds and methods for inhibiting proteases, in particular cysteine proteases.

SUMMARY

Aspects of the present disclosure provide compositions for inhibiting proteases, methods for synthesizing the compositions, and methods of using the disclosed protease inhibitors. One aspect provides a hydrazide comprising an aza-amino acid residue in a P1 site. The compositions described herein can inhibit proteases, for example cysteine proteases, either in vivo or in vitro, by contacting a cysteine protease with a propenoyl hydrazide, which acts as a Michael acceptor. The disclosed compounds, pharmaceutically acceptable salts, pharmaceutically acceptable derivatives, prodrugs, or combinations thereof can be used to treat disease or pathological conditions related to the activity of proteases associated with a specific disease or condition. Such treatable conditions include viral infections, stroke, neurodegenerative disease, and inflammatory disease, among others. Methods disclosed herein for treating diseases include administering an effective amount of a propenoyl hydrazide to a host in need thereof to inhibit or reduce protease activity in the host, particularly cysteine protease activity, more particularly activity of caspases, calpains, cathepsins, papain, gingipain, clostripain, separin, or legumain. One or more propenoyl hydrazides of the present disclosure can also be used alone or in combination with each other, other protease inhibitors, or another therapeutic agent including anti-viral compounds such as anti-viral nucleosides including nucleoside analogs.

One aspect of the disclosure provides propenoyl hydrazide compositions, for example a compound or pharmaceutically acceptable salt or pharmaceutically acceptable derivative thereof according to Formula I below. In some aspects of the present disclosure, propenoyl hydrazide inhibitors are specific for cysteine proteases and do not inhibit serine proteases or aspartyl proteases. In another aspect of the present disclosure, these propenoyl hydrazide compounds potently and specifically inhibit clan CD cysteine proteases. Although the compounds of the present disclosure are usually specific for cysteine proteases of clan CD, they are also inhibitors of other proteases. Exemplary differences between propenoyl hydrazides disclosed herein and other cysteine protease inhibitors include different mechanisms of inhibition of the cysteine residue and the binding modes.

Some propenoyl hydrazides of the present disclosure can be constructed to selectively inhibit individual cysteine proteases or groups of cysteine proteases. These propenoyl hydrazides can, for example, contain acidic aza-amino acid residues in the P1 site. Such propenoyl hydrazides are potent inhibitors of caspases. Propenoyl hydrazide caspase inhibitors are useful for the treatment of stroke and inflammatory diseases, and as inhibitors of apoptosis. Thus, another aspect provides a method of treating stroke, inflammatory disease, or inhibiting apoptosis including administering an effective amount of a propenoyl hydrazide to a patient in need thereof. Such patients can include any mammal, for example a mammal exhibiting symptoms characteristic of a protease related pathology or disease condition such as stroke, inflammatory disease, or pathology related to apoptosis.

Another aspect of the present disclosure provides a propenoyl hydrazide composition containing an aza-asparagine residue at the P1 position. Propenoyl hydrazides having an aza-asparagine residue at the P1 position inhibit legumain and can, therefore, modulate the immune system through such inhibition. Cleavage of antigens by proteases such as legumain and related proteases is a step in antigen presentation including the display of MHC class II peptides. Thus, another aspect of the disclosure provides a method of modulating the immune system of a patient by administering to a host an effective amount of a propenoyl hydrazide composition. The propenoyl hydrazide can modulate the immune system by inhibiting the cleavage of antigens in the patient and thereby reducing the display of antigen peptides on cell surfaces.

Yet another aspect of the disclosure provides a method of treating autoimmune disease by administering an effective amount of a propenoyl hydrazide to a host in need thereof. The host can be any mammal, including primates, which demonstrates symptoms associated with any number of autoimmune diseases including but not limited to lupus, for example lupus erythematosus, and cancers.

Another aspect of the disclosure provides propenoyl hydrazides containing basic residues at the P1 position. Such propenoyl hydrazides inhibit proteases such as gingipain, separase, and clostripain. Propenoyl hydrazide inhibitors of gingipain can be used for treatment of periodontal diseases. Propenoyl hydrazide inhibitors of separase are useful for stopping, modulating, or interfering with cell division.

In another aspect, this disclosure provides a method to identify proteolytic enzymes and a method to prevent proteolysis.

BREIF DESCRIPTION OF THE DRAWINGS

FIG. 1 shows two exemplary aza-amino acids.

DETAILED DESCRIPTION

The present disclosure may be understood more readily by reference to the following detailed description of the disclosure and the Examples included therein.

Before the present compounds, compositions and methods are disclosed and described, it is to be understood that this disclosure is not limited to specific synthetic methods, specific pharmaceutical carriers, or to particular pharmaceutical formulations or administration regimens, as such may, of course, vary. It is also to be understood that the terminology used herein is for the purpose of describing particular embodiments only and is not intended to be limiting.

Cysteine Proteases.

One embodiment provides propenoyl hydrazide compositions that inhibit enzymatic cleavage of proteins or peptides, or a combination thereof. Exemplary enzymes inhibited by propenoyl hydrazides include cysteine proteases, for example, caspases, legumains, gingipains, clostripain, and separase.

The present disclosure includes all hydrates, solvates, complexes and prodrugs of the compounds of this disclosure. The term prodrug refers to a pharmacologically inactive compound that is converted to an active drug by a metabolic biotransformation. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of Formula I. Additional types of prodrugs are also encompassed. For instance, free carboxyl groups can be derivatized as amides or alkyl esters. The amide and ester moieties may incorporate groups including but not limited to ether, amine and carboxylic acid functionalities. Free hydroxy groups may be derivatized using groups including but not limited to hemisuccinates, phosphate esters, dimethylaminoacetates, and phosphoryloxymethyloxycarbonyls, as outlined in D. Fleisher, R. Bong, B. H. Stewart, Advanced Drug Delivery Reviews (1996) 19, 115. Carbamate prodrugs of hydroxy and amino groups are also included, as are carbonate prodrugs and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in R. P. Robinson et al., J. Medicinal Chemistry (1996) 39, 10.

The subject disclosure also includes isotopically-labelled compounds, and the pharmaceutically acceptable salts thereof, which are identical to those recited in Formula I, but for the fact that one or more atoms are replaced by an atom having an atomic mass or mass number different from the atomic mass or mass number usually found in nature. Examples of isotopes that can be incorporated into compounds of the disclosure include isotopes of hydrogen, carbon, nitrogen, oxygen, phosphorous, fluorine and chlorine. Compounds of the present disclosure, prodrugs thereof, and pharmaceutically acceptable salts of said compounds or of said prodrugs which contain the aforementioned isotopes and/or other isotopes of other atoms are within the scope of this disclosure. Certain isotopically-labelled compounds of the present disclosure, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of Formula I of this disclosure and prodrugs thereof can generally be prepared by carrying out the procedures disclosed in the Schemes and/or in the Examples and Preparations below, by substituting a readily available isotopically labeled reagent for a non-isotopically labeled reagent.

If a chiral center or another form of an isomeric center is present in a compound of the present disclosure, all forms of such isomer or isomers, including enantiomers and diastereomers, are intended to be covered herein. Inventive compounds containing a chiral center may be used as a racemic mixture, an enantiomerically enriched mixture, or the racemic mixture may be separated using well-known techniques and an individual enantiomer may be used alone. An enantiomerically enriched mixture means a mixture having greater than about 50% of a single enantiomer. In cases in which compounds have unsaturated carbon-carbon double bonds, both the cis (Z) and trans (E) isomers are within the scope of this disclosure. The compositions of the present disclosure can be substantially optically pure. Substantially optically pure means a composition having greater than 90%, preferably greater than 95%, most preferably greater than 98% of a single optical isomer.

It must be noted that, as used in the specification and the appended claims, the singular forms "a," "an" and "the" include plural referents unless the context clearly dictates otherwise. Thus, for example, reference to "an aromatic compound" includes mixtures of aromatic compounds, reference to "a pharmaceutical carrier" includes mixtures of two or more such carriers, and the like.

Nomenclature.

In discussing the interactions of peptides with cysteine proteases, we have utilized the nomenclature of Schechter and Berger [*Biochem. Biophys. Res. Commun.* 27, 157-162 (1967); incorporated herein by reference]. The individual amino acid residues of a substrate or inhibitor are designated P1, P2, etc. and the corresponding subsites of the enzyme are designated S1, S2, etc. The scissile bond of the substrate is S1 -S1'. The most important recognition subsites of scysteine proteases are S1 and S2.

Amino acid residues and blocking groups are designated using standard abbreviations [see J. Biol. Chem. 260, 14-42 (1985) for nomenclature rules; incorporated herein by reference]. An amino acid residue (AA) in a peptide or inhibitor structure refers to the part structure —NH—CHR$_1$—CO—, where R$_1$ is the side chain of the amino acid residue AA. It will be appreciated that at least one of the amino acid residues of the propenoyl hydrazides of the disclosure may be substituted by one of the well known non-naturally occurring amino acid residues. Alterations such as these may serve to increase the stability, bioavailability and/or inhibitory action of the peptides of the disclosure. Moreover, any of the propenoyl hydrazides described herein may, additionally, have a non-peptide macromolecular carrier group covalently attached to their amino and/or carboxy termini. Such macromolecular carrier groups may include, for example, lipid-fatty acid conjugates, polyethylene glycol, or carbohydrates. The term MeAA describes an N-methylated amino acid, as for example MePhe, which is phenylalanine, where the nitrogen is substituted with a methyl group.

FIG. 1 shows two examples of aza-amino acids. An aza-amino acid residue (structures top and bottom right) is an alpha-amino acid residue (structures top and bottom left) where the alpha-carbon has been replaced by a nitrogen atom. It will be abbreviated as the three letter code for the amino acid preceded by an "A". Therefore, substituting the α-carbon of an aspartate residue with a nitrogen converts an aspartic acid residue (Asp) to an aza-aspartic acid, which will be abbreviated as AAsp, and a lysine residue (Lys) to aza-lysine (ALys).

Another embodiment provides a propenoyl hydrazide having the following formula

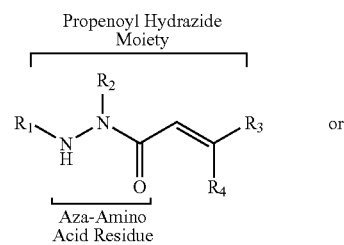

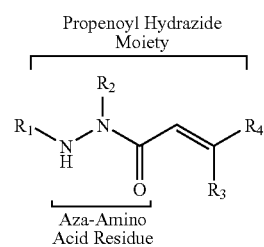

The R$_3$ or R$_4$ group would be abbreviated as CO$_2$H, CO$_2$Et, CO$_2$R, CONHR, CONRR', or CO-AA-T if the propenoyl hydrazide contains a fumarate moiety in its structure. Otherwise, the structure of the R$_3$ or R$_4$ group would be drawn or abbreviated.

Another embodiment provides propenoyl hydrazides having abbreviated structures according to the following:
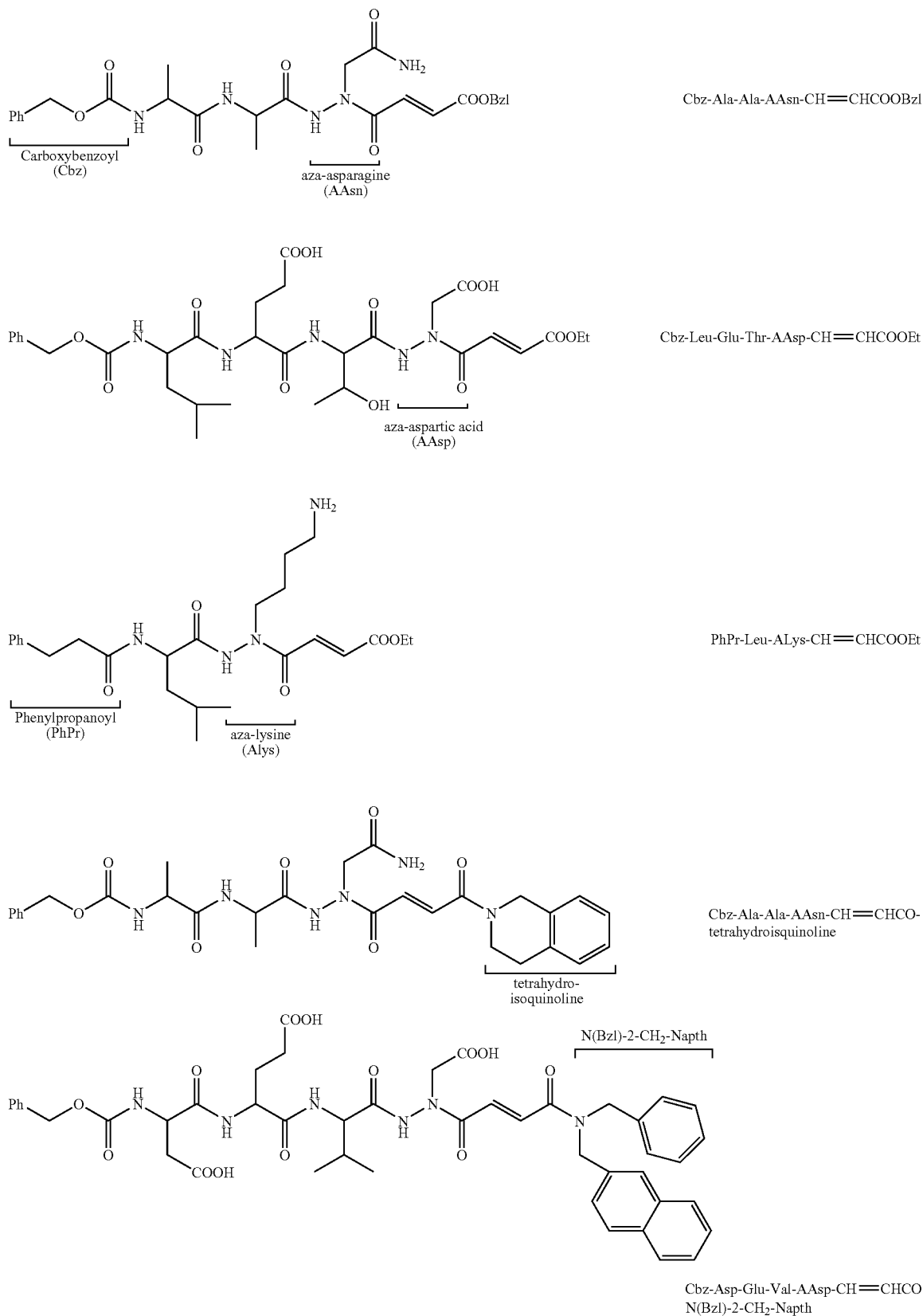

There can be three structural isomers at the double bond moiety, if the appropriate substituents are present, two trans isomers (E and Z) and one cis isomer. The cis and trans nomenclature is used for simple alkenes with similar substituents. A C=C double bond is referred to as cis, when the substituents are on the same side of the double bond, and trans, when the substituents are on opposite sides. The E and Z terminology applies to compounds that contain a C=C double bond with more than two substituents. The Cahn-Prelog-Ingold selection rules are used to assign priorities to the various substituents. If the two substituents with the highest priority are on the same side, the double bond is given the designation Z (from zusammen) and E (from entgegen), if they are on opposite sides.

Exemplary isomers according to one embodiment of the present disclosure have the following structural formulae:

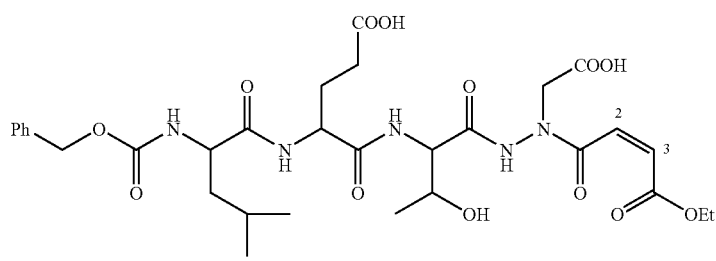

Cbz-Leu-Glu-Thr-AAsp-cis-CH=CHCOOEt
(This is the cis or Z isomer)

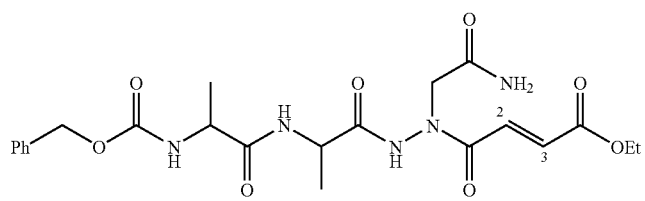

Cbz-Ala-Ala-AAsn-trans-CH=CHCOOEt
(This is the trans or E isomer)

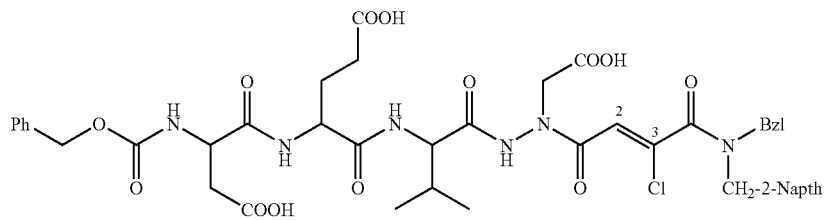

(Z)-Cbz-Asp-Glu-Val-AAsp-CH=C(Cl)CON(Bzl)-2-CH-Napth
(This is the Z isomer)

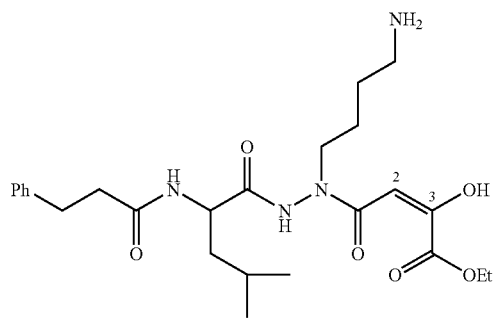

(E)-PhPr-Leu-ALys-CH=C(OH)COOEt
(This is the E isomer)

The numbering of the carbons of the double bond is shown above.

The term "amino," as used herein, refers to —NH$_2$ or derivatives thereof formed by independent replacement of one or both hydrogen atoms thereon with a substituent or substituents independently selected from alkyl, alkanoyl, aryl, arylalkyl, cycloalkyl, cycloalkylalkyl, heteroaryl, heteroarylalkyl, and an amino protecting group.

The term "$C_{1-10}$ acyl," as used herein, refers to a $C_{1-10}$ alkyl group, as defined herein, having an attached carbonyl group.

The term "$C_{1-10}$ alkoxy," as used herein, refers to a $C_{1-10}$ alkyl group, as defined herein, attached to the parent molecular group through an oxygen atom.

The term "$C_{1-10}$ alkyl" as used herein refers to a branched or unbranched hydrocarbon group of carbon atoms, such as methyl, ethyl, n-propyl, isopropyl, n-butyl, isobutyl, 1-butyl, and the like or branched or unbranched hydrocarbon groups of carbon atoms that either contain double or triple carbon bonds.

The term "$C_{1-10}$ alkylamino," as used herein, refers to a $C_{1-10}$ alkyl group, as defined herein, to which is attached at least one amino substituent.

The term "$C_{3-15}$ cycloalkyl" as applied herein is meant to include cyclic hydrocarbon chains. Examples of these cyclic hydrocarbon chains include cyclopropane, cyclobutane, cyclopentane, cyclohexane, cycloheptane, cyclooctane, cyclononane, cyclodecane, cycloundecane, etc.

The term "$C_{2-12}$ dialkylamino," as used herein refers to two $C_{1-10}$ alkyl groups, as defined herein, that are attached to an amino substituent.

The term "$C_{1-10}$ fluoroalkyl," as used herein, refers to a $C_{1-10}$ alkyl group, as defined herein, to which is attached at least one fluorine substituent.

The term "$C_{1-10}$ perfluoroalkyl," as used herein, refers to a $C_{1-10}$ alkyl group in which all of the hydrogen atoms have been replaced with fluorine atoms.

The term biotinyl, as use herein, refers to biotin without the biotin carboxyl hydroxyl group.

By the term "effective amount" of a compound as provided herein is meant a nontoxic but sufficient amount of the compound to provide the desired utility. As will be pointed out below, the exact amount required will vary from subject to subject, depending on the species, age, and general condition of the subject, the severity of the condition or disease that is being treated, the particular compound used, its mode of administration, and the like. Thus, it is not possible to specify an exact "effective amount." However, an appropriate effective amount may be determined by one of ordinary skill in the art using only routine experimentation.

The term "pharmaceutically acceptable salt(s)", as used herein, unless otherwise indicated, includes salts of acidic or basic groups which may be present in the compounds of Formula I. The compounds of Formula I that are basic in nature are capable of forming a wide variety of salts with various inorganic and organic acids. The acids that may be used to prepare pharmaceutically acceptable acid addition salts of such basic compounds of Formula I are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, TFA, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. Those compounds of the Formula I that are acidic in nature, are capable of forming base salts with various pharmacologically acceptable cations. Examples of such salts include the alkali metal or alkaline earth metal salts and particularly, the sodium and potassium salts.

The term "pharmaceutically acceptable derivative" refers to any homolog, analog, or fragment corresponding to the propenoyl hydrazides of the present disclosure provided herein which inhibits protease activity and is relatively non-toxic to the subject or host.

The term "pharmaceutically acceptable" means a material that is not biologically or otherwise undesirable, i.e., the material may be administered to an individual along with the selected propenoyl hydrazide without causing any undesirable biological effects or interacting in a deleterious manner with any of the other components of the pharmaceutical composition in which it is contained.

As used herein, and without limitation, the term "derivative" is used to refer to any compound which has a structure derived from the structure of the compounds of the present disclosure and whose structure is sufficiently similar to those disclosed herein and based upon that similarity, would be expected, by one skilled in the art, to exhibit the same or similar activities and utilities as the claimed compounds.

The following abbreviations have also been used: AFC, 7-amino-4-trifluoromethylcoumarin; AAsp, aza-aspartic acid residue; AAsn, aza-asparagine; ALeu, aza-leucine; ALys, aza-lysine residue; AHph, aza-homophenylalanine residue; AOrn, aza-omithine; AMC, 7-amino-4-methylcoumarin; Boc, tert-butoxycarbonyl; Brij, polyoxyethylenelaurylether; Bzl, benzyl; CHAPS, 3-[(3-cholamidopropyl)dimethylarmnonio]-1-propanesulfonate; Cbz, Ph-CH$_2$OCO—; DCC, 1,3-dicyclohexylcarbodiimide; DMAP, 4-dimethylaminopyridine; DMF, N,N-dimethylformamide; DMSO, dimethylsulfoxide; DTT, dithiothreitol; EDC, 1-(3-dimethylaminopropyl)-3-ethylcarbodiimide hydrochloride; EtOAc, ethyl acetate; HEPES, N-2-hydroxyethylpiperazine-N'-2-ethanesulfonic acid HOBt, 1-hydroxybenzotriazole; HRMS, high resolution mass spectrometry; iBCF, isobutyl chloroformate; IBX, iodooxybenzoic acid; IC, inhibitory concentration; 2-Napth, 2-naphthyl; NMM, 4-methylmorpholine; Np2, 2-naphthylalanyl; PhPr, Phenylpropyl; Pyr, pyridine, TFA, trifluoroacetic acid; THF, tetrahydrofuran; TLC, thin layer chromatography.

One embodiment of the present disclosure provides propenoyl hydrazides having the following structural Formula I:

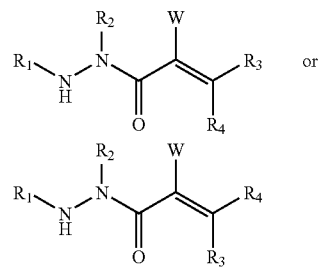

wherein, $R_1$ is selected from the group consisting of $M_1$-$AA_1$, $M_1$-$AA_2$-$AA_1$, and $M_1$-$AA_3$-$AA_2$-$AA_1$;

W is selected from the group consisting of halogen, cyano, and hydrogen;

$M_1$ is selected from the group consisting of H, NH$_2$—CO—, NH$_2$—CS—, NH$_2$—SO$_2$—, X—NH—CO—, X$_2$N—

CO—, X—NH—CS—, X₂N—CS—, X—NH—SO₂—, X₂N—SO₂—, X—CO—, X—CS—, X—, Y—SO₂—, Y—O—CO—, Y—O—CS—, morpholine-CO—, and biotinyl;

X is selected from the group consisting of H, $C_{1-10}$ alkyl, $C_{3-15}$ cyclized alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, pentafluorophenyl, phenyl monosubstituted with K, phenyl disubstituted with K, phenyl trisubstituted with K, naphthyl, naphthyl monosubstituted with K, naphthyl disubstituted with K, naphthyl trisubstituted with K, $C_{1-10}$ fluoroalkyl with an attached phenyl group, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached naphthyl group, $C_{1-10}$ alkyl with an attached naphthyl group substituted with K, $C_{1-10}$ alkyl with an attached phenoxy group, and $C_{1-10}$ alkyl with an attached phenoxy group substituted with K on the phenoxy group;

Y is selected from the group consisting of $C_{1-10}$ alkyl, $C_{3-15}$ cyclized alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl monosubstituted with K, phenyl disubstituted with K, phenyl trisubstituted with K, naphthyl, naphthyl monosubstituted with K, naphthyl disubstituted with K, naphthyl trisubstituted with K, $C_{1-10}$ fluoroalkyl with an attached phenyl group, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached naphthyl group, $C_{1-10}$ alkyl with an attached naphthyl group substituted with K, $C_{1-10}$ alkyl with an attached phenoxy group, and $C_{1-10}$ alkyl with an attached phenoxy group substituted with K on the phenoxy group;

J is selected from the group consisting of halogen, $CO_2H$, OH, CN, $NO_2$, amino, $C_{1-10}$ alkoxy, $C_{1-10}$ alkylamino, $C_{2-12}$ dialkylamino, $C_{1-10}$ alkyl-O—CO—, $C_{1-10}$ alkyl-O—CO—NH—, and $C_{1-10}$ alkyl-S—;

K is selected from the group consisting of halogen, $C_{1-10}$ alkyl, $C_{1-10}$ perfluoroalkyl, $C_{1-10}$ alkoxy, phenoxy, $NO_2$, CN, OH, $CO_2H$, $CONH_2$, amino, $C_{1-10}$ alkylamino, $C_{2-12}$ dialkylamino, $C_{1-10}$ acyl, and $C_{1-10}$ alkoxy-CO—, and $C_{1-10}$ alkyl-S—;

$AA_1$, $AA_2$, and $AA_3$ are side chain blocked or unblocked amino acids with the L configuration, D configuration, or no chirality at the alpha-carbon selected from the group consisting of alanine, valine, leucine, isoleucine, proline, methionine, methionine sulfoxide, phenylalanine, tryptophan, glycine, serine, threonine, cysteine, tyrosine, asparagine, glutanine, aspartic acid, glutamic acid, lysine, arginine, histidine, phenylglycineQ beta-alanine, norleucine, norvaline, alpha-aminobutanoic acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$-CH($CH_2CHEt_2$)-$CO_2H$, alpha-aminoheptanoic acid, $NH_2$—CH($CH_2$-1-naphthyl)-$CO_2H$, $NH_2$-CH($CH_2$-2-naphthyl)-$CO_2H$, $NH_2$—CH($CH_2CH_2CH_2$-phenyl)-$CO_2H$, $NH_2$—CH($CH_2$-cyclohexyl)-$CO_2H$, $NH_2$—CH($CH_2$-cyclopentyl)-$CO_2H$, $NH_2$—CH($CH_2$-cyclobutyl)-$CO_2H$, $NH_2$—CH($CH_2$-cyclopropyl)-$CO_2H$, trifluoroleucine, 4-fluorophenylalanine, lysine substituted on the epsilon nitrogen with a biotinyl group, hexafluoroleucine,

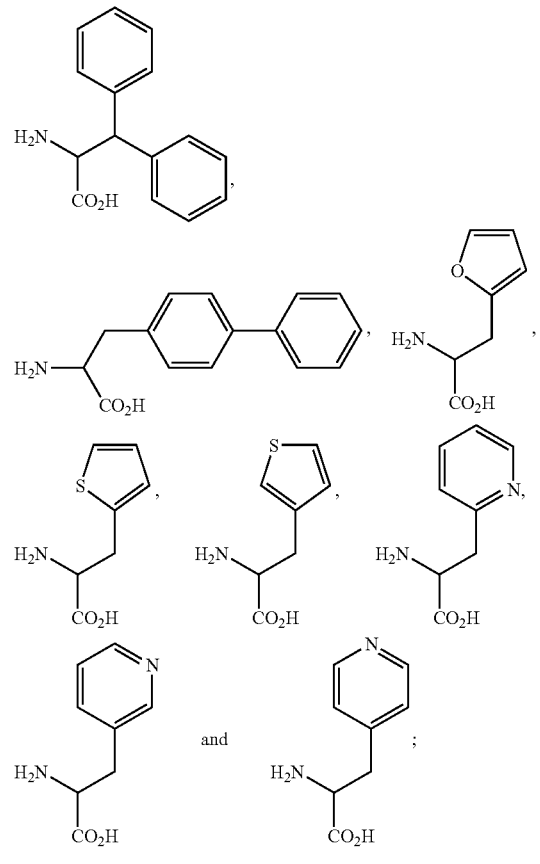

$R_2$ is selected from the group consisting of $C_{1-10}$ alkyl, $C_{1-10}$ perfluoroalkyl, $C_{1-10}$ alkyl substituted with Q, $C_{1-10}$ alkyl substituted with phenyl, $C_{1-10}$ alkyl with an attached phenyl substituted with K, $C_{1-10}$ alkyl substituted with naphthyl, $C_{1-10}$ alkyl with an attached naphthyl substituted with K, phenyl, phenyl substituted with K, naphthyl, naphthyl substituted with K, $C_{1-10}$ alkyl substituted with $CONH_2$, $C_{1-10}$ alkyl substituted with $CONHR_5$, $C_{1-10}$ alkyl substituted with $CO_2H$, $C_{1-10}$ alkyl substituted with $SO_2NH_2$, $C_{1-10}$ alkyl substituted with $SO_3H$, 2-furyl, 3-furyl, 2-thienyl, 3-thienyl, 2-furyl substituted with K, 3-furyl substituted with K, 2-thienyl substituted with K, 3-thienyl substituted with K, 2-furyl substituted with G, 3-furyl substituted with G, 2-thienyl substituted with G, 3-thienyl substituted with G, $C_{1-10}$ alkyl substituted with $CO_2R_5$, $CH_2CH_2SCH_3$, $CH_2$-3-indolyl, $C_{1-2}$ alkyl with an attached 2-furyl, $C_{1-2}$ alkyl with an attached 3-furyl, $C_{1-2}$ alkyl with an attached 2-thienyl, $C_{1-2}$ alkyl with an attached 3-thienyl, $C_{1-2}$ alkyl with an attached 2-furyl substituted with K, $C_{1-2}$ alkyl with an attached 3-furyl substituted with K, $C_{1-2}$ alkyl with an attached 2-thienyl substituted with K, $C_{1-2}$ alkyl with an attached 3-thienyl substituted with K, $C_{1-2}$ alkyl with an attached 2-furyl substituted with G, $C_{1-2}$ alkyl with an attached 3-furyl substituted with G, $C_{1-2}$ alkyl with an attached 2-thienyl substituted with G, $C_{1-2}$ alkyl with an attached 3-thienyl substituted with G, $CH_2$-2-imidazyl, $C_{1-10}$ alkyl substituted with G, $C_{1-10}$ alkyl with an attached phenyl substituted with G, $C_{1-10}$ alkyl with an attached naphthyl substituted with G, phenyl substituted with G, and naphthyl substituted with G;

$R_5$ is selected from the group consisting of $C_{1-10}$ alkyl and $C_{1-10}$ alkyl substituted with phenyl;

Q is selected independently from the group consisting of $C_{1-10}$ alkoxy, $C_{1-10}$ alkyl-S—, $C_{1-10}$ alkoxy substituted with phenyl, and $C_{1-10}$ alkyl-S— substituted with phenyl;

G is selected from the group consisting of cyano, amidino (—C(=NH)NH$_2$), guanidino (—NHC(=NH)NH$_2$), isothiureido (—S—C(=NH)NH$_2$), amino, $C_{1-6}$ alkylamino, $C_{2-12}$ dialkylamino, and imidazyl;

$R_3$ is selected independently from the group consisting of H, $R_6$, halogen, CN, CO—$C_6H_5$, benzoyl substituted with K on the phenyl, CO$_2$H, CO$_2R_7$, CONHR$_8$, CONR$_8R_9$, CO—AA$_4$-T,

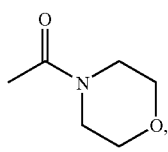, 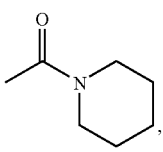,

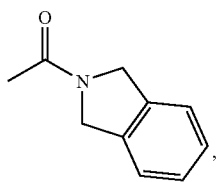, 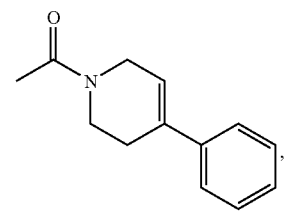,

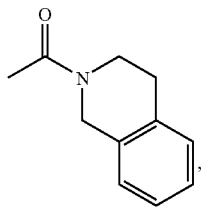, 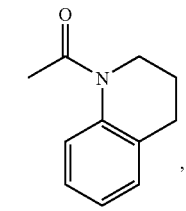, and

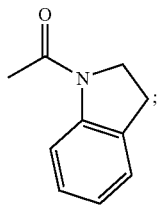;

$R_4$ is selected from the group consisting of $R_6$, halogen, CN, CO—$C_6H_5$, benzoyl substituted with K on the phenyl, CO$_2$H, CO$_2R_7$, CONHR$_8$, CONR$_8R_9$, CO-AA$_4$-T,

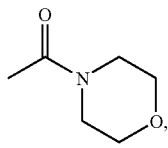, 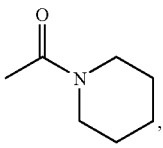,

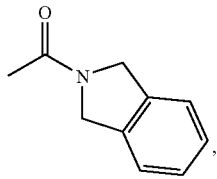, 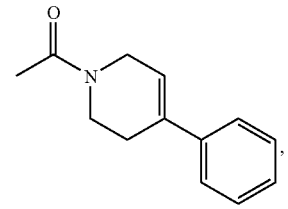,

-continued

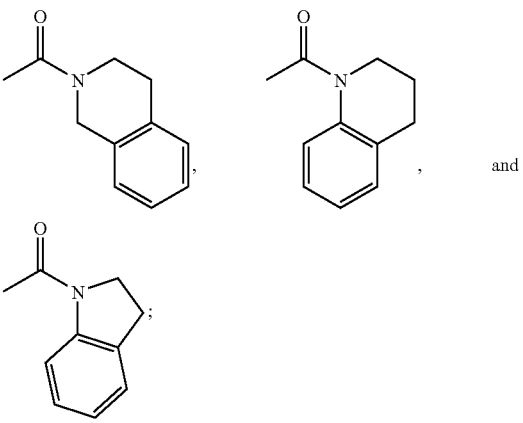

$R_6$ is selected independently from the group consisting of phenyl, phenyl monosubstituted with K, phenyl disubstituted with K, phenyl trisubstituted with K, naphthyl, naphthyl monosubstituted with K, naphthyl disubstituted with K, naphthyl trisubstituted with K, $C_{1-10}$ alkenyl, $C_{3-15}$ cyclized alkyl, $C_{1-10}$ alkyl with a phenyl group attached to the $C_{1-10}$ alkyl, $C_{3-15}$ cyclized alkyl with an attached phenyl group, $C_{1-10}$ alkyl with an attached phenyl group monosubstituted with K, $C_{1-10}$ alkyl with an attached phenyl group disubstituted with K, $C_{1-10}$ alkyl with an attached phenyl group trisubstituted with K, $C_{3-15}$ cyclized alkyl with an attached phenyl group substituted with K, $C_{1-10}$ alkyl with a naphthyl group attached to the $C_{1-10}$ alkyl, $C_{3-15}$ cyclized alkyl with an attached naphthyl group, $C_{1-10}$ alkyl with an attached naphthyl group monosubstituted with K, $C_{1-10}$ alkyl with an attached naphthyl group disubstituted with K, $C_{1-10}$ alkyl with an attached naphthyl group trisubstituted with K, $C_{3-15}$ cyclized alkyl with an attached naphthyl group substituted with K, $C_{1-10}$ alkyl with an attached 2-furyl group, $C_{1-10}$ alkyl with an attached 3-furyl group, $C_{1-10}$ alkyl with an attached 2-pyridyl group, $C_{1-10}$ alkyl with an attached 3-pyridyl group, $C_{1-10}$ alkyl with an attached 4-pyridyl group, 2-furyl, 3-furyl, 2-pyridyl, 3-pyridyl, and 4-pyridyl;

$R_7$ is selected independently from the group consisting of phenyl, phenyl monosubstituted with K, phenyl disubstituted with K, phenyl trisubstituted with K, naphthyl, naphthyl monosubstituted with K, naphthyl disubstituted with K, naphthyl trisubstituted with K, $C_{1-10}$ alkyl, $C_{1-10}$ alkenyl, $C_{3-15}$ cyclized alkyl, $C_{1-10}$ alkyl with a phenyl group attached to the $C_{1-10}$ alkyl, $C_{3-15}$ cyclized alkyl with an attached phenyl group, $C_{1-10}$ alkyl with an attached phenyl group substituted with K, $C_{1-10}$ alkyl with an attached phenyl group disubstituted with K, $C_{1-10}$ alkyl with an attached phenyl group trisubstituted with K, $C_{3-15}$ cyclized alkyl with an attached phenyl group monosubstituted with K, $C_{3-15}$ cyclized alkyl with an attached phenyl group disubstituted with K, $C_{3-15}$ cyclized alkyl with an attached phenyl group trisubstituted with K, $C_{1-10}$ alkyl with a naphthyl group attached to the $C_{1-10}$ alkyl, $C_{3-15}$ cyclized alkyl with an attached naphthyl group, $C_{1-10}$ alkyl with an attached naphthyl group monosubstituted with K, $C_{1-10}$ alkyl with an attached naphthyl group disubstituted with K, $C_{1-10}$ alkyl with an attached naphthyl group trisubstituted with K, $C_{3-15}$ cyclized alkyl with an attached naphthyl group monosubstituted with K, $C_{3-15}$ cyclized alkyl with an attached naphthyl group disubstituted with K, $C_{3-15}$ cyclized alkyl with an attached naphthyl group trisubstituted with K, $C_{1-10}$ alkyl with an attached 2-furyl group, $C_{1-10}$ alkyl with an attached 3-furyl group, $C_{1-10}$ alkyl with an attached 2-pyridyl group, $C_{1-10}$ alkyl with an attached 3-pyridyl group, and $C_{1-10}$ alkyl with an attached 4-pyridyl group;

T is selected independently from the group consisting of OH, $OR_{10}$, $NHR_{11}$, and $NR_{10}R_{11}$;

$AA_4$ is a side chain blocked or unblocked amino acid with the L configuration, D configuration, or no chirality at the alpha-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-amninobutanoic acid, epsilon-aminocaproic acid, citrulline, hydroxyproline, omithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—CH($CH_2CHEt_2$)-$CO_2H$, alpha-aminoheptanoic acid, $NH_2$—CH($CH_2$-1-naphthyl)-$CO_2H$, $NH_2$—CH($CH_2$-2-naphthyl)-$CO_2H$, $NH_2$—CH($CH_2CH_2CH_2$-phenyl)-$CO_2H$, $NH_2$—CH($CH_2$-cyclohexyl)-$CO_2H$, $NH_2$—CH($CH_2$-cyclopentyl)-$CO_2H$, $NH_2$—CH($CH_2$-cyclobutyl)-$CO_2H$, $NH_2$—CH($CH_2$-cyclopropyl)-$CO_2H$, trifluoroleucine, 4-fluorophenylalanine, lysine substituted on the epsilon nitrogen with a biotinyl group, hexafluoroleucine, and

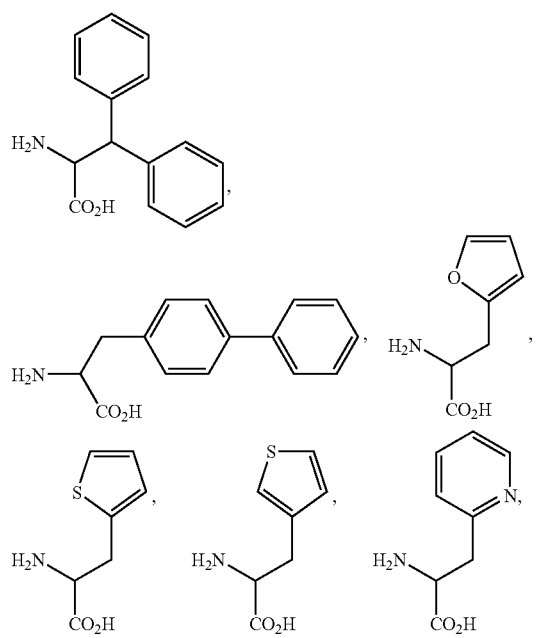

-continued

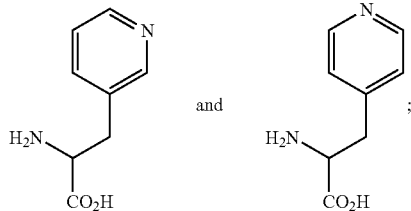

$R_8$ and $R_9$ are selected independently from the group consisting of H, $C_{1-10}$ alkyl, $C_{1-10}$ alkenyl, $C_{3-20}$ cyclized alkyl, $C_{1-10}$ alkyl with a phenyl group attached to the $C_{1-10}$ alkyl, $C_{1-10}$ alkyl with two phenyl groups attached to the $C_{1-10}$ alkyl, $C_{3-20}$ cyclized alkyl with an attached phenyl group, phenyl, phenyl substituted with K, $C_{1-10}$ alkyl with an attached phenyl group substituted with K, $C_{1-10}$ alkyl with an attached phenyl group disubstituted with K, $C_{1-10}$ alkyl with an attached phenyl group trisubstituted with K, $C_{1-10}$ alkyl with two phenyl groups attached to the $C_{1-10}$ alkyl and substituted with K on the phenyl group, $C_{1-10}$ alkyl with two phenyl groups attached to the $C_{1-10}$ alkyl and disubstituted with K on the phenyl groups, $C_{3-20}$ cyclized alkyl with an attached phenyl group substituted with K, $C_{1-10}$ alkyl with a morpholine [—N($CH_2CH_2$)O] ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl, $C_{1-20}$ alkyl with an OH group attached to the alkyl, —$CH_2CH_2CH_2OCH_3$, $C_{1-10}$ alkyl substituted by 1-naphthyl, $C_{1-10}$ alkyl substituted by 2-naphthyl, $C_{1-10}$ alkyl with an attached cyclohexyl group, —NH—$CH_2CH_2$-(4-hydroxyphenyl), —NH—$CH_2CH_2$-(3-indolyl), $C_{1-10}$ alkyl with an attached 2-furyl group, $C_{1-10}$ alkyl with an attached 3-furyl group, $C_{1-10}$ alkyl with an attached 2-pyridyl group, $C_{1-10}$ alkyl with an attached 3-pyridyl group, $C_{1-10}$ alkyl with an attached 4-pyridyl group, and $C_{1-5}$ alkyl with an attached phenyl and a hydroxyl attached to the $C_{1-5}$ alkyl;

$R_{10}$ and $R_{11}$ are selected independently from the group consisting of H, $C_{1-10}$ alkyl, phenyl, nitrophenyl, and $C_{1-10}$ alkyl substituted with phenyl;

Another embodiment of the present disclosure includes the above compounds with formula I, wherein the double bond carbons have stereochemistry selected from the group consisting of cis, trans, E, and Z.

The following exemplary compounds are within the scope of the present disclosure:

Cbz-Val-AAsp-CH═CH—$CH_3$, Cbz-Val-AAsp-CH═CH—CH═CH—$CH_3$, Cbz-Val-AAsp-CH═CH—$CH_2CH_2Ph$,

Cbz-Val-AAsp-CH═CH—Cl, Cbz-Val-AAsp-CH═CH-4-Cl—Ph, Cbz-Val-AAsp-CH═CH—COOEt,

Cbz-Val-AAsp-CH═CH—CONH—n-Bu, Cbz-Val-AAsp-CH═CH—$CONHCH_2Ph$, Cbz-Glu-Val-AAsp-CH═CH—COOEt,

Cbz-Asp-Glu-Val-AAsp-CH═CH—COOEt(trans), Cbz-Asp-Glu-Val-AAsp-CH═CH—COOEt(cis),

Cbz-Asp-Glu-Val-AAsp-CH=CH—COOCH₂Ph,  Cbz-Asp-Glu-Val-AAsp-CH=CH—CONHCH₂Ph,

Cbz-Asp-Glu-Val-AAsp-CH=CH—CONHCH₂-4-F—Ph,  Cbz-Asp-Glu-Val-AAsp-CH=CH—CONHCH₂CH₂Ph,

Cbz-Asp-Glu-Val-AAsp-CH=CH—CON(CH₃)CH₂Ph,  Cbz-Asp-Glu-Val-AAsp-CH=CH—CON(CH₃)CH₂CH₂Ph,

Cbz-Asp-Glu-Val-AAsp-CH=CH—CON(CH₂Ph)₂,  Cbz-Asp-Glu-Val-AAsp-CH=CH—CON(CH₂-1-Napthyl)₂,

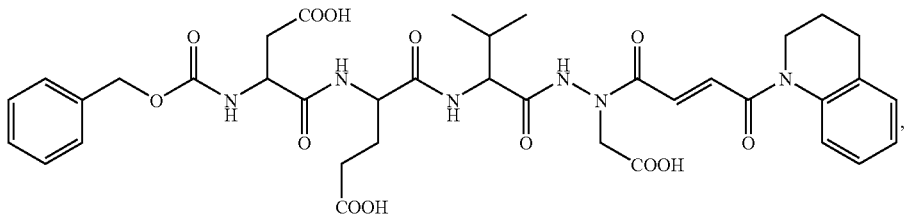

Cbz-Asp-Glu-Val-AAsp-CH=CH—COPh,   Cbz-Val-Glu-Val-AAsp-CH=CH—COOEt,   Cbz-Ile-Glu-Thr-AAsp-CH=CH—COOEt,

Cbz-Ile-Glu-Thr-AAsp-CH=CH—COOCH₂Ph,   Cbz-Ile-Glu-Thr-AAsp-CH=CH—CONHPh,

Cbz-Ile-Glu-Thr-AAsp-CH=CH—CONHCH₂Ph,   Cbz-Ile-Glu-Thr-AAsp-CH=CH—CONHCH₂CH₂Ph,

Cbz-Ile-Glu-Thr-AAsp-CH=CH—CON(CH₃)CH₂Ph,   Cbz-Ile-Glu-Thr-AAsp-CH=CH—CON(CH₃)CH₂CH₂Ph,

Cbz-Ile-Glu-Thr-AAsp-CH=CH—CON(CH₂Ph)₂,   Cbz-Leu-Glu-Thr-AAsp-CH=CH—COOEt,

Cbz-Leu-Glu-Thr-AAsp-CH=CH—COOCH₂Ph,   Cbz-Leu-Glu-Thr-AAsp-CH=CH—CONHCH₂-4-F—Ph,

Cbz-Leu-Glu-Thr-AAsp-CH=CH—CONHPh,   Cbz-Leu-Glu-Thr-AAsp-CH=CH—CONHCH₂Ph,

Cbz-Leu-Glu-Thr-AAsp-CH=CH—CONHCH₂CH₂Ph,   Cbz-Leu-Glu-Thr-AAsp-CH=CH—CON(CH₃)CH₂Ph,

Cbz-Leu-Glu-Thr-AAsp-CH=CH—CON(CH₃)CH₂CH₂Ph,   Cbz-Leu-Glu-Thr-AAsp-CH=CH—CON(CH₂Ph)₂,

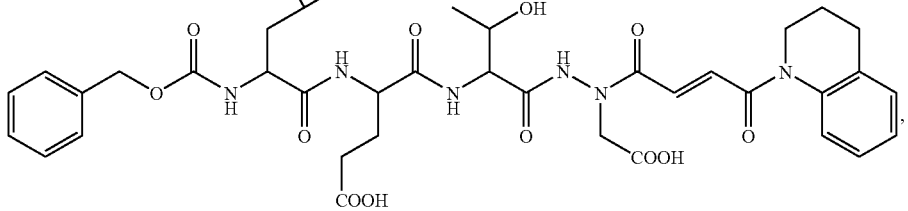

Cbz-Leu-Glu-Thr-AAsp-CH=CH—CON(CH₃)CH₂-1-Napth,   Cbz-Ala-Ala-AAsn-CH=CH—COOBzl, Cbz-Ala-Ala-AAsn-CH=CH—CONEt₂,   Cbz-Ala-Ala-AAsn-CH=CH—CON(Bu)₂,

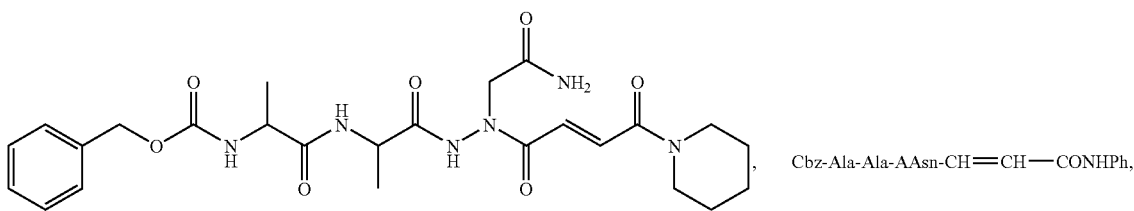, Cbz-Ala-Ala-AAsn-CH=CH—CONHPh,

Cbz-Ala-Ala-AAsn-CH=CH—CONHBzl,   Cbz-Ala-Ala-AAsn-CH=CH—CONHBzl-4-F,

Cbz-Ala-Ala-AAsn-CH=CH—CONHCH₂CH₂Ph,   Cbz-Ala-Ala-AAsn-CH=CH—CON(CH₃)Ph,

Cbz-Ala-Ala-AAsn-CH=CH—CON(CH₃)Bzl,   Cbz-Ala-Ala-AAsn-CH=CH—CON(CH₃)-1-CH₂-Napth, Cbz-Ala-Ala-AAsn-CH=CH—CON(CH₃)CH₂CH₂Ph,   Cbz-Ala-Ala-AAsn-CH=CH—CON(Bzl)Ph, Cbz-Ala-Ala-AAsn-CH=CH—CON(Bzl)₂, -continued
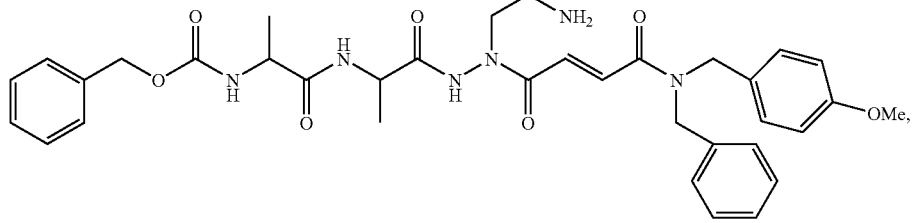
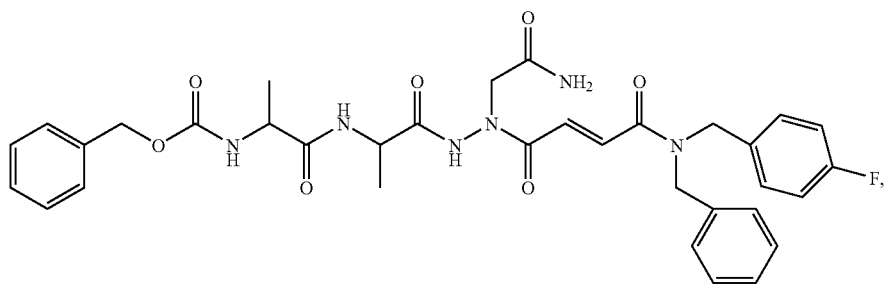
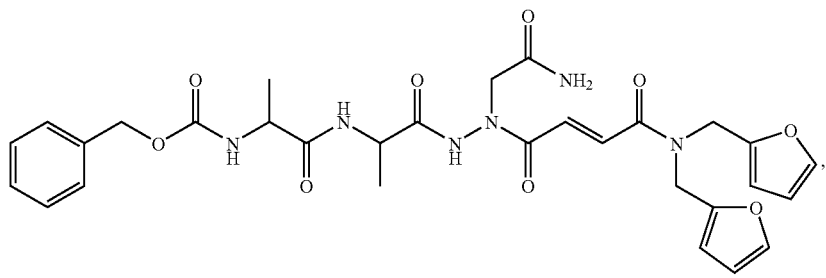
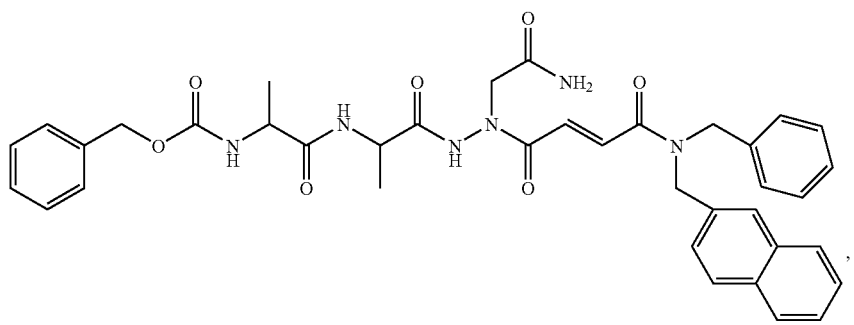
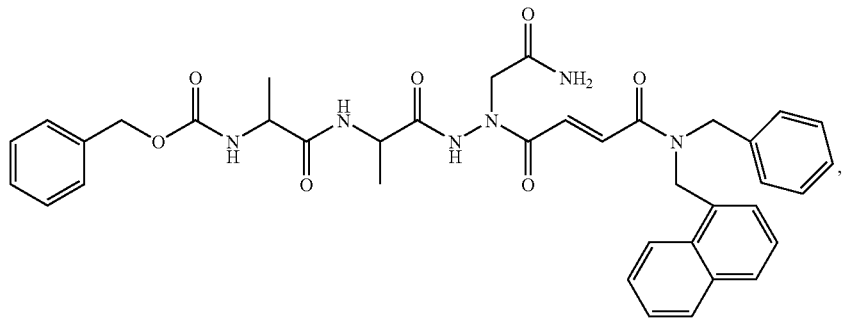
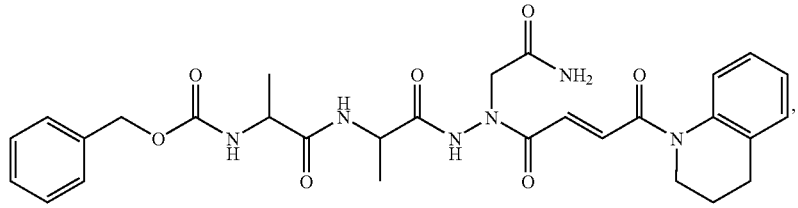

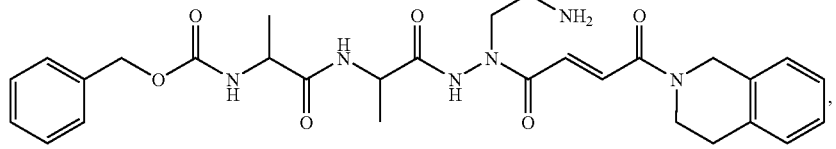

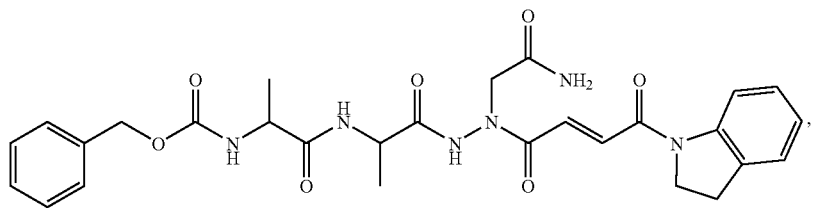

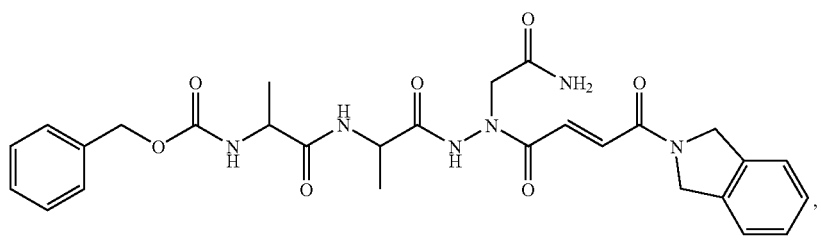

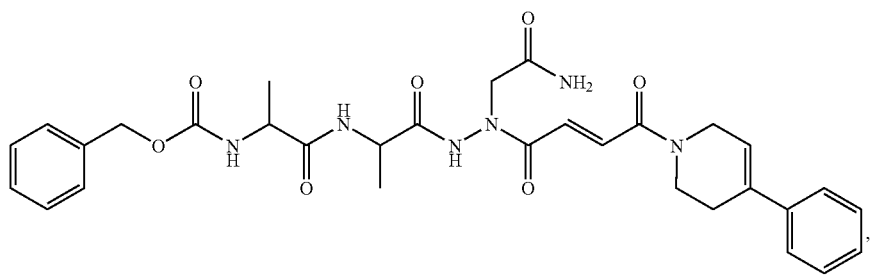

Cbz-Ala-Ala-AAsn-CH=CH—CO—MePhe—N(CH₃)CH₂CH₂Ph,   Cbz-Ala-Ala-AAsn-CH=CH—COPh,

Cbz-Ala-Ala-AAsn-CH=CH—CH=CH—CH₃,   Cbz-Ala-Ala-AAsn-CH=CH-2-furyl,   Cbz-Ala-Ala-AAsn-CH=CH-3-Py,

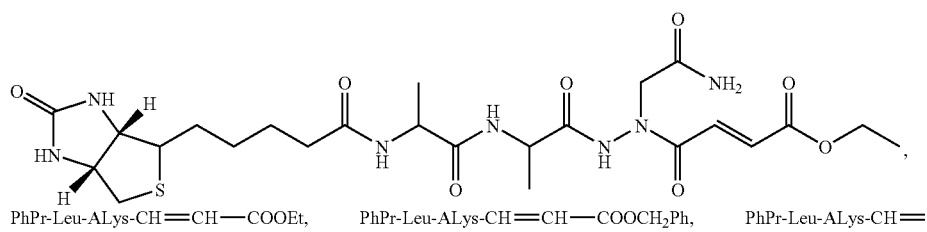

PhPr-Leu-ALys-CH=CH—COOEt,   PhPr-Leu-ALys-CH=CH—COOCH₂Ph,   PhPr-Leu-ALys-CH=CH—CONHCH₂Ph,
PhPr-Leu-ALys-CH=CH—CON(Me)CH₂Ph,   PhPr-Leu-ALys-CH=CH—CON(CH₂Ph)₂,
PhPr-Leu-ALys-CH=CH—CON(Bzl)-p-CH₂C₆H₄,   PhPr-Leu-ALys-CH=CH—CON(Me)CH₂-1-naphthyl,
PhPr-Leu-ALys-CH=CH—CON(Bzl)CH₂-2-naphthyl,   PhPr-Leu-ALys-CH=CH—CON(CH2-1-naphthyl)₂,
PhPr-Leu-ALys-CH=CH—CON(4H-quinoline),   PhPr-Leu-AOrn-CH=CH—COOEt,   PhPr-Leu-AOrn-CH=CH—CONHCH₂Ph,
PhPr-Leu-AOrn-CH=CH—CON(CH₂Ph)₂,   PhPr-Ala-AOrn-CH=CH—COOEt,   PhPr-Leu-AArg-CH=CH—COOEt,
PhPr-Leu-AArg-CH=CH—CONHCH₂Ph,   and   PhPr-Leu-AArg-CH=CH—CON(CH₂Ph)₂.

EXEMPLARY METHODS OF PREPARATION

1. Preparation of the Substituted Propenoate Portion

A variety of propenoates can be synthesized by following the schemes shown below. This substituted propenoate can then be coupled to the respective substituted hydrazide to yield a propenoyl hydrazide using general peptide coupling procedures.

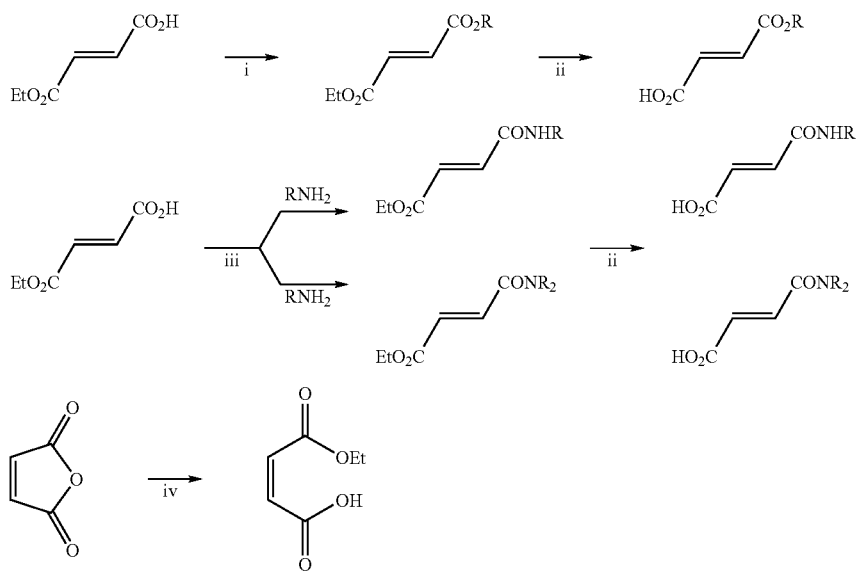

Reagents: (i) NMM, EDC, (ROH such as BzlOH or PhCH$_2$CH$_2$OH), DMF; (ii) KOH, EtOH, r.t.; (iii) NMM, iBCF, CH$_2$Cl$_2$; (iv) EtOH, r.t.

2. Preparation of the Peptide Portion

The peptide portion of the propenoyl hydrazide inhibitor can be prepared using standard peptide chemistry which is well described in publications such as *The Peptides, Analysis, Synthesis, Biology*, Vol. 1-9, published in 1979-1987 by Academic Press; Houben-Weyl Methoden der Organischen Chemie, Vol. 15, Parts 1 and 2, *Synthese von Peptiden*, published by Georg Thieme Verlag, Stuttgart in 1974; and Houben-Weyl Methods of Organic Chemistry, Vol. E22, Parts a, b, c, and d, *Synthesis of Peptides and Peptidomimetics* published by Georg Thieme Verlag, Stuttgart 2000-2003 (references incorporated herein by reference).

The $M_1$ group can be introduced using a number of different reaction schemes. First, it could be introduced directly on an amino acid as shown in the following scheme (top), or the $M_1$ group could be introduced by reaction with an amino acid ester, followed by removal of the ester group to give the same product (bottom).

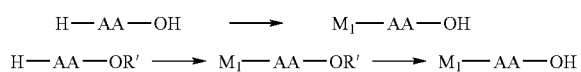

The techniques for introduction of the $M_1$ group are well documented in The Peptides, Houben-Weyel, and many other textbooks on organic synthesis. For example reaction with cyanate or p-nitrophenyl cyanate would introduce a carbamyl group ($M_1$=NH$_2$CO—). Reaction with Me$_2$NCOCl would introduce the Me$_2$NCO— group. Reaction with p-nitrophenyl thiocarbamate would introduce a thio carbamyl group ($M_1$=NH$_2$CS—). Reaction with NH$_2$SO$_2$Cl would introduce the NH$_2$SO$_2$— group. Reaction with Me$_2$NSO$_2$Cl would introduce the Me$_2$NSO$_2$— group. Reaction with a substituted alkyl or aryl isocyanate would introduce the X—NH—CO— group where X is a substituted alkyl or aryl group. Reaction with a substituted alkyl or aryl isothiocyanate would introduce the X—NH—CS— group where X is a substituted alkyl or aryl group. Reaction with X—SO$_2$—Cl would introduce the X—SO$_2$— group. Reaction with a substituted alkyl or aryl acid chloride would introduce an acyl group (M=X—CO—). For example, reaction with MeO—CO—CH$_2$CH$_2$—CO—Cl would give the X—CO— group where X is a C$_2$ alkyl substituted with a C$_1$ alkyl-OCO— group. Reaction with a substituted alkyl or aryl thioacid chloride would introduce a thioacyl group (M=X—CS—). Reaction with a substituted alkyl or aryl sulfonyl chloride would introduce the X—SO$_2$— group. For example, reaction with dansyl chloride would give the X—SO$_2$— derivative where X was a naphthyl group mono substituted with a dimethylamino group. Reaction with a substituted alkyl or aryl chloroformate would introduce the X—O—CO— group. Reaction with a substituted alkyl or aryl chlorothioformate would introduce the X—O—CS—. There are many alternate reaction schemes which could be used to introduce all of the above $M_1$ groups to give either $M_1$-AA-OH or $M_1$-AA-OR'.

The $M_1$-AA-OH derivatives could then be used directly in the preparation of peptide hydrazides or could be converted into the dipeptides, tripeptides, and tetrapeptides $M_1$-AA-AA-OH, $M_1$-AA-AA-AA-OH, or $M_1$-AA-AA-AA-AA-OH which could then be converted to peptide hydrazides. The substituted peptides $M_1$-AA-AA-OH, $M_1$-AA-AA-AA-OH, or $M_1$-AA-AA-AA-AA-OH could also be prepared directly from H-AA-AA-OH, H-AA-AA-AA-OH, or H-AA-AA- AA-AA-OH using the reactions described above for introduction of the $M_1$ group. Alternatively, the $M_1$ group could be introduced by reaction with carboxyl blocked peptides to give $M_1$-AA-AA-OR', $M_1$-AA-AA-AA-OR', or $M_1$-AA-AA-AA-AA-OR', followed by the removal of the blocking group R'.

3. Peparation of Peptide Hydrazides

Usually, peptide hydrazides are synthesized by reaction of an amino acid or peptide ester with hydrazine or by direct coupling of an amino acid or peptide acid with hydrazine as shown in the following two figures. They can also be synthesized directly by reaction of an amino acid or peptide ester with hydrazine.

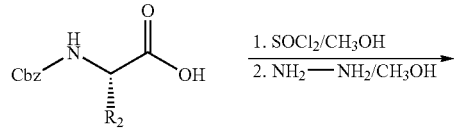

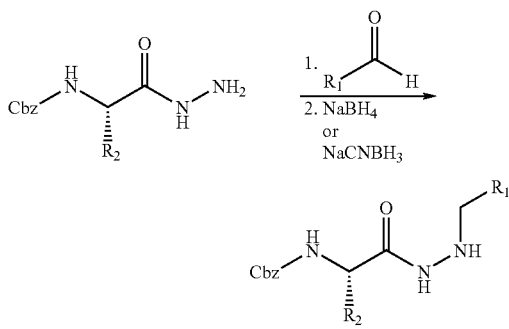

The side chain of the aza-amino acid residue can be introduced by reductive amination as shown specifically in the previous figure or by other methods known by those skilled in the art or by alkylation as shown in the following figure.

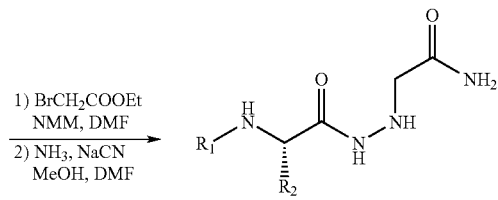

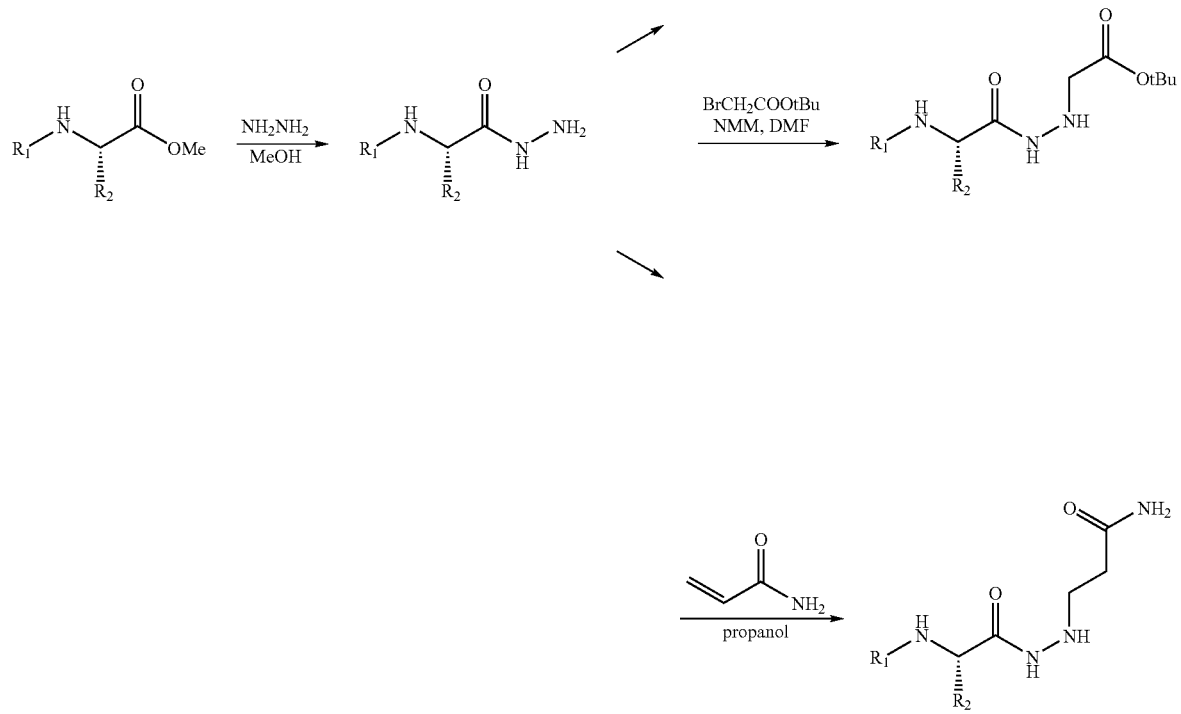

The aza-amino acid side chain can also be introduced by coupling the peptide precursor to the desired hydrazide side chain as shown in the following figure.
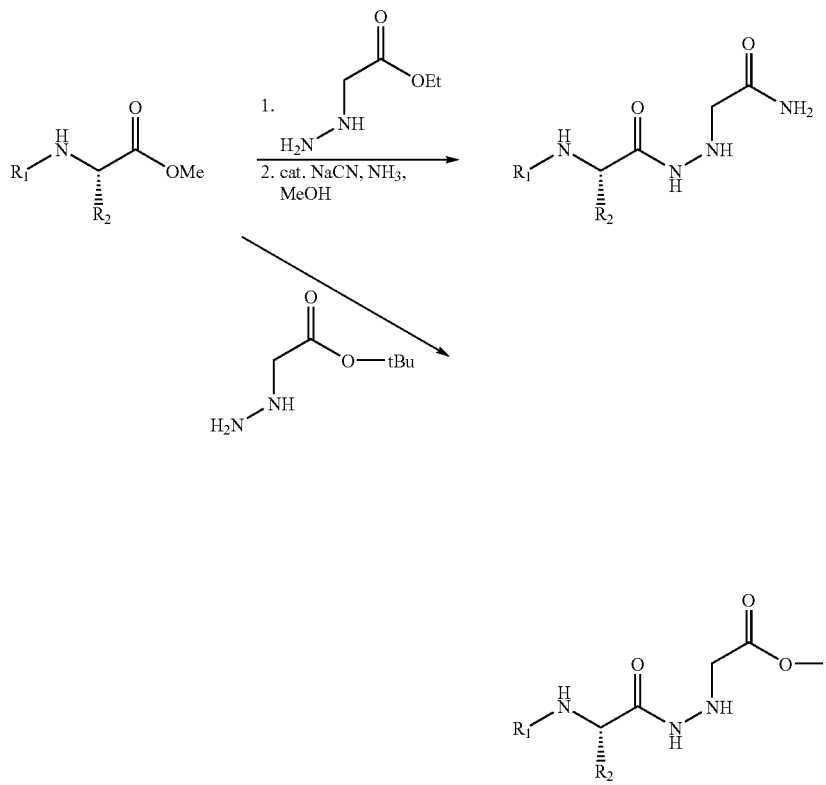
The precursors for basic side chain propenoyl hydrazides were prepared as shown in the following figure.
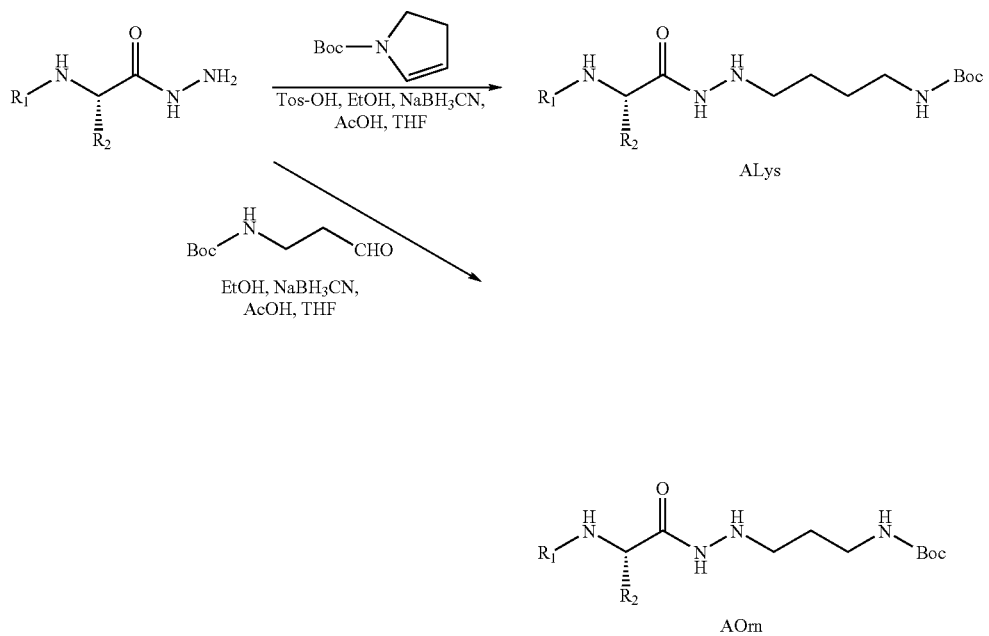

4. Preparation of the Propenoyl Hydrazide

A. EDC/HOBt Coupling Method

The propenoate portion of the propenoyl hydrazide is coupled to the substituted hydrazide by reacting the propenoate portion, the substituted hydrazide, EDC, and HOBt in DMF to form the propenoyl hydrazide (see the following figure).

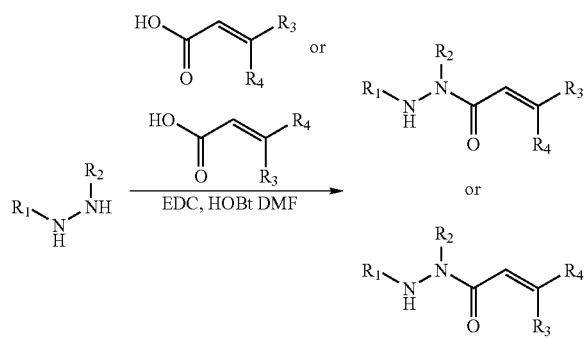

Methods for the protection and deprotection and replacement of an amino protecting group with another moiety are well known. Deprotection of other side chain protecting groups were carried out by standard methods.

B. The Mixed Anhydride Method

Another coupling method is the mixed anhydride method. In this method, the propenoate portion of the propenoyl hydrazide is coupled to the substituted hydrazide by reacting the acrylate portion (carboxylic acid) with NMM in DMF and iBCF followed by the substituted hydrazide to form the propenoyl hydrazide (see the following figure). Methods for the protection and deprotection of side chain protecting groups are well known.

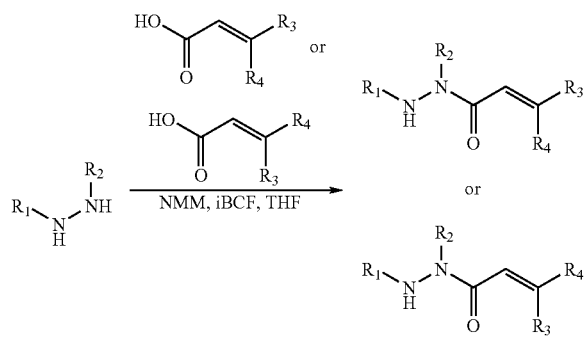

The following figure shows how these methods are used to build the AAsp and AAsn derivatives.

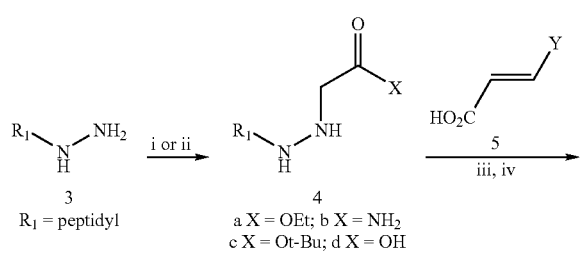

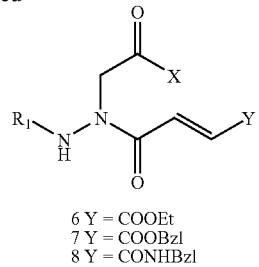

6 Y = COOEt
7 Y = COOBzl
8 Y = CONHBzl

Reagents: (i) $BrCH_2COOEt$, NMM, DMF; $NH_3$/MeOH, 0.1 eq NaCN, DMF. (ii) $BrCH_2COO$-tBu, NMM DMF. (iii) 3, EDC, HOBt, DMF or NMM, iBCF, DMF. (iv) TFA (can be used to deblock the t-Butyl Group in certain peptides where X=O-tBu).

Examples of the preceding methods are exhibited below and in the examples:

5. Synthetic Procedures and Examples

A. Material and Methods

Mono and dipeptidyl methyl esters were purchased from Bachem Bioscience Inc., King of Prussia, Pa. Tripeptides were synthesized using standard coupling procedures such as the mixed anhydride method. The $^1H$ NMR spectra were obtained using a Varian Mercury 400 MHz spectrometer. Electrospray ionization (ESI), fast-atom-bombardment (FAB) and high-resolution mass spectrometry were performed using Micromass Quattro LC and VG Analytical 70-SE instruments. Elemental analysis was performed by Atlantic Microlab Inc., Norcross, Ga.

B. Preparation of Peptidyl Hydrazides (3).

Anhydrous hydrazine (10 eq) was added to a solution of the peptidyl methyl ester (1 eq) in MeOH at room temperature, and the resulting mixture was then stirred for 16 hours. As with most hydrazides, excess hydrazine and solvent were removed by evaporation. The resulting residue was washed with ethanol and ether to give the desired peptidyl hydrazide (3) as a white solid. MS and $^1H$ NMR ($CDCl_3$ or DMSO-$d_6$) were consistent with the proposed structures.

PhPr-Val-Ala-NHNH$_2$, white solid, yield 75%.

Cbz-Asp(O-tBu)-Glu(O-tBu)-Val-NHNH$_2$ was purified by chromatography on a silica gel column using 1:9 MeOH: $CH_2Cl_2$ as the eluent; white solid, yield 56%.

Cbz-Leu-Glu(O-tBu)-Thr-NHNH$_2$, white solid, yield 97%.

N-Benzyloxycarbonylalanylalanyl Hydrazide (Cbz-Ala-Ala-NHNH$_2$) was synthesized from Cbz-Ala-Ala-OMe by hydrazinolysis; white solid (57% yield). $^1H$ NMR (DMSO-$d_6$): 1.1-1.3 (d, $CH_3$), 4.0-4.1 (m, 1H, α-H), 4.1-4.3 (m, 2H, α-H and NH), 5.05 (s, 2H, Cbz), 7.3-7.4 (m, 5H, Ph), 7.5 (d, 1H, NH), 7.9 (d, 1H, NH), 9.05 (s, 1H, NH).

Cbz-Leu-Leu-NHNH$_2$, white solid, yield 98%.

Cbz-Val-NHNH$_2$, white solid, yield 92%.

Cbz-Val-Glu(O-tBu)-Val-NHNH$_2$, white solid, yield 75%.

Cbz-Glu(O-tBu)-Val-NHNH$_2$ was purified by chromatography on a silica gel column using 1:9 MeOH:$CH_2Cl_2$ as the eluent; white solid, yield 47-53%.

Cbz-Ile-Glu(O-tBu)-Thr-NHNH$_2$, white solid, yield 91%.

C. Preparation of PhPr-Leu-NHNH(CH$_2$)$_4$—NH-Boc and PhPr-Leu-NHNH(CH$_2$)$_3$—NH-Boc Boc-NH—(CH$_2$)$_2$—CHO. To a solution of 3-(t-butyloxycarbonylamino)propanol (1.419 g, 8.1 mmol) dissolved in DMSO (15 mL), IBX (2 eq, 4.5 g, 16.2 mmol) was added to form a slurry. The reaction was allowed to stir at rt for 5 hr.

The solid IBX dissolved slowly, but a white precipitate formed after approximately 1 hr of reaction time. Distilled water (80 mL) was added to the reaction mixture, and the resultant aqueous solution filtered and then extracted with diethyl ether (3×175 mL). The organic layers were combined, dried over MgSO$_4$, filtered, and evaporated. The crude oil was purified by silica gel chromatography using 10% CH$_3$OH in CH$_2$Cl$_2$ as the eluent. The solvent was evaporated to leave a clear, colorless oil with a very pleasant flowery or candy-like scent: yield 67%; one spot on TLC, Rf=0.70 (10% CH$_3$OH in CH$_2$Cl$_2$). $^1$H NMR (CDCl$_3$) δ 9.80 (s, 1H), 4.94 (s, 1H), 3.47-3.38 (m, 2H), 2.27-2.65 (t, 2H), 1.47 (s, 9H). MS (ESI$^+$) m/z 174 (M+1).

1-(t-Butyloxycarbonyl)-3,4-dihydropyrrole. To a solution of 4-(t-butyloxycarbonylamino)butanol (1.540 g, 8.1 mmol) in DMSO (15 mL), IBX (2 eq, 4.5 g, 16.2 mmol) was added at rt and reacted for 5.7 hr. The remainder of the workup was similar to that used for Boc-NH—(CH$_2$)$_2$—CHO. The crude oil was purified by silica gel chromatography in 10% CH$_3$OH in CH$_2$Cl$_2$ and concentrated, leaving the product as a clear, faintly yellow oil: yield 58%; one spot on TLC, Rf=0.71 (10% CH$_3$OH in CH$_2$Cl$_2$). $^1$H NMR (CDCl$_3$) δ 5.47 (s, 1H), 5.40 (s, 1H), 3.60-3.20 (m, 2H), 2.14-1.74 (m, 2H), 1.45 (s, 9H). MS (ESI$^+$) m/z 170 (M+1).

PhPr-Leu-NHN=CH(CH$_2$)$_2$—NH-Boc. This procedure is based on the method used by Gray and Parker [Gray and Parker et al, *Tetrahedron* 31, 2940-2943, (1975); incorporated herein by reference] to prepare Boc-3-aminopropanal benzoylhydrazone. To a solution of Boc-NH—(CH$_2$)$_2$CHO (0.942 g, 5.43 mmol) dissolved in absolute ethanol (11 mL) at rt, PhPr-Leu-NHNH$_2$ (1.498 g, 5.43 mmol) was added to form a slurry. The reaction mixture was allowed to stir at rt overnight. The solvent was evaporated and the crude product dissolved in CH$_2$Cl$_2$ (50 mL). The organic layer was washed with a 10% citric acid solution (3×40 mL), a saturated NaHCO$_3$ solution (3×25 mL), and a saturated NaCl solution (3×25 mL). The organic layer was dried over MgSO$_4$, filtered, and concentrated. The material was then purified by silica gel chromatography using 10% CH$_3$OH in CH$_2$Cl$_2$ as the eluent. The eluent was evaporated, giving a white, foamy solid that was used without further purification: yield 82%; product spot by TLC, Rf=0.56 (10% CH$_3$OH in CH$_2$Cl$_2$). $^1$H NMR (CDCl$_3$) δ 10.05 (s, 1H), 8.90 (s, 1H), 7.40-7.08 (m, 5H), 6.30-6.16 (t, 1H), 5.52-5.36 (t, 1H), 4.52-4.40 (m, 1H), 3.44-3.28 (m, 2H), 3.00-2.86 (m, 2H), 2.57-2.44 (m, 4H), 1.71-1.44 (m, 3H), 1.40 (s, 9H), 0.98-0.82 (m, 6H). MS (ESI$^+$) m/z 433 (M+1).

PhPr-Leu-NHN=CH(CH$_2$)$_3$—NH-Boc. This procedure is a modification of the method used by Gray and Parker [Gray and Parker et al, *Tetrahedron* 31, 2940-2943, (1975); incorporated herein by reference] to prepare Boc-3-aminopropanal benzoylhydrazone. The 1-(t-butyloxycarbonyl)-3,4-dihydropyrrole (0.805 g, 4.76 mmol) was reacted with PhPr-Leu-NHNH$_2$ (1.320 g, 4.76 mmol) and p-toluene sulfonic acid monohydrate (0.3 eq, 0.272 g, 1.43 mmol) in absolute ethanol (12 mL) at rt. The remainder of the workup was similar to the procedure used to synthesize PhPr-Leu-NH—N=CH(CH$_2$)$_2$—NH-Boc. The crude product was purified by silica gel chromatography using 10% CH$_3$OH in CH$_2$Cl$_2$ as the eluent. The eluent was evaporated to give a foamy white solid, which was used without further purification: yield 73%; product spot by TLC, Rf=0.55 (10% CH$_3$OH in CH$_2$Cl$_2$). $^1$H NMR (CDCl$_3$) δ 9.77 (s, 1H), 8.80 (s, 1H), 7.43-7.13 (m, 5H), 6.07-5.89 (t, 1H), 5.45-5.34 (t, 1H), 4.48-4.31 (m, 1H), 3.20-3.09 (t, 2H), 3.00-2.87 (m, 2H), 2.59-2.42 (m, 2H), 2.40-2.28 (m, 2H), 2.08-1.90 (m, 2H), 1.8-1.64 (m, 3H), 1.42 (s, 9H), 1.00-0.78 (m, 6H). MS (FAB$^+$) m/z 447 (M+1).

PhPr-Leu-NHNH(CH$_2$)$_3$—NH-Boc. This procedure is based on the method used by Gallina et al. to synthesize a series of Z-hydrazines [Calbretta et al, *Eur. J. Med. Chem.* 30, 931-941 (1995); incorporated herein by reference]. PhPr-Leu-NH—N=CH(CH$_2$)$_2$—NH-Boc (1.928 g, 4.46 mmol) and NaBH$_3$CN (5 eq, 1.400 g, 22.3 mmol) were dissolved in anhydrous THF (23 mL). Glacial acetic acid (104 eq, 27.85 g, 464 mmol, 26.5 mL) was added dropwise to the solution, and the reaction mixture was allowed to stir at rt overnight. The solvents were evaporated and the crude oil dissolved in ethyl acetate (20 mL). Distilled water (20 mL) was added to the solution, which was vigorously stirred while enough solid NaHCO$_3$ was added to turn the pH of the aqueous layer basic. The organic layer was isolated and washed with a saturated NaCl solution (2×15 mL), a saturated NaHCO$_3$ solution (10 mL), and again with a saturated NaCl solution (10 mL). The organic layer was dried over MgSO$_4$, filtered, and evaporated. The crude solid was purified by silica gel chromatography using 1/1 ethyl acetate/hexanes as the eluent. The solvent was evaporated, leaving a white, foamy solid that was used without further purification: yield 59%; product spot on TLC, Rf=0.43 (10% CH$_3$OH in CH$_2$Cl$_2$). $^1$H NMR (CDCl$_3$) δ 9.80 (s, 1H), 9.54 (s, 1H), 7.30-7.13 (m, 5H), 6.94 (s, 1H), 6.60 (s, 1H), 4.60-4.47 (m, 1H), 3.25-3.06 (m, 2H), 3.04-2.93 (m, 4H), 2.60-2.51 (m, 2H), 2.87-1.72 (m, 3H), 1.70-1.60 (m, 2H), 1.42 (s, 9H), 0.98-0.82 (m, 6H). MS (ESI$^+$) m/z 435 (M+1).

PhPr-Leu-NHNH(CH$_2$)$_4$—NH-Boc. This procedure is based on the method used by Gallina et al. to synthesize a series of Z-hydrazines hydrazines [Calbretta et al, *Eur. J. Med. Chem.* 30, 931-941(1995); incorporated herein by reference]. PhPr-Leu-NHN=CH(CH$_2$)$_3$—NH-Boc (1.543 g, 3.46 mmol) and NaBH$_3$CN (5 eq, 1.086 g, 17.3 mmol) dissolved in anhydrous THF (24 mL) were reacted with glacial acetic acid (104 eq, 21.608 g, 360 mmol, 20.6 mL). The remainder of the workup was similar to that used for PhPr-Leu-NHNH—(CH$_2$)$_3$—NH-Boc. The crude product was purified by silica gel chromatography using 1/1 ethyl acetate/hexanes as the eluent. The solvent was evaporated to give a clear, colorless oil. Treatment with CH$_2$Cl$_2$, followed by diethyl ether and evaporation gave a white, foamy solid, which was used without further purification: yield 49%; product spot on TLC, Rf=0.67 (10% CH$_3$OH in CH$_2$Cl$_2$). $^1$H NMR (CDCl$_3$) δ 9.00 (s, 1H), 8.75 (s, 1H), 7.28-7.12 (m, 5H), 4.86 (s, 1H), 4.80 (s, 1H), 4.51-4.42 (m, 1H), 3.24-3.04 (m, 2H), 3.02-2.93 (m, 4H), 2.77-2.68 (m, 2H), 2.62-2.48 (m, 2H), 2.01-1.90 (m, 1H), 1.88-1.78 (m, 2H), 1.76-1.60 (m, 4H), 1.42 (s, 9H), 0.97-0.82 (m, 6H). MS (ESI$^+$) m/z 449 (M+1).

D. Preparation of the Peptidyl Aza-Asn Precursor (Cbz-Ala-Ala-NHNHCH$_2$CONH$_2$)

Preparation of Cbz-Ala-Ala-NHNHCH$_2$COOEt (4a). Ethyl bromoacetate (1.1 eq) was added dropwise to a stirred solution of Cbz-Ala-Ala-NHNH$_2$ (1 eq) and NMM (1.1 eq) in DMF that was cooled to −10° C. The resulting solution was stirred for 30 min at −10° C., after which the mixture was allowed to react at room temperature for 36 hours. The DMF was evaporated, and the residue was purified on a silica gel column using 1:9 MeOH:CH$_2$Cl$_2$ as the eluting solvent system to afford 4a as a white solid (yield=36%). $^1$H NMR (DMSO-d$_6$): 1.18 (t, 9H, CH$_3$), 3.5 (d, 2H, NCH$_2$COOEt), 4.0-4.15 (m, 3H, α-H and OCH$_2$CH$_3$), 4.2 (m, 1H, α-H), 5.03 (m, 2H, Cbz), 5.18 (m, 1H, NH), 7.22-7.40 (m, 5H, Ph), 7.4-7.5 (d, 1H, NH), 7.9 (m, 1H, NH), 9.35 (m, 1H, NH). MS (FAB) m/z 395 [(M+1)$^+$].

Preparation of $N^1$-N-Benzyloxycarbonylalanylalanyl-$N^2$-carbamoylmethylhydrazine (Cbz-Ala-Ala-NHNHCH$_2$CONH$_2$, 4b). The ethyl ester (4a) was converted to the amide (4b) by the method described by [Hogberg et al. J. Org. Chem. 2033-2066 (1987); incorporated herein by reference]. The ethyl ester Cbz-Ala-Ala-NHNHCH$_2$COOEt (4a, 1 eq) was dissolved in a 9 M solution of NH$_3$ in methanol and a small amount of DMF, and allowed to stir on an ice bath. To this solution was added NaCN (0.1 eq). The flask was closed with a rubber septum and allowed to stir at 0° C. for three days. The solvent was evaporated and the product was precipitated with 1:9 MeOH:CH$_2$Cl$_2$ and methanol to yield a white solid (68% yield). $^1$H NMR (DMSO-d$_6$): 1.18 (d, 6H, CH$_3$), 3.2 (d, 2H, NCH$_2$CONH$_2$), 4.0-4.12 (m, 1H, α-H), 4.2 (m, 1H, α-H), 5.03 (m, 2H, Cbz), 5.22 (m, 1H, NH), 7.18 (d, 1H, NH), 7.3-7.5 (m, 6H, Ph and NH), 8.0 (m, 1H, NH), 9.38 (m, 1H, NH). MS (FAB) m/z 366 [(M+1)$^+$]. HRMS (FAB) Calcd. For C$_{16}$H$_{24}$N$_5$O$_5$: 366.17774. Observed m/z 366.17665.

D. Preparation of the t-Bu Protected Peptidyl Aza-Asp Precursors

Preparation of Peptidyl-AA$_2$-NHNHCH$_2$COO-tBu (4c). Neat t-butyl bromoacetate (1 eq) was added to a stirred solution of the peptide hydrazide (3) and NMM (1 eq) in DMF pre-cooled at −10° C. The resulting solution was stirred for 30 min at −10° C., after which the mixture was allowed to react at room temperature for 20 hours. The DMF was removed by evaporation, and the resulting residue was washed with water, filtered, and dried in vacuo. Purification on a silica gel column using the appropriate solvent gave 4c (yields=48-65%). MS and $^1$H NMR (DMSO-d$_6$ or CDCl$_3$) were consistent with the proposed structure.

PhPr-Val-Ala-NHNHCH$_2$COO-tBu was purified by chromatography on silica gel column using 1:7 MeOH:CH$_2$Cl$_2$ as the eluent; white solid, yield 56%.

Cbz-Val-NHNHCH$_2$COO-tBu was purified by column chromatography on silica gel using 1:20:4.2 MeOH:CH$_2$Cl$_2$:EtOAc as the eluent; white solid, yield 64%. $^1$H NMR (DMSO-d$_6$): 0.90 (t, 6H, Val), 1.40 (s, 9H, tBu), 1.86 (m, 1H, Val), 3.37 (d, 2H, NHCH$_2$COOH), 3.72 (t, 1H, α-H), 4.99 (s, 2H, Cbz), 5.13 (d, 1H, NH), 7.30 (s, 5H, Ph), 9.38 (d, 1H, NH).

Cbz-Asp(O-tBu)-Glu(O-tBu)-Val-NHNHCH$_2$COO-tBu was purified by column chromatography on silica gel using 2:18:5 MeOH:CH$_2$Cl$_2$:EtOAc as the eluent; white solid, yield 65%. MS (ESI) nm/z 736.6 [(M+1)$^+$]. $^1$H NMR (DMSO-d$_6$): 0.90 (d, 6H, Val), 1.49 (s, 27H, tBu), 1.85-2.20 (m, 3H, Val and Glu), 2.21 (m, 2H, Glu), 2.40-2.70 (m, 2H, Asp CH$_2$), 3.30 and 3.38 (m, 3H, NHCH$_2$ and NHCH$_2$), 4.05-4.30 (m, 3H, α-H), 5.05 (m, 2H, Cbz), 7.20-7.40 (m, 5H, Ph), 7.60-7.95 (m, 3H, NH), 9.2 (m, 1H, NH).

Cbz-Glu(O-tBu)-Val-NHNHCH$_2$COO-tBu was purified by column chromatography on silica gel using 2:18:5 MeOH:CH$_2$Cl$_2$:EtOAc as the eluent; white solid, yield 78%. MS (ESI) m/z 565.3 [(M+1)$^+$], $^1$H NMR (CDCl$_3$): 0.95 (t, 6H, Val), 1.49 (s, 18H, tBu), 1.85-2.20 (m, 3H, Val and Glu), 2.21 (m, 2H, Glu), 3.45-3.70 (m, 3H, NHCH$_2$ and NHCH$_2$), 4.25-4.30 (m, 2H, α-H), 5.05 (m, 2H, Cbz), 5.85 (d, 1H, NH), 7.05 (d, 1H, NH), 7.20-7.40 (m, 5H, Ph), 8.00 (m, 1H, NH).

Cbz-Leu-Glu(O-tBu)-Thr-NHNHCH$_2$COO-tBu was purified by column chromatography on silica gel using 1:9 MeOH:CH$_2$Cl$_2$ as the eluent; white solid, yield 34%. MS (ESI) m/z 680 [(M+1)$^+$]. $^1$H NMR (DMSO-d$_6$): 0.7-0.9 (t, 6H, Leu CH$_3$), 1.0 (d, 3H, Thr CH$_3$), 1-1.3 (m, 2H, Leu CH$_2$), 1.3-1.5 (m, 18H, tBu), 1.5-1.8 (m, 2H, Leu CH and Glu CH$_2$), 1.8-1.95 (m, 1H, Glu CH$_2$), 2.1-2.3 (m, 2H, Glu CH$_2$), 3.4 (d, 2H, NCH$_2$), 3.9 (m, 1H, α-H), 4.1 (m, 1H, α-H and Thr CH—OH), 4.3 (m, 1H, α-H), 4.9 (d, 1H, NH), 5.03 (m, 2H, Cbz), 7.3-7.4 (m, 5H, phenyl), 7.5 (d, 1H, NH), 7.6 (d, 1H, NH), 8.05 (d, 1H, NH), 9.2 (d, 1H, NH).

Cbz-Ile-Glu(O-tBu)-Thr-NHNHCH$_2$COO-tBu was purified by column chromatography on silica gel using 1:9 MeOH:CH$_2$Cl$_2$ as the eluent; white solid, yield 26%. MS (ESI) m/z 680 [(M+1)$^+$]. $^1$H NMR (DMSO-d$_6$): 0.7-0.9 (t, 6H, Ile CH$_3$), 0.9-1.0 (d, 3H, Thr CH$_3$), 1-1.2 (m, 2H, Ile CH$_2$), 1.3-1.5 (s, 18H, tBu), 1.6-1.8 (m, 2H, Ile CH and Glu CH$_2$), 1.8-1.9 (m, 1H, Glu CH$_2$), 2.1-2.3 (m, 2H, Glu CH$_2$), 3.4 (d, 2H, NCH$_2$), 3.9 (m, 2H, α-H), 4.1 (m, 1H, α-H), 4.35 (m, 1H, Thr CH—OH), 4.8 (d, 1H, NH), 5.03 (s, 2H, Cbz), 5.05 (d, 1H, NH), 7.3-7.4 (m, 5H, phenyl), 7.7 (d, 1H, NH), 8.05 (d, 1H, NH), 9.2 (s, 1H, NH).

Cbz-Val-Glu(O-tBu)-Val-NHNHCH$_2$COO-tBu was purified by column chromatography on silica gel using 1:9:5 MeOH:CH$_2$Cl$_2$:EtOAc as the eluent, and then rechromatographed using 1:9:5 MeOH:CH$_2$Cl$_2$:EtOAc as the eluent; white solid, yield 18%. $^1$H NMR (DMSO-d$_6$): 0.78-0.85 (dd, 12H, Val), 1.40 (d, 18H, tBu), 1.71 (m, 1H, Val), 1.83 (m, 2H, Glu), 1.91 (m, 1 h, Val), 2.17 (m, 2H, Glu), 3.86 (t, 1H, α-H), 4.04 (t, 1H, α-H), 4.32 (m, 1H, α-H), 5.01 (s, 2H, Cbz), 5.12 (m, 1H, NH), 7.33 (s, 5H, Ph), 7.76 (d, 1H, NH), 8.00 (d, 1H, NH), 9.43 (d, 1H, NH).

E. Preparation of Monoethyl Maleate (HOOCCH=CH—COOEt)

Monoethyl maleate was obtained as a colorless oil from the reaction of maleic anhydride with absolute ethanol at room temperature for 18 hours (yield=86%) [Batchelor et al, J. Chem. Soc. Perkin Trans. I 985-995 (1998); incorporated herein by reference]. $^1$H NMR (DMSO-d$_6$): 1.19 (t, 3H, OCH$_2$CH$_3$), 4.11 (q, 2H, OCH$_2$CH$_3$), 6.33 (s, 2H, CH=CH).

F. Preparation of Benzylnaphthyl-2-ylmethylamine (Bzl-NHCH$_2$-2-Napth)—Reductive Amination Procedure.

Benzylamine (1 eq) was dissolved in absolute ethanol. A solution of 2-naphthaldehyde (1 eq) in absolute ethanol was added dropwise via an addition funnel to the benzylamine solution while stirring. The mixture was heated at reflux for 2 hours. Sodium borohydride (2.1 eq) was added to the mixture. The mixture was heated at reflux for 2 hours. The solvent was removed under reduced pressure. The residue was dissolved in dichloromethane. The solution was washed with aqueous base (NaOH, 1M) and dried (MgSO$_4$). The solvent was removed under reduced pressure to give a clear, colorless oil (90% yield). $^1$H NMR (CDCl$_3$): 2.37 (s, 1H, CH$_2$NHCH$_2$), 3.84 (s, 2H, NHCH$_2$PH), 3.97 (s, 2H, Napth-CH$_2$NH), 7.23-7.50 (m, 8H, Ph, Napth), 7.76-7.81 (m, 4H, Napth).

Bis-furan-2-ylmethylamine (NH(CH$_2$-2-furyl)$_2$). The amine was prepared following the reductive amination procedure (89% yield). $^1$H NMR (CDCl$_3$): 3.84 (s, 4H, CH$_2$NHCH$_2$), 6.29-6.33 (2 dd, 4H, furyl), 7.37-7.38 (dd, 2H, furyl).

Benzyl-(4-methoxybenzyl)amine (BzlNH(Bzl-4-OMe)). The amine was prepared prepared following the reductive amination procedure (98% yield). $^1$H NMR (CDCl$_3$): 2.16 (s, 1H, CH$_2$NHCH$_2$), 3.74 (s, 3H, CH$_3$O), 3.78-3.86 (m, 4H, CH$_2$NHCH$_2$), 6.83-6.97 (m, 2H, MeO-Ph), 7.24-7.33 (m, 7H, Ph).

Benzyl-(4-fluorobenzyl)amine (BzlNH(Bzl-4-F). The amine was prepared following the reductive amination procedure (89% yield). $^1$H NMR (CDCl$_3$): 2.05 (s, 1H, CH$_2$NHCH$_2$), 3.77-3.79 (d, 4H, CH$_2$NHCH$_2$), 6.96-7.02 (m, 4H, F-Ph), 7.19-7.23 (m, 5H, Ph).

Benzylnaphthyl-1-ylmethylamine (BzlNHCH$_2$-1-Napth). The amine was prepared prepared following the reductive amination procedure (97% yield). $^1$H NMR (CDCl$_3$): 2.03 (s, 1H, CH$_2$NHCH$_2$), 3.91 (s, 2H, NHCH$_2$Ph), 4.24 (s, 2H, Napth-CH$_2$NH), 7.22-7.51 (m, 10H, Ph, Napth), 7.71-7.85 (m, 2H, Napth).

G. Preparation of trans-3-Benzyloxycarbonylacrylic Acid or Monobenzyl Fumarate (HOOCCH═CH—COOBzl).

Equimolar amounts of fumaric acid and benzyl alcohol were dissolved in anhydrous DMF. NMM (1 eq) was added at 0° C. followed by EDC after 15 minutes. The reaction was stirred over night at room temperature. DMF was evaporated and the crude residue was redissolved in EtOAc. The product was extracted with saturated aqueous NaHCO$_3$. The aqueous layer was then acidified with 1N HCl to pH 2. The product was extracted with EtOAc, and the organic layer was washed with water and dried (MgSO$_4$). The solvent was evaporated and the crude residue was subjected to column chromatography (MeOH/CH$_2$Cl$_2$) to give a white powder (51% yield). $^1$H-NMR (DMSO-d$_6$): 5.21 (s, 2H, CH═CH—COOCH$_2$Ph), 6.73 (s, 2H, CH═CH—COOCH$_2$Ph), 7.29-7.43 (m, 5H, Ph). MS (ESI) m/z 207 [(M+1)$^+$].

H. General Procedure for Coupling Monoethyl Fumarate to Amines—Mixed Anhydride Coupling.

Coupling of the amine precursors to the fumarates was accomplished using the mixed anhydride coupling method. To a solution of the fumarate (1 eq) in CH$_2$Cl$_2$ at −20° C. was added N-methylmorpholine (NMM, 1 eq) followed by isobutyl chloroformate (iBCF, 1 eq). After the reaction mixture was allowed to stir for 30 min, the amine (1 eq) was added to the mixture. Hydrochloride salts of the amine were pretreated with NMM (1 eq) at −20° C. in CH$_2$Cl$_2$ prior to addition. After 30 mim the reaction was continued to stir for 4 hours at room temperature. The DMF was evaporated and the residue was washed and purified using the same procedure as described above for the EDC/HOBt coupling method. MS and $^1$H NMR (DMSO-d$_6$ or CDCl$_3$) were consistent with the proposed structures. Hydrolysis of the ester by NaOH (1.2 eq) gave the desired amides (yields=40-98%).

trans-3-Dibutylcarbamoylacrylic Acid (HOOCCH═CH—CON(nBu)$_2$). This compound was synthesized using the above procedure with dibutylamine as the starting material. $^1$H-NMR (CDCl$_3$): 0.95 (m, 6H, 2×nBu-CH$_3$), 1.30-1.37 (m, 4H, 2×CH$_2$CH$_2$CH$_2$CH$_3$), 1.53-1.59 (m, 4H, 2×CH$_2$CH$_2$CH$_2$CH$_3$), 3.33 (t, 2H, N—CH$_2$), 3.39 (t, 2H, N—CH$_2$), 6.79-6.83 (d, 1H, J=15.6 Hz, CH═CHCON), 7.33-7.36 (d, 1H, J=15.2 Hz, CH═CHCON).

trans-3-Diethylcarbamoylacrylic Acid (HOOCCH═CH—CONEt$_2$). This compound was synthesized using the above procedure with diethylamine as the starting material. $^1$H-NMR (CDCl$_3$): 1.17-1.21 (t, 3H, N—CH$_2$CH$_3$), 1.22-1.24 (t, 3H, N—CH$_2$CH$_3$), 3.40-3.47 (m, 4H, 2×N—CH$_2$), 6.78-6.82 (d, 1H, J=14.8 Hz, CH═CHCON), 7.31-7.35 (d, 1H, J=14.8 Hz, CH═CHCON).

trans-3-(1-Piperidylcarbonyl)acrylic Acid (HOOCCH═CH—CO-Pip). This compound was synthesized using the above procedure with piperidine as the starting material. $^1$H-NMR (DMSO-d$_6$): 1.46-1.60 (m, 6H, 3×piperidine CH$_2$), 3.45-3.49 (m, 4H, CH$_2$—N—CH$_2$), 6.41-6.44 (d, 1H, J=15.2 Hz, CH═CHCON), 7.33-7.37 (d, 1H, J=15.2 Hz, CH═CHCON).

trans-3-Phenylcarbamoylacrylic Acid (HOOCCH═CH—CONHPh). This compound was synthesized using the above procedure with aniline as the starting material. $^1$H-NMR (DMSO-d$_6$): 6.61-6.65 (d, 1H, J=15.2 Hz, CH═CHCON), 7.02-7.14 (m, 1H, CH═CHCON), 7.14-7.31 (m, 2H, Ph), 7.32 (t, 2H, Ph), 7.66 (d, 2H, Ph), 10.47 (s, 1H, NH).

trans-3-Benzylcarbamoylacrylic Acid (HOOCCH═CH—CONHBzl). This compound was synthesized using the above procedure with benzylamine as the starting material. $^1$H-NMR (DMSO-d$_6$): 4.37 (d, 2H, N—CH$_2$-Ph), 6.52-6.56 (d, 1H, J=15.2 Hz, CH═CHCON), 6.94-6.98 (d, 1H, J=15.6 Hz, CH═CHCON), 7.14-7.31 (m, 5H, Ph), 8.97 (t, 1H, NH).

trans-3-(4-Fluorobenzylcarbamoyl)acrylic Acid (HOOCCH═CH—CONH-Bzl-4-F). This compound was synthesized using the above procedure with 4-fluoro benzylamine as the starting material. $^1$H-NMR (DMSO-d$_6$): 4.34-4.35 (d, 2H, N—CH$_2$-Ph), 6.52-6.55 (d, 1H, J=15.2 Hz, CH═CHCON), 6.93-6.94 (d, 1H, J=15.6 Hz, CH═CHCON), 7.14-7.16 (t, 2H, Ph), 7.27-7.31 (t, 2H, Ph), 8.99 (t, 1H, NH), trans-3-Phenethylcarbamoylacrylic Acid (HOOCCH═CH—CONHCH$_2$CH$_2$Ph). This compound was synthesized using the above procedure with phenethylamine as the starting material. $^1$H-NMR (DMSO-d$_6$): 3.54 (t, 2H, N—CH$_2$—CH$_2$-Ph), 3.61 (t, 2H, N—CH$_2$—CH$_2$-Ph) 6.43-6.47 (d, 1H, J=15.2 Hz, CH═CHCON), 6.98-7.02 (d, 1H, J=15.6 Hz, CH═CHCON), 7.14-7.31 (m, 5H, Ph).

trans-N-Methylphenylcarbamoylacrylic Acid (HOOCCH═CH—CON(CH$_3$)Ph). This compound was synthesized using the above procedure with N-methyl aniline as the starting material. $^1$H-NMR (DMSO-d$_6$): 3.14 (s, 3H, N—CH$_3$), 6.50-6.54 (d, 1H, J=15.2 Hz, CH═CHCON), 6.60-6.64 (d, 1H, J=15.2 Hz, CH═CHCON), 7.32 (t, 2H, Ph), 7.40 (d, 1H, Ph), 7.47 (d, 1H, Ph).

trans-3-Benzylmethylcarbamoylacrylic Acid (HOOCCH═CH—CON(CH$_3$)Bzl). This compound was synthesized using the above procedure with N-methyl benzylamine as the starting material. $^1$H-NMR (DMSO-d$_6$):3.03 (s, 3H, N—CH$_3$), 4.62-4.67 (d, 2H, N—CH$_2$-Ph), 6.83-6.87 (d, 1H, J=16 Hz, CH═CHCON), 7.15-7.17 (d, 1H, J=8 Hz, CH═CHCON), 7.25-7.50(m, 5H, Ph).

trans-3-(Methyl-1-naphthylmethylcarbamoyl)acrylic Acid (HOOCCH═CH—CON(CH$_3$)CH$_2$-1-Napth). This compound was synthesized using the above procedure with N-methyl-1-naphthyl methylamine hydrochloride as the starting material. $^1$H-NMR (DMSO-d$_6$): 3.01 (s, 3H, CH$_3$), 5.01 (s, 2H, CH$_2$), 6.61-6.65 (d, 1H, J=15.2 Hz, CH═CHCON), 7.17-7.21 (d, 1H, CH═CHCON), 7.37-7.60 (m, 4H, naphthyl), 7.85-8.01 (m, 3H, naphthyl).

trans-3-(Methylphenethylcarbamoyl)acrylic Acid (HOOCCH═CH—CON(CH$_3$)CH$_2$CH$_2$Ph). This compound was synthesized using the above procedure with N-methyl phenethylamine as the starting material. $^1$H-NMR (DMSO-d$_6$): 2.82 (s, 3H, N—CH$_3$), 3.54 (t, 2H, N—CH$_2$—CH$_2$-Ph), 3.61 (t, 2H, N—CH$_2$—CH$_2$-Ph), 6.43-6.47 (d, 1H, J=15.2 Hz, CH═CHCON), 6.98-6.7.02 (d, 1H, J=15.6 Hz, CH═CHCON), 7.14-7.31 (m, 5H, Ph).

trans-3-Phenylbenzylcarbamoylacrylic Acid (HOOCCH═CH—CON(Bzl)Ph). This compound was synthesized using the above procedure with phenyl benzylamine as the starting material. $^1$H-NMR (DMSO-d$_6$): 4.97 (s, 2H, N—CH$_2$-Ph), 6.61-6.62 (d, 1H, CH═CHCON), 7.15-7.43 (m, 11H, CH═CHCON and 2×Ph).

trans-3-Dibenzylcarbamoylacrylic Acid (HOOCCH═CH—CON(Bzl)$_2$). This compound was synthesized using the above procedure with dibenzylamine as the starting material. $^1$H-NMR (DMSO-d$_6$): 4.57 (s, 2H, N—CH$_2$-Ph), 4.65 (s, 2H, N—CH$_2$-Ph), 6.59-6.63 (d, 1H, J=15.2 Hz, CH═CHCON), 7.15-7.17 (d, 1H, J=8 Hz, CH═CHCON), 7.25-7.50 (m, 10H, 2×Ph).

trans-3-(Benzyl-4-methoxybenzylcarbamoyl)acrylic Acid (HOOCCH=CH—CON(Bzl-4-OMe)Bzl). This compound was synthesized using the above procedure with 4-methoxybenzyl benzylamine as the starting material. $^1$H-NMR (DMSO-d$_6$): 3.73 (s, 3H, OCH$_3$), 4.50-4.54 (d, 2H, N—CH$_2$-Ph), 4.56-4.61 (d, 2H, N—CH$_2$-Ph), 6.59-6.63 (d, 1H, J=15.2 Hz, CH=CHCON), 6.86-6.92 (2×d, 2H, Ph), 7.07-7.09 (d, 1H, J=8 Hz, CH=CHCON), 7.14-7.39 (m, 7H, 2×Ph).

trans-3-Benzyl-(4-fluorobenzyl)carbamoylacrylic Acid (HOOCCH=CH—CON(Bzl-4-F)Bzl). This compound was synthesized using the above procedure with 4-fluorobenzyl benzylamine as the starting material. $^1$H-NMR (DMSO-d$_6$): 4.50-4.54 (d, 2H, N—CH$_2$-Ph), 4.56-4.61 (d, 2H, N—CH$_2$-Ph), 6.59-6.63 (d, 1H, J=15.2 Hz, CH=CHCON), 6.99-7.44 (m, 11H, CH=CHCON and CH=CH—CON and 2×Ph).

trans-3-(Bis-(2-furylmethyl)carbamoyl)acrylic Acid (HOOCCH=CH—CON(CH$_2$-2-furyl)$_2$. This compound was synthesized using the above procedure with bis-2-furanmethyl amine as the starting material. $^1$H-NMR (DMSO-d$_6$): 2.73 (d, 1H, J=3.6 Hz, furyl), 3.13 (t, 1H, furyl), 3.49 (d, 1H, N—CH$_2$), 4.03 (d, 1H, N—CH$_2$), 4.35-4.49 (dd, 2H, N—CH$_2$), 5.17 (d, 1H, furyl), 6.30-6.40 (m, 3H, furyl), 6.63-6.64 (d, 1H, J=15.2 Hz, CH=CHCON), 7.60 (s, 1H, CH=CHCON).

trans-3-(Benzyl-2-naphthylmethylcarbamoyl)acrylic Acid (HOOCCH=CH—CON(Bzl)-2-CH$_2$-Napth). This compound was synthesized using the above procedure with benzyl-2-naphthylmethylamine as the starting material. $^1$H-NMR (DMSO-d$_6$): 4.82 (d, 2H, N—CH$_2$), 5.01 (d, 2H, N—CH$_2$), 6.61-6.65 (d, 1H, J=15.2 Hz, CH=CHCON), 7.17-7.21 (d, 1H, CH=CHCON), 7.37-7.60 (m, 9H, naphthyl and Ph), 7.85-8.01 (m, 3H, naphthyl).

trans-3-(Benzyl-1-naphthylmethylcarbamoyl)acrylic Acid (HOOCCH=CH—CON(Bzl)-1-CH$_2$-Napth). This compound was synthesized using the above procedure with benzyl-1-naphthylmethylamine as the starting material. $^1$H-NMR (DMSO-d$_6$): 4.82 (d, 2H, N—CH$_2$), 5.01 (d, 2H, N—CH$_2$), 6.61-6.65 (d, 1H, J=15.2Hz, CH=CHCON), 7.17-7.21 (d, 1H, CH=CHCON), 7.37-7.60 (m, 9H, naphthyl and Ph), 7.85-8.01 (m, 3H, naphthyl).

trans-3-(3,4-Dihydro-2H-quinolin-1-ylcarbonyl)acrylic Acid (HOOCCH=CH—CO-tetrahydroquinoline). This compound was synthesized using the above procedure with 1,2,3,4-tetrahydroquinoline as the starting material. $^1$H-NMR (DMSO-d$_6$): 1.99-2.02 (m, 2H, N—CH$_2$—CH$_2$—CH$_2$), 2.73-2.76 (t, 1H, N—CH$_2$—CH$_2$—CH$_2$), 3.86-3.98 (t, 1H, N—CH$_2$—CH$_2$—CH$_2$), 6.78-6.82 (dd, 1H, J=14.8 Hz, CH=CHCON), 7.18-7.22 (m, 4H, quinoline), 7.44-7.48 (d, 1H, J=14.8 Hz, CH=CHCON).

trans-3-(3,4-Dihydro-2H-quinolin-1-ylcarbonyl)acrylic Acid (HOOCCH=CH—CO-tetrahydroisoquinoline). This compound was synthesized using the above procedure with 1,2,3,4-tetrahydroisoquinoline as the starting material. $^1$H-NMR (DMSO-d$_6$): 1.99-2.02 (m, 2H, N—CH$_2$—CH$_2$—CH$_2$), 2.73-2.76 (t, 1H, N—CH$_2$—CH$_2$—CH$_2$), 3.86-3.98 (t, 1H, N—CH$_2$—CH$_2$—CH$_2$), 6.78-6.82 (dd, 1H, J=14.8 Hz, CH=CHCON), 7.18-7.22 (m, 4H, quinoline), 7.44-7.48 (d, 1H, J=14.8 Hz, CH=CHCON).

trans-3-(2,3-Dihydroindol-1-ylcarbonyl)acrylic Acid (HOOC—CH=CH—CO-indoline). This compound was synthesized using the above procedure with indoline as the starting material. $^1$H-NMR (DMSO-d$_6$): 3.55 (t, 2H, N—CH$_2$—CH$_2$), 4.27 (t, 1H, N—CH$_2$—CH$_2$), 6.64-6.67 (dd, 1H, J=15.2 Hz CH=CHCON,), 7.03 (t, 1H, indoline-H), 7.17 (t, 1H, indoline-H), 7.24-7.26 (d, 1H, J=7.2 Hz, indoline-H), 7.28-7.32 (d, 1H, J=15.2 Hz, CH=CHCON), 8.11-8.13 (d, 1H, J=8 Hz, indoline-H).

trans-3-(1,3-Dihydroisoindol-2-ylcarbonyl)acrylic Acid (HOOCCH=CH—CO-isoindoline). This compound was synthesized using the above procedure with isoindoline as the starting material. $^1$H-NMR (DMSO-d$_6$): 4.73 (s, 2H, NCH$_2$), 4.99 (s, 2H, NCH$_2$), 6.63-6.67 (d, 1H, J=15.2 Hz, CH=CHCON), 7.33 (m, 5H, isoindoline and CH=CHCON).

trans-3-(4-Phenyl-5,6-dihydro-2H-pyridin-1-ylcarbonyl) acrylic Acid (HOOCCH=CH—CO—(4-Ph-Py)). This compound was synthesized using the above procedure with 4-phenyl-1,2,3,6-tetrahydropyridine hydrochloride as the starting material. $^1$H-NMR (DMSO-d$_6$): 2.57 (s, 2H, pyridyl-CH$_2$), 3.73-3.76 (t, 2H, pyridyl-CH$_2$), 4.17-4.26 (d, 2H, pyridyl-CH$_2$), 6.14-6.17 (d, 1H, pyridyl CH=), 7.23-7.27 (t, 1H, Ph), 7.31-7.35 (t, 2H, Ph), 7.39-7.48 (m, 3H, CH=CHCON and Ph).

trans-3-(Methyl-(1-methylphenethylcarbamoyl)phenyl-ethylcarbamoyl)acrylic Acid (HOOCCH=CH-Phe(Me)-N(Me)(CH$_2$)$_2$Ph). This compound was synthesized using the above procedure with Phe(Me)-N(Me)(CH$_2$)$_2$Ph as the starting material. $^1$H-NMR (DMSO-d$_6$): 2.73-2.98 (m, 10H, Phe-CH$_2$ and CH$_2$Ph and 2×Me), 3.40-3.51 (m, 2H, N—CH$_2$), 5.20 (m, 1H, α-H), 6.63-5.78 (2×t, 1H, CH=CHCON), 6.80-6.99 (m, 1H, CH=CHCON), 7.10-7.33 (m, 10H, 2×Ph).

Exemplary Methods of Use

Peptide propenoyl hydrazides are irreversible inhibitors for cysteine proteases. Peptide propenoyl hydrazides containing aza-amino acid residues with anionic side chains in the P1 site are excellent inhibitors of caspases. Legumain is inhibited by peptide propenoyl hydrazides with a P1 aza-asparagine residue. Clostripain and gingipain are inhibited by peptide propenoyl hydrazides with P1 basic side chains. These structures may be used in vivo to treat diseases such as cancer and neurodegenerative diseases, which result from the uncontrolled proteolysis by cathepsin B, calpain, caspases, and related cysteine proteases. These inhibitors may be used in vitro to prevent proteolysis, which occurs in the process of production, isolation, purification, storage, or transport of peptides and proteins. These inhibitors may be useful as therapeutic agents for treatment of neurodegeneration, viral infections, muscular dystrophy, myocardial tissue damage, tumor metastasis, and bone resorption.

Enzyme Assays.

Caspase-1. The preparation of the autolytically stable caspase-1 variant used in these studies has been described previously. Briefly, the variant contains a mutation (D381E), which renders it resistant to autolytic inactivation, but has no detectable affect on enzyme activity as compared to the naturally occurring enzyme. The enzyme variant was expressed in E. coli, purified first by immobilized metal chromatography via the N-terminal N-His tag, treated with excess oxidized glutathione to stabilize the reactive thiolate, and then re-purified by size-exclusion chromatography.

Inhibition data was measured using the progress curve assay method. Serial dilutions of each compound were prepared using an initial 8-fold dilution of a DMSO stock into HGE (100 mM HEPES, 20% glycerol v/v, 0.5 mM EDTA), followed by seven serial two-fold dilutions into HGE and 12.5% DMSO, thus maintaining constant DMSO through the dilution series. Ten µL of diluted stocks or of vehicle (HGE and 12.5% DMSO) were placed in triplicate onto a 96-well microtiter plate, allowing several compounds to be tested on each plate. The plate was covered to minimize evaporation, and the plate was pre-warmed to 30° C. for 20 minutes. Enzyme was diluted into 10.0 mL of assay buffer (HGE, 5 mM DTT, plus 15 µM Ac-YVAD-AMC, 2 nM approximate final enzyme concentration), and this activated reaction mixture was added to the plate at 90 μL/well. Progress of substrate hydrolysis was monitored for 900 s in a LabSystems (Needham, Mass.) Fluoroskan Ascent fluorescent platereader using 385 and 460 nm excitation and emission filters, respectively, and a photomultiplier gain setting of 10. Triplicate curves were averaged and fit by nonlinear regression to the equation for irreversible inactivation shown below.

$$F(t) = F_0 + \frac{V_i(1 - e^{-k_{obs}t})}{k_{obs}}$$

where $F_0$ was routinely fixed to zero, since fluorescence values were always adjusted to an origin of 0. The second order rate constant $k_{on}$ ($M^{-1}s^{-1}$) was obtained from the slopes by linear regression, and errors represent the standard deviation of the regression slope.

Enzyme Assays

Caspase-2, -3, -6, -7, -8, -9 and -10. Caspases-2, -3, -6, -7, -8, -9 and -10 were expressed in *E. coli* and purified in Guy Salvesen's laboratory at the Burnham Institute, La Jolla, Calif., according to the methods known in the art. Inhibition rates were determined by the progress curve method known in the art. This method is suitable for measuring irreversible inhibition rates with fast inhibitors, where the inhibitor, the substrate and the enzyme are incubated together and the rate of substrate hydrolysis is measured continuously. The rate of substrate hydrolysis in the presence of the inhibitor was monitored for 20 minutes. The progress curve of inhibition, where the product formation approaches an asymptote is described in the equation $$ln([P_\infty]-[P])=ln[P_\infty]-A[I]t$$

where [P] and [$P_\infty$] are the product concentrations at t and t=∞ respectively, A is the apparent rate constant in the presence of the substrate. The apparent rate constants were determined from the slopes of plots of ln ([$P_\infty$]−[P]) versus time (t) in seconds as previously described, where A=slope/[I].

For competitive and irreversible inhibition, the apparent rate constant is converted to the second order rate constant $k_2$ by taking into consideration the effect of the substrate concentration on the apparent rate constant. The second order rate constant is described as in the equation:

$$k_2=A*(1+[S]/K_M)$$

Assays using the fluorogenic substrates Ac-DEVD-AMC ($\lambda_{ex}$=360 nm, $\lambda_{em}$=465 nm), Z-VDVAD-AFC ($\lambda_{ex}$=430 nm, $\lambda_{em}$=535 nm), and Ac-LEHD-AFC were carried out on a Tecan Spectra Fluor microplate reader at 37° C. The $K_M$ values for Ac-DEVD-AMC with caspase-3 ($K_M$=9.7 μM), caspase-6 ($K_M$=236.35 μM), caspase-7 ($K_M$=23.0 M), caspase-8 ($K_M$=6.79 μM), and caspase-10 ($K_M$=20.2 ,μM) were determined in the laboratory of Guy Salvesen. The $K_M$ value for Ac-LEHD-AFC with caspase-9 ($K_M$=114 μM) was also determined in the laboratory of Guy Salvesen. The KM value for Z-VDVAD-AFC with caspase-2 was found to be 80.5 μM. The $k_2$ values are 2.24-fold higher than the apparent rate for caspase-2 because of the 100 mM [S] and $K_M$=80.5 lM. The $k_2$ values are 11.31-fold higher than the apparent rate for caspase-3 because of the 100 mM [S] and $K_M$=9.7 μM. The $k_2$ values are 1.42-fold higher than the apparent rate for caspase-6 because of the 100 mM [S] and $KM_M$=236.35 μM. The $k_2$ values are 5.35-fold higher than the apparent rate for caspase-7 because of the 100 mM [S] and $K_M$=23.0 μM. The $k_2$ values are 15.73-fold higher than the apparent rate for caspase-8 because of the 100 mM [S] and $K_M$=6.79 FM. The $k_2$ values are 2.32-fold higher than the apparent rate for caspase-9 because of the 150 mM [S] and $K_M$=114 μM. The $k_2$ values are 8.43-fold higher than the apparent rate for caspase-10 because of the 150 mM [S] and $K_M$=20.2 μM.

The concentration of the caspase-3 stock solution was 2 nM in the assay buffer. Assay buffer is a 1:1 mixture of caspase buffer (40 mM Pipes, 200 mM NaCl, 0.2% (w/v) CHAPS, sucrose 20% (w/v)) and 20 mM DTT solution in $H_2O$ at pH 7.2. The concentration of the substrate stock solution was 2 mM in DMSO. The enzyme was pre-activated for 10 min at 37° C. in the assay buffer. The standard 100 μL reaction was started by adding 40 μL of assay buffer, 5 μL of various amounts of inhibitor (stock solution concentrations varied from $5\times10^{-3}$ M to $4.84\times10^{-7}$ M in DMSO), and 5 μL of substrate in DMSO (100 μM final concentration) at 37° C. 50 μL of 2 nM enzyme stock solution (final concentration: 1 nM) was added to the mixture after 1 min and reading started immediately for 20 min at 37° C. Inhibition experiments were repeated in duplicate and standard deviations determined.

Caspase-6 kinetic assays were performed using the same conditions and the same substrate (Ac-DEVD-AMC, 2 mM stock solution in DMSO). The enzyme stock solution was 10 nM (final concentration in the well: 5 nM) in the assay buffer. The inhibitor stock solution concentrations varied from $5\times10^{-3}$ M to $2.42\times10^{-6}$ M in DMSO.

Caspase-7 kinetic assays were performed using the same conditions and the same substrate (Ac-DEVD-AMC, 2 mM stock solution in DMSO). The enzyme stock solution was 10 nM (final concentration in the well: 5 nM) in the assay buffer. The inhibitor stock solution concentrations varied from $5\times10^{-3}$ M to $2.5\times10^{-6}$ M in DMSO.

Caspase-8 kinetic assays were performed using the same conditions and the same substrate (Ac-DEVD-AMC, 2 mM stock solution in DMSO). The enzyme stock solution was 100 nM (final concentration in the well: 50 nM) in the assay buffer. The inhibitor stock solution concentrations varied from $5\times10^{-3}$ M to $2.42\times10^{-6}$ M in DMSO.

Caspase-2 kinetic assays were performed using Z-VD-VAD-AFC as the substrate (2 mM stock solution in DMSO) and with the same conditions as caspase-3. The concentration of the caspase-2 stock solution was 86.7 nM in the assay buffer (final concentration in the well: 43.3 nM). The inhibitor stock solution concentrations varied from $5\times10^{-3}$ M to $1\times10^{-4}$ M in DMSO.

Caspase-9 kinetic assays were performed using Ac-LEHD-AFC as the substrate (3 mM stock solution in DMSO) and with the following conditions. The concentration of the caspase-9 stock solution was 150 mM in the assay buffer (final concentration in the well: 75 nM). Assay buffer is a 1:1 mixture of buffer (200 mM Hepes, 100 mM NaCl, 0.02% (w/v) CHAPS, sucrose 20% (w/v)) and 20 mM DTT solution in $H_2O$ at pH 7.0). The assay buffer was supplemented with 0.7 M sodium citrate. The enzyme was pre-activated for 10 min at 37° C. in the assay buffer. The inhibitor stock solution concentrations varied from $5\times10^{-1}$ M to $2.5\times10^{-5}$ M in DMSO.

Caspase-10 kinetic assays were performed using the same substrate as caspase-3 (Ac-DEVD-AMC, 3 mM stock solution in DMSO) and with the following conditions. The concentration of the caspase-10 stock solution was 50 nM in the assay buffer (final concentration in the well: 25 nM). Assay buffer is a 1:1 mixture of buffer (200 mM Hepes, 0.2% (w/v) CHAPS, PEG 20% (w/v)) and 20 mM DTT solution in $H_2O$ at pH 7.0). The enzyme was pre-activated for 10 min at 25° C.

in the assay buffer. The inhibitor stock solution concentrations varied from $5 \times 10^{-3}$ M to $2.5 \times 10^{-5}$ M in DMSO.

*S. mansoni* Legumain. Assays with legumain were performed as follows. A fluorometric assay for legumain has been described previously. Legumain, purified from pig kidney tissue, was assayed at 30° C. in buffer (39.5 mM citric acid, 121 mM $Na_2HPO_4$ at pH 5.8 containing 1 mM EDTA, 1 mM TCEP, and 0.01% CHAPS) with Cbz-Ala-Ala-Asn-AMC as the substrate (10 µM final concentration). The assays were carried out in a Perkin Elmer LS 3B fluorescence spectrometer ($\lambda_{ex}$=360 nm, $\lambda_{em}$=460 nm) under the control of an IBM-compatible computer running the FLUSYS software. The rate of substrate hydrolysis in the absence of inhibitor was recorded, after which the inhibitor was added in a negligible volume and the new rate was monitored. Rate constants for irreversible inactivation were found by nonlinear regression analysis of the pseudo first-order curves using the FLUSYS software, giving $k_{obs}$. The second-order rate constant $k_2$ was calculated as $k_{obs}/[I]$, at $[S]<K_M$. The test substrates were used at $[S]<K_M$, so no corrections for competition with the inhibitors were required. A minimum of three different concentrations of inhibitor was used to determine second-order rate constants with legumain (range used 100 µM-100 nM).

Studies with the propenoyl hydrazides using the schistosome legumain SmAE, (*Schistosoma mansoni* asparaginyl endopeptidase) were also performed. The enzymatically pure enzyme (zymogen form) was expressed in *Pichia* without interference from other proteases [Caffrey et al, FEBS lett, 466, 244-248 (2000); incorporated herein by reference]. The actual active site enzyme concentration is unknown. The lyophilized enzyme (50-100 mg) was reconstituted in 1.5 mL 0.5 M sodium acetate, pH 4.5 containing 4 mM DTT, and left to stand at 37° C. for 3-4 hours to allow for auto-activation of the zymogen. In a black 96-well microtiter plate, 50 µL of activated enzyme was added to an equal volume of 0.1 M citrate-phosphate buffer pH 6.8 containing 4 mM DTT. Inhibitor stock solutions (20 mM) were prepared in DMSO. Serial dilutions (using water) of inhibitor were added (as 1 µL aliquots) to yield concentrations of between 2 and 0.00002 µM inhibitor. The inhibitors were preincubated with the protease at room temperature for 20 minutes before the assay ($IC_{50}s$ were the same when incubated for only 5 minutes). After incubating various inhibitor concentrations with enzyme, 100 µL of the same buffer containing 20 µM substrate (Cbz-Ala-Ala-Asn-AMC) was added to the wells and the reaction monitored at room temperature with linear kinetics up to 20 minutes. Inhibitors are tested in duplicate. A plot of the RFU/min versus the inhibitor concentration [µM] permitted calculation of an $IC_{50}$ value and estimation of the $k_{obs}/[I]$.

Papain and Cathepsin B. The incubation method was used to measure the irreversible inhibition of papain and cathepsin B. With cathepsin B, 30 µL of a stock inhibitor solution was added to 300 µL of 0.1 M potassium phosphate buffer containing 1.25 mM EDTA, 0.01% Brij 35 at pH 6.0, followed by the addition of 30 µL of a freshly prepared cathepsin B solution (approximate concentration $6.98 \times 10^{-3}$ µg/µL) in the same potassium phosphate buffer containing 1 mM DTT (freshly prepared). Aliquots (50 µL) from the inhibition mixture were withdrawn at various time intervals and added to 200 µL of a 0.1 M potassium phosphate buffer containing 1.25 mM EDTA, 0.01% Brij 35 at pH 6.0, and the substrate Cbz-Arg-Arg-AMC (499 µM). The release of 7-amino-4-methylcoumarin was monitored ($\lambda_{ex}$=360 nm, $\lambda_{em}$=465 nm) using a Tecan Spectra Fluor microplate reader. Pseudo first-order inactivation rate constants were obtained from plots of ln $v_t/v_o$ versus time.

The incubation method was also used for papain. The inhibition incubation buffer for papain was 50 mM Hepes buffer at pH 7.5, containing 2.5 mM DTT and 2.5 mM EDTA. The assay used the substrate Z-Phe-Arg-pNA (53.7 µM) in the same buffer. The approximate concentration of papain added to the incubation buffer was 0.29 mg/mL. The release of p-nitroanilide was monitored at 405 nm with a Molecular Devices Thermomax microplate reader.

Clostripain. Clostripain was purchased from Sigma Chemical Co. (St. Louis, Mo.) as a solid which was dissolved in an activation solution of 8 mM DTT at a concentration of 5.962 µM and stored at −20° C. prior to use. The inhibition of clostripain began with the addition of 25 µL of stock inhibitor solution (concentration varies by inhibitor) in DMSO to a solution of 250 µL of 20 mM Tris/HCl, 10 mM $CaCl_2$, 0.005% Brij 35, 2 mM DTT buffer at pH 7.6 (clostripain buffer) and 5 µL of the stock enzyme solution. Aliquots (25 µL) of this incubation mixture were taken at various time points and added to a solution containing 100 µL of the clostripain buffer and 5 µL of Z-Phe-Arg-AMC substrate solution (0.139 mM) in DMSO. The enzymatic activity was monitored by following the change in fluorescence at 465 nm. All data obtained was processed by pseudo-first order kinetics, Gingipain K. Gingipain K stock solution consisted of a buffer containing 20 mM Bis-Tris, 150 mM NaCl, 5 mM $CaCl_2$, 0.02% $NaN_3$, at pH 8.0 at a concentration of 9 µM, which was stored at −20° C. prior to use. Before using the enzyme, an-aliquot (1 µL) of the stock enzyme was diluted to a concentration of 4.61 nM in 1.951 mL of a solution of 0.2 M Tris/HCl, 0.1 M NaCl, 5 mM $CaCl_2$, 2 mM DTT at pH 8.0 (gingipain K buffer) and kept at 0° C. This solution was used only for one day, as freezing the enzyme at this concentration destroyed all activity. The inhibition of gingipain K began with the addition of 25 µL of stock inhibitor solution (concentration varies by inhibitor) in DMSO to 244 µL of the diluted enzyme solution (4.61 nM) in gingipain K buffer warmed to rt. Aliquots (20 µL) of this were taken at various time points and added to a solution containing 100 µL of the gingipain K buffer and 5 µL of Suc-Ala-Phe-Lys-AMC . TFA as the substrate (0.910 mM stock) in DMSO. The enzymatic activity was monitored by following the change in fluorescence at 465 nm. The data for gingipain K was processed by pseudo-first order kinetics.

Calpain I. Irreversible kinetic assays were performed by the incubation method with calpain I from porcine erythrocytes. Enzymatic activities of calpain I were measured at 23° C. in 50 mM Hepes buffer (pH 7.5) containing 10 mM cysteine and 5 mM $CaCl_2$, using Suc-Leu-Tyr-AMC as the substrate. To 30 µL of an enzyme stock solution (1 mg/mL) of calpain I was added 300 µL of incubation buffer and 30 µL of a stock inhibitor solution in DMSO. At various time intervals 50 µL aliquots were withdrawn from the incubation mixture and added to 200 µL enzyme buffer containing Suc-Leu-Tyr-AMC (1.6 mM). Substrate hydrolysis was monitored using a Tecan Spectra Fluor microplate reader ($\lambda_{ex}$=360 nm, $\lambda_{em}$=465 nm). Pseudo first-order rate constants ($k_{obs}$) were obtained from plots of ln $v_t/v_o$ versus time.

Trypsin. Trypsin was purchased from Sigma Chemical Co. (St. Louis, Mo.) as a solid which was dissolved in a solution of 1 mM HCl at a concentration of 1 µM, kept at 0° C., and used immediately. The trypsin assay was conducted with 224 µL of a solution of 0.1 M Hepes, 0.01 M $CaCl_2$, at pH 7.5 (trypsin buffer), 9 µL of Z-Phe-Arg-AMC substrate solution (1 mM, 2 mM, and 4 mM stocks) in DMSO, 4.2 µL of inhibitor solution (1.25 mM, 2.5 mM, 5 mM, 7.5 mM, and 10 mM for PhPr-Leu-ALys-CH=CH—$CO_2Et$, and 2.5 mM, 5 mM, and 7.5 mM for PhPr-Leu-AOm-CH=CH—CO₂Et) in DMSO, and 4.2 µL of the trypsin stock solution (1 µM) at 23° C. The enzymatic activity was monitored by following the change in fluorescence at 465 nm. The enzymatic assay was followed for 10 min with the 2.5 mM stock inhibitor solution and 1 mM stock substrate solution. The data was processed as a competitive reversible inhibitor by a Dixon plot.

2. Structure-Activity Relationships

Table 1 shows the inhibitory constants ($k_2$) for the inhibition of caspases-2, -3, -6, -7, -8, -9 and -10 by propenoyl hydrazides. The inhibition constants $k_2$ are second-order rate constants and the inhibitors with the higher numbers are more potent.

TABLE 1

Inhibition of Caspases by Aza-Peptide Michael Acceptors

| | $k_2(M^{-1}s^{-1})$ | | | | | | |
|---|---|---|---|---|---|---|---|
| INHIBITOR | Caspase-2[a,d] | Caspase-3[a] | Caspase-6[a] | Caspase-7[a] | Caspase-8[a] | Caspase-9[b] | Caspase-10[c] |
| Cbz-Val-AAsp-CH=CH—CH₃ | ND | NI | NI | ND | NI | ND | ND |
| Cbz-Val-AAsp-CH=CH—CH=CH—CH₃ | NI | NI | NI | 56 ± 4 | NI | NI | NI |
| Cbz-Val-AAsp-CH=CH—CH₂CH₂Ph | ND | NI | NI | ND | NI | ND | ND |
| Cbz-Val-AAsp-CH=CH—Cl | NI | NI | NI | NI | NI | 15 ± 1 | NI |
| Cbz-Val-AAsp-CH=CH-4-Cl—Ph | NI | NI | NI | NI | NI | 19 ± 1 | NI |
| Cbz-Val-AAsp-CH=CH—COOEt | NI | 8,000 | NI | 2,680 ± 60 | NI | 5,240 ± 380 | 389 ± 87 |
| Cbz-Val-AAsp-CH=CH—CONH-nBu | NI | 184 ± 9 | NI | 55 ± 5 | NI | 32 ± 13 | NI |
| Cbz-Val-AAsp-CH=CH—CONHCH₂Ph | NI | 185 | NI | 60 ± 1 | NI | 20 ± 2 | NI |
| Cbz-Glu-Val-AAsp-CH=CH—COOEt | 90 ± 10 | 38,600 ± 4,200 | 3,540 ± 4,200 | 52,400 ± 10,600 | 244,000 ± 30,000 | 32,900 ± 10,250 | 8,940 ± 5,250 |
| Cbz-Asp-Glu-Val-AAsp-CH=CH—COOEt (cis) | 26,200 ± 6,000 | 1,060,000 ± 92,500 | 11,000 ± 515 | 139,000 ± 4,500 | 181,000 ± 13,700 | ND | 13,500 ± 2,300 |
| Cbz-Asp-Glu-Val-AAsp-CH=CH—COOEt (trans) | 2,640 ± 10 | 2,130,000 ± 99,130 | 35,575 ± 0 | 239,000 ± 55,600 | 272,960 ± 18,370 | ND | 49,900 ± 7,000 |
| Cbz-Asp-Glu-Val-AAsp-CH=CH—COOCH₂Ph | ND | 1,700,000 ± 106,000 | 8,470 | 114,000 ± 15,900 | 121,000 ± 13,700 | ND | 28,300 ± 7,700 |
| Cbz-Asp-Glu-Val-AAsp-CH=CH—CONHCH₂Ph | 130 ± 20 | 1,750,000 ± 18,500 | 3,210 ± 105 | 249,000 ± 52,500 | 78,235 ± 8,000 | 2,010 ± 150 | 19,400 ± 400 |
| Cbz-Asp-Glu-Val-AAsp-CH=CH—CONHCH₂-4-F—Ph | 130 ± 20 | 2,100,000 ± 26,400 | 4,400 ± 361 | 329,000 ± 53,300 | 85,100 ± 9,700 | 900 ± 70 | 37,700 ± 2,550 |
| Cbz-Asp-Glu-Val-AAsp-CH=CH—CONHCH₂CH₂Ph | 120 ± 10 | 1,950,000 ± 53,000 | 3,470 ± 52 | 267,000 ± 15,000 | 129,000 ± 27,400 | 655 ± 50 | 31,400 ± 3,600 |
| Cbz-Asp-Glu-Val-AAsp-CH=CH—CON(CH₃)CH₂Ph | 660 ± 240 | 2,640,000 ± 397,000 | 9,500 ± 210 | 275,000 ± 11,300 | 90,300 ± 18,250 | 820 ± 215 | 29,400 ± 830 |
| Cbz-Asp-Glu-Val-AAsp-CH=CH—CON(CH₃)CH₂CH₂Ph | 320 ± 25 | 1,180,000 ± 264,000 | 4,000 ± 413 | 172,000 ± 72,000 | 31,900 ± 2,800 | 425 ± 10 | 9,570 ± 5,240 |
| Cbz-Asp-Glu-Val-AAsp-CH=CH—CON(CH₂Ph)₂ | 110 ± 25 | 3,000,00 ± 80,000 | 5,100 ± 0 | 359,000 ± 8,400 | 8,600 ± 1,600 | 450 ± 30 | 6,300 ± 50 |
| Cbz-Asp-Glu-Val-AAsp-CH=CH—CON(CH₂-1-Napth)₂ | 410 ± 60 | 5,620,000 ± 1,120,000 | 29,700 ± 540 | 875,000 ± 106,000 | 9,460 ± 880 | 150 ± 10 | 32,500 ± 5,250 |
| Cbz-Asp-Glu-Val-AAsp-CH=CH—CON-tetrahydroquinoline | 390 ± 90 | 2,300,000 ± 26,500 | 5,700 ± 0 | 137,000 ± 25,000 | 118,000 ± 14,800 | 340 ± 120 | 8,330 ± 1,400 |
| Cbz-Asp-Glu-Val-AAsp-CH=CH—COPh | 165 ± 85 | 122,000 | 1,800 ± 13 | 10,800 ± 2,000 | 9,720 ± 500 | ND | 930 ± 80 |
| Cbz-Val-Glu-Val-AAsp-CH=CH—COOEt | 115 ± 20 | 41,200 ± 8,600 | 83,600 ± 8,400 | 3,650 ± 1,330 | 175,800 ± 6,800 | 340 ± 120 | 6,600 ± 690 |
| Cbz-Ile-Glu-Thr-AAsp-CH=CH—COOEt | 300 ± 160 | 6,740 ± 1,650 | 88,700 ± 33,700 | 530 ± 10 | 56,500 ± 3,800 | ND | 6,900 ± 250 |
| Cbz-Ile-Glu-Thr-AAsp-CH=CH—COOCH₂Ph | 110 ± 40 | 2,300 ± 77 | 23,350 ± 1,650 | 660 ± 210 | 148,400 | ND | 15,200 ± 2,500 |
| Cbz-Ile-Glu-Thr-AAsp-CH=CH—CONHPh | 365 ± 20 | 7,030 ± 720 | 99,200 ± 10,800 | 920 ± 60 | 245,000 ± 22,800 | 940 ± 275 | 9,210 ± 377 |
| Cbz-Ile-Glu-Thr-AAsp-CH=CH—CONHCH₂Ph | 15 ± 3 | 2,250 ± 560 | 16,800 ± 1,030 | 100 ± 20 | 61,300 ± 2,300 | 440 ± 160 | 503 ± 209 |
| Cbz-Ile-Glu-Thr-AAsp-CH=CH—CONHCH₂CH₂Ph | 30 ± 0 | 4,750 ± 565 | 18,700 ± 1,250 | 440 ± 95 | 71,000 ± 13,700 | 615 ± 160 | 8,290 ± 1,560 |
| Cbz-Ile-Glu-Thr-AAsp-CH=CH—CON(CH₃)CH₂Ph | 95 ± 8 | 6,000 ± 100 | 45,900 ± 5,000 | 390 ± 90 | 59,700 ± 4,500 | 845 ± 190 | 8,500 ± 300 |
| Cbz-Ile-Glu-Thr-AAsp-CH=CH—CON(CH₃)CH₂CH₂Ph | 38 ± 1 | 5,480 ± 26 | ND | 1,020 ± 440 | 60,500 ± 8,000 | 760 ± 335 | 8,770 ± 1,780 |

TABLE 1-continued

Inhibition of Caspases by Aza-Peptide Michael Acceptors

| | $k_2 (M^{-1} s^{-1})$ | | | | | | |
|---|---|---|---|---|---|---|---|
| INHIBITOR | Caspase-2[a,d] | Caspase-3[a] | Caspase-6[a] | Caspase-7[a] | Caspase-8[a] | Caspase-9[b] | Caspase-10[c] |
| Cbz-Ile-Glu-Thr-AAsp-CH=CH—CON(CH$_2$Ph)$_2$ | 76 ± 1 | 9,570 ± 1,230 | 83,900 ± 29,000 | 1,140 ± 210 | 39,500 ± 0 | 1,930 ± 35 | 7,930 ± 2,510 |
| Cbz-Leu-Glu-Thr-AAsp-CH=CH—COOEt | NI | 5,560 ± 290 | 18,700 ± 1,040 | NI | 237,000 ± 52,700 | 37 ± 0 | NI |
| Cbz-Leu-Glu-Thr-AAsp-CH=CH—COOCH$_2$Ph | 480 ± 170 | 4,600 ± 330 | 47,600 ± 2,500 | 1,570 ± 135 | 98,400 ± 9,130 | ND | 18,900 ± 1,580 |
| Cbz-Leu-Glu-Thr-AAsp-CH=CH—CONHPh | 290 ± 150 | 4,700 ± 308 | 11,400 ± 2,060 | 730 ± 200 | 176,000 ± 2,280 | 1,190 ± 230 | 6,050 ± 1,380 |
| Cbz-Leu-Glu-Thr-AAsp-CH=CH—CONHCH$_2$Ph | 66 ± 25 | 1,120 | 1,550 ± 50 | 340 ± 15 | 70,170 ± 13,700 | 1,400 ± 260 | 14,400 ± 1,900 |
| Cbz-Leu-Glu-Thr-AAsp-CH=CH—CONHCH$_2$-4-F—Ph | 70 ± 1 | 4,490 ± 410 | 3,100 ± 465 | 410 ± 60 | 171,000 ± 36,500 | 1,695 ± 30 | 9,380 ± 1,560 |
| Cbz-Leu-Glu-Thr-AAsp-CH=CH—CONHCH$_2$CH$_2$Ph | 110 ± 40 | 5,400 ± 51 | 2,150 ± 52 | 440 ± 60 | 121,000 ± 2,300 | 1,760 ± 190 | 17,900 ± 2,300 |
| Cbz-Leu-Glu-Thr-AAsp-CH=CH—CON(CH$_3$)CH$_2$Ph | 140 ± 25 | 6,000 ± 100 | 10,800 ± 410 | 520 ± 60 | 169,000 | 4,320 ± 930 | 8,430 ± 710 |
| Cbz-Leu-Glu-Thr-AAsp-CH=CH—CON(CH$_3$)CH$_2$CH$_2$Ph | 50 ± 10 | 2,620 ± 26 | 2,550 ± 413 | 290 ± 170 | 65,300 ± 5,700 | 960 ± 30 | 6,190 ± 820 |
| Cbz-Leu-Glu-Thr-AAsp-CH=CH—CON(CH$_2$Ph)$_2$ | 110 ± 10 | 8,630 ± 1,330 | 14,100 ± 1,440 | 760 ± 100 | 129,000 ± 13,700 | 1,105 ± 460 | 8,080 ± 1,660 |
| Cbz-Leu-Glu-Thr-AAsp-CH=CH—CON-tetrahydroquinoline | 92 ± 51 | 12,100 ± 720 | 13,000 ± 1,850 | 540 ± 30 | 216,000 ± 4,600 | 1,660 ± 710 | 9,000 ± 500 |
| Cbz-Leu-Glu-Thr-AAsp-CH=CH—CON(CH$_3$)CH$_2$-1-Napth | 290 ± 110 | 11,200 ± 1,130 | 21,700 ± 206 | 1,100 ± 35 | 179,000 ± 38,800 | 5,030 ± 555 | 13,600 ± 970 |

NI = no inhibition,
ND = not determined,
Cbz = PhCH$_2$—OCO—;
[a]Assay buffer was 20 mM Pipes, 100 mM NaCl, 0.1% (w/v) CHAPS, sucrose 10% (w/v) and 10 mM DTT, at pH 7.2, with Ac-DEVD-AMC as the substrate;
[b]Assay buffer was 100 mM Hepes, 50 mM NaCl, 0.01% (w/v) CHAPS, sucrose 10% (w/v)) and 10 mM DTT, at pH 7.0, with Ac-LEHD-AFC as the substrate. The assay buffer was supplemented with 0.7 M sodium citrate;
[c]100 mM Hepes, 0.1% (w/v) CHAPS, PEG 10% (w/v)) and 10 mM DTT, at pH 7.0, with Ac-DEVD-AMC as the substrate;
[d]Cbz-VDVAD-AFC was used as the substrate.

The propenoyl hydrazides with a P1 aza-Asp residue inhibit caspases-2, -3, -6, -7, -8, -9 and -10 with some $k_2$ values in the order of $10^6$ $M^{-1}S^{-1}$ (Table 1). The DEVD and LETD sequences are optimal sequences for caspase-3 and caspase-8, respectively. The DEVD inhibitors Cbz-Asp-Glu-Val-AAsp-CH=CH—CON(CH$_3$)CH$_2$Ph and Cbz-Asp-Glu-Val-AAsp-CH=CH—COOEt are potent inihibitors of caspase-3 ($k_2$ values in the range of 1,700,000 $M^{-1}s^{-1}$-2,640,000 $M^{-1}s^{-1}$), while the LETD derivatives Cbz-Leu-Glu-Thr-AAsp-CH=CH—COOEt, Cbz-Leu-Glu-Thr-AAsp-CH=CH—COOBzl, and Cbz-Leu-Glu-Thr-AAsp-CH=CH—CON(CH$_3$)Bzl are potent inhibitors of caspases-6 and -8 with $k_2$ values up to 47,600 $M^{-1}s^{-1}$ and 237,000 $M^{-1}s^{-1}$, respectively. The disubstituted amide analog Cbz-Asp-Glu-Val-AAsp-CH=CH—CON(Bzl)$_2$ is the most potent compound for caspase-3 with a $k_2$ value of 3,000,000 $M^{-1}s^{-1}$. It is also the most selective compound among the caspases-3, -6, and -8, where it inhibits caspase-3 588 fold more potently than caspase-6 and 348 fold more potently than caspase-8. Esters seem to work better with caspases-6 and -8. The ethyl ester analogs Cbz-Asp-Glu-Val-AAsp-CH=CH—COOEt and Cbz-Leu-Glu-Thr-AAsp-CH=CH—COOEt are very potent inhibitors of caspase-8 with $k_2$ values of 273,000 $M^{-1}s^{-1}$ and 237,000 $M^{-1}s^{-1}$, respectively. We propose that the ethyl ester group is especially favored in the caspase-8 active site, since the prime site has been observed to be relatively small.

The compounds were tested for their inhibitory potency towards *S. mansoni* legumain. The $IC_{50}$ values are reported in Table 2. An $IC_{50}$ value represents the inhibitory concentration, which achieved 50% inhibition of the enzyme. Therefore a lower $IC_{50}$ value is a characteristic of a more potent inhibitor.

TABLE 2

*S. mansoni* Legumain Inhibition with Peptidyl Propenoyl Hydrazides.

| R = | $IC_{50}$ (nM) | $k_{obs}/[I]$ ($M^{-1}s^{-1}$) |
|---|---|---|
| —COOEt | 31 ± 25 | 17,420 |
| —COOBzl | 38 | |
| —CONEt$_2$ | NI | |
| —CON(nBu)$_2$ | 550 | |
| —CO-Pip | 1,000 | |
| —CONHPh | 700 | |
| —CONHBzl | 1,000 | |
| —COBzl-4-F | 800 | |

TABLE 2-continued

S. mansoni Legumain Inhibition with Peptidyl Propenoyl Hydrazides.

| R = | IC$_{50}$ (nM) | k$_{obs}$/[I] (M$^{-1}$s$^{-1}$) |
|---|---|---|
| —CONHCH$_2$CH$_2$Ph | 600 | |
| —CON(CH$_3$)Ph | 60 | |
| —CON(CH$_3$)Bzl | 55 | |
| —CON(CH$_3$)CH$_2$-1-Napth | 35 | 16,930 |
| —CON(CH$_3$)CH$_2$CH$_2$Ph | 600 | |
| —CON(Bzl)Ph | 70 | |
| —CON(Bzl)$_2$ | 45 | 5,800 |
| —CON(Bzl-4-OMe)Bzl | 90 | |
| —CON(Bzl-4-F)Bzl | 60 | |
| —CON(CH$_2$-2-furyl)$_2$ | 900 | |
| —CON(Bzl)-2-CH$_2$-Napth | 70 | 6,100 |
| —CON(Bzl)-1-CH$_2$-Napth | 62 | 6,180 |
| —CO-tetrahydroquinoline | 70 | |
| —CO-tetrahydroisoquinoline | 200 | |
| —CO-indoline | 70 | |
| —CO-isoindoline | 300 | |
| —CO-(4-Ph-pyridine) | 750 | |
| —CO—MePhe—N(CH$_3$)CH$_2$CH$_2$Ph | 750 | |
| —COPh | NI | |
| —CH=CH—CH$_3$ | NI | |
| -2-furyl | >2,000 | |
| -3-Py | >2,000 | |

NI = No Inhibition

The fumarate benzyl and ethyl esters Cbz-Ala-Ala-AAsn-CH=CH—COOEt, Cbz-Ala-Ala-AAsn-CH=CH—COOBzl, and Biotinyl-Ala-Ala-AAsn-CH=CH—COOEt (IC$_{50}$=10 nM, not shown in table 2) are some of the most potent inhibitors. The monosubstituted amides and the acrylate derivatives show little to no inhibition, which leads us to conclude that the hydrogen bonding network between the inhibitor and the active site is optimal with the carbonyl next to the double bond and without the H-bond donating NH of a monosubstituted amide. The benzoyl acrylate Cbz-Ala-Ala-AAsn-CH=CH—COPh fulfills both of the aforementioned requirements, but does not inhibit legumain. We found that the aromatic fumarate substituents are preferred by the enzyme over the alkyl derivatives (NEt$_2$, N(nBu)$_2$, Pip). The extended aromaticity of the N-methyl-1-methyl naphthyl derivative compared to the N-methyl benzyl amide produced an even lower IC$_{50}$ (35 nM). The dibenzyl amide shows the lowest IC$_{50}$ of the aromatic disubstituted amides (IC$_{50}$=45 nM). The substitution of one of the benzyl rings with an electron donating methoxy or an electron withdrawing fluorine only reduces the potency. Both quinoline and indoline exhibited good potency (IC$_{50}$=70 nM), but poorer in comparison to the dibenzyl amide. The aromatic ring is much less flexible in the indoline and quinoline bicyclic system. The altered orientation of the aromatic ring significantly lowers their potency. Both the 4-plhenyltetrahydropyridine and the amino acid derivative Cbz-Ala-Ala-AAsn-CH=CH—CO-MePhe-N(CH$_3$)CH$_2$CH$_2$Ph did not improve the effectiveness of the warhead. The esters are generally more potent than the amide analogs.

The peptidyl propenoyl hydrazides with an aza-Lys, aza-Arg, or aza-Orn residue at P1 are potent inhibitors of gingipain K, gingipain R, and clostripain (Table 3). The aza-Lys derivative inhibits gingipain K very potently with a k$_2$ value of 3,280,000 M$^{-1}$s$^{-1}$. The aza-Orn derivative is also a very potent inhibitor of gingipain K, but it is much more selective toward gingipain K, since the k$_2$ value with clostripain is only 788 M$^{-1}$s$^{-1}$. Both compounds were also tested for activity toward gingipain R. Both compounds, PhPr-Leu-ALys-CH=CH—COOEt and PhPr-Leu-AOrn-CH=CH—COOEt, inhibit gingipain R weakly with k$_2$ values of 289 M$^{-1}$s$^{-1}$ and 32 M$^{-1}$s$^{-1}$, respectively. However the AArg derivatives with very effective inhibitors of gingipain R, but didn't inhibit ginipain K effectively

TABLE 3

Inhibition of Clostripain and Gingipain K and R by Peptidyl Propenoyl Hydrazides.

| | k$_2$ (M$^{-1}$s$^{-1}$) | | |
|---|---|---|---|
| Inhibitor | Clostripain | Gingipain K | Gingipain R |
| PhPr-Leu-ALys-CH=CH—COOEt | 40,750 | 3,280,000 | 289 |
| PhPr-Leu-ALys-CH=CH—COOCH$_2$Ph | 20,500 | 2,510,00 | 632 |
| PhPr-Leu-ALys-CH=CH—CONHCH$_2$Ph | 1,050 | 236,000 | 20 |
| PhPr-Leu-ALys-CH=CH—CON(Me)CH$_2$Ph | 6,000 | 1,360,000 | 79 |
| PhPr-Leu-ALys-CH=CH—CON(CH$_2$Ph)$_2$ | 20,000 | 2,130,000 | 65 |
| PhPr-Leu-ALys-CH=CH—CON(Bzl)-p-CH$_2$C$_6$H$_4$F | 13,800 | 801,000 | 75 |
| PhPr-Leu-ALys-CH=CH—CON(Me)CH$_2$-1-naphthyl | 639 | 975,000 | 576 |
| PhPr-Leu-ALys-CH=CH—CON(Bzl)CH$_2$-2-naphthyl | 17,500 | 811,000 | 98 |
| PhPr-Leu-ALys-CH=CH—CON(CH$_2$-1-naphthyl)$_2$ | 2,250 | 1,890,000 | 214 |
| PhPr-Leu-ALys-CH=CH—CON(4H-quinoline) | 326 | 252,000 | 73 |
| PhPr-Leu-AOrn-CH=CH—COOEt | 788 | 927,000 | 32 |
| PhPr-Leu-AOrn-CH=CH—CONHCH$_2$Ph | NI | 24,700 | 71 |
| PhPr-Leu-AOrn-CH=CH—CON(CH$_2$Ph)$_2$ | 541 | 61,600 | 541 |
| PhPr-Ala-AOrn-CH=CH—COOEt | NI | 632,000 | 18 |
| PhPr-Leu-AArg-CH=CH—COOEt | 69,600 | 1,580 | |
| PhPr-Leu-AArg-CH=CH—CONHCH$_2$Ph | 287,000 | | 555,000 |
| PhPr-Leu-AArg-CH=CH—CON(CH$_2$Ph)$_2$ | 474,000 | | 804,000 |

(PhPr = 3-phenylpropanoyl)

Propenoyl hydrazides designed with clan CD specific sequences are quite specific and in general do not inhibit clan CA proteases such as papain, cathepsin B, and calpain (Tables 4, 5, and 6). There was usually no reactivity toward papain, cathepsin B and calpain after an incubation period of up to 1 h. The inhibitors show little to no cross reactivity with the other members of clan CD proteases.

TABLE 4

Cross Reactivity of Caspase Inhibitors with Clan CA and Other Clan CD Enzymes

| Inhibitor | $k_2$ ($M^{-1}s^{-1}$) | | | | | |
|---|---|---|---|---|---|---|
| | Cathepsin B | Papain | Calpain | Legumain | Clostripain | Gingipain K |
| Cbz-Asp-Glu-Val-AAsp-trans-CH=CH—COOEt | NI | NI | NI | NI | NI | NI |
| Cbz-Asp-Glu-Val-AAsp-trans-CH=CH—COOBzl | NI | ND | ND | ND | NI | NI |
| Cbz-Asp-Glu-Val-AAsp-trans-CH=CH—CONHBzl | NI | ND | ND | ND | NI | NI |
| Cbz-Leu-Glu-Thr-AAsp-trans-CH=CH—COOEt | <10 | NI | <10 | NI | NI | NI |

NI = No inhibition,
ND = not determined.

TABLE 5

Inhibition of Clan CD, Clan CA Cysteine Proteases and Trypsin by Gingipain and Clostripain Specific Propenoyl Hydrazides.

| Inhibitor | $k_{obs}/[I]$ ($M^{-1}s^{-1}$) | | | | |
|---|---|---|---|---|---|
| | Caspases-3, -6, -8 | Calpain I | Papain | Cathepsin B | Trypsin |
| PhPr-Leu-ALys-CH=CH—COOEt | NI | NI | NI | 9 | 17 |
| PhPr-Leu-AOrn-CH=CH—COOEt | NI | NI | NI | 3 | NI |

TABLE 6

Inhibition of Various Clan CD and Clan CA Cysteine Proteaes by Legumain Specific Propenoyl Hydrazides.

| Inhibitor | $k_{obs}/[I]$ ($M^{-1}s^{-1}$) | | | | |
|---|---|---|---|---|---|
| | Caspases-3, -6, -8 | Calpain I | Papain | Cathepsin B | Gingipain K |
| Cbz-Ala-Ala-AAsn-CH=CH—COOEt | NI | NI | NI | 1 | 6 |
| Cbz-Ala-Ala-AAsn-CH=CH—CON(CH$_3$)Bzl | NI | NI | NI | NI | 1 |
| Cbz-Ala-Ala-AAsn-CH=CH—CON(Bzl)$_2$ | NI | NI | 1 | NI | 2 |
| Cbz-Ala-Ala-AAsn-CH=CH—CO-indoline | NI | NI | NI | NI | 1 |
| Cbz-Ala-Ala-AAsn-CH=CH—CON(CH$_3$)-2-Napth | NI | NI | NI | NI | 6 |
| Cbz-Ala-Ala-AAsn-CH=CH—CONHCH$_2$CH$_2$Ph | NI | NI | 12 | NI | NI |

NI = No Inhibition after 20 minutes of incubation.

The peptidyl propenoyl hydrazides are generally poor with clan CA cysteine proteases, such as papain, calpain, or cathepsin B. However, a select few do show limited inhibition with papain, calpain, and cathepsin B. For example the caspase specific inhibitor Cbz-Leu-Glu-Thr-AAsp-trans-CH=CH—COOEt inhibits calpain and cathepsin B with a $k_2$ of <10 $M^{-1}s^{-1}$, the legumain specific inhibitor Cbz-Ala-Ala-AAsn-CH=CH—CONHCH$_2$CH$_2$Ph inhibits papain (12 $M^{-1}s^{-1}$). The gingipain specific inhibitor PhPr-Leu-ALys-CH=CH—COOEt inhibits cathepsin B (9 $M^{-1}s^{-1}$) and the serine protease trypsin (17 $M^{-1}s^{-1}$).

Inhibition Mechanism

The active site of cysteine proteases contains a cysteine and a histidine residue. The proposed mechanism involves the attack of the active site cysteine residue on the double bond to form a covalent adduct. An example of a caspase inhibitor is shown in the following figure. The enzyme recognizes the P1 AAsp residue and inhibition occurs. Additional interactions would occur between the extended substrate binding site of the cysteine protease and the inhibitor, which would increase the binding affinity and specificity of the inhibitors.

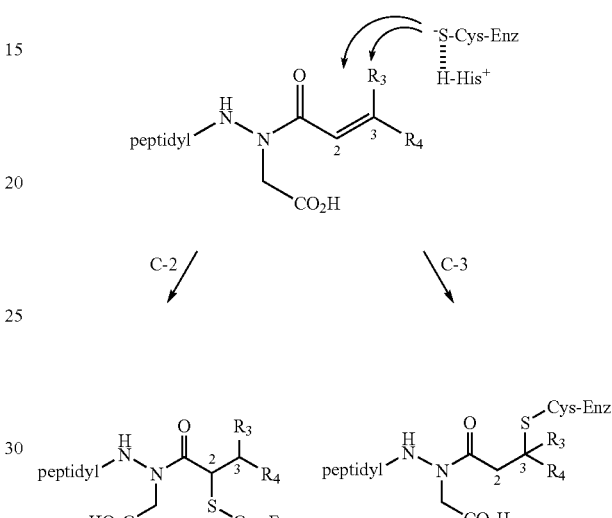

The peptide and amino acid propenoyl hydrazide derivatives, as shown above, bind to the enzymes using many of the interactions that are found in complexes of a particular enzyme with its substrates and/or inhibitors. Additional interactions with the enzyme can be obtained by tailoring the $R_3$ or $R_4$ groups of the inhibitor to imitate the amino acid residues, which are preferred by an individual protease at the S1' and S2' subsites. For example, peptidyl propenoyl hydrazides with $R_3$ phenylalkyl groups would interact effectively with caspase-1, which is shown to prefer such structures in alpha-ketoamide peptide inhibitors. Likewise, the $M_1$ group can interact with the S subsites of the target cysteine protease. Once a good inhibitor structure for a particular enzyme is found, it is then possible to change other characteristics such as solubility or hydrophobicity by adding substituents to the $M_1$ or $R_1$, $R_2$, $R_3$, and $R_4$ groups.

The following structures are inhibitors for the listed enzymes. The inhibitor sequences were obtained from peptide substrate and/or inhibitor seqences in the protease literature.

Cl—$C_6H_4CH_2$OCO-Phe-AGly-CH=CH—COOH for papain
$C_6H_5CH_2$NHCO-Gly-Phe-AGly-CH=CH—COOH for cathepsin B
Morpholine-CO-2-Napth-AHph-CH=CH—COOEt for cathepsin S
2-Napth-$SO_2$-Ile-ATrp-CH=CH—COOH for cathepsin B
1-Napth-$SO_2$-Val-ATrp-CH=CH—COOH for cathepsin B and L
Pro-Phe-AArg-CH=CH—COOH for cathepsin B and L
Cbz-Phe-Leu-Leu-AMet($O_2$)—CH=CH—COOH for cathepsin K
Ph-$CH_2$—$SO_2$-AAsp-CH=CH—$COOCH_2$Ph for caspase-1
Ph-$CH_2$CHFCO-Val-Ala-AAsp-CH=CH—$COOCH_2$Ph for caspase-1
4-Cl-$PhCH_2CH_2$CO-Val-Ala-AAsp-CH=CH—$COOCH_2$Ph for caspase-1
4-$NO_2$-$PhCH_2CH_2$CO-Val-Ala-AAsp-CH=CH—$COOCH_2$Ph for caspase-1
4-$CH_3$O-$PhCH_2CH_2$CO-Val-Ala-AAsp-CH=CH—$COOCH_2$Ph for caspase-1
3-F-$PhCH_2CH_2$CO-Val-Ala-AAsp-CH=CH—$COOCH_2$Ph for caspase-1
3,4-dichloro-$PhCH_2CH_2$CO-Val-Ala-AAsp-CH=CH-$COOCH_2$Ph for caspase-1
Napth-$CH_2$OCO-Val-Ala-AAsp-CH=CH—$COOCH_2$Ph for caspase-1
4-$CF_3$-$PhCH_2CH_2$CO-Val-Ala-AAsp-CH=CH—$COOCH_2$Ph for caspase-1
4-$CH_3$-$PhCH_2CH_2$CO-Val-Ala-AAsp-CH=CH—$COOCH_2$Ph for caspase-1
$PhCH_2$NHCO-Val-Ala-AAsp-CH=CH—$COOCH_2$Ph for caspase-1
4-HO-$PhCH_2CH_2$CO-Val-Ala-AAsp-CH=CH—$COOCH_2$Ph for caspase-1
4-Cl-Ph-$CH_2$OCO-Leu-Glu-Thr-AAsp-CH=CH—CON$(Bzl)_2$ for caspase-3
4-Cl-Ph-$CH_2$OCO-Ile-Glu-Thr-AAsp-CH=CH—CON$(Bzl)_2$ for caspase-3
4-Cl-Ph-$CH_2$OCO-Asp-Glu-Val-AAsp-CH=CH—CON$(Bzl)_2$ for caspase-3
Biotinyl-Asp-Glu-Val-AAsp-CH=CH—COOEt for caspase-3
$C_5H_9$-OCO-Asp-Glu-Val-AAsp-CH=CH—COOEt for caspase-3
3-F-Ph-$CH_2$OCO-Ala-Ala-AAsn-CH=CH—COOEt for legumain
4-PhO-$PhCH_2$OCO-Ala-Ala-AAsn-CH=CH—COOEt for legumain
Biotinyl-Ala-Ala-AAsn-CH=CH—CON$(Bzl)_2$ for legumain
3-F-Ph-$CH_2$OCO-Leu-Glu-Thr-AAsp-CH=CH—COOEt for caspase-6
$PhCH_2CH_2$CO-Val-Ala-AAsp-CH=CH—COO$(CH_2)_2$Ph-4-Cl for caspase-1
Cbz-Leu-Glu-Thr-AAsp-CH=CH—COO$(CH_2)_2$Ph-4-$CH_3$ for caspase-8
Cbz-Leu-Glu-Thr-AAsp-CH=CH—$COOCH_2C_6H_{11}$ for caspase-8
Cbz-Asp-Glu-Val-AAsp-CH=CH—COO$(CH_2)_2C_6H_4$-p-$OCH_3$ for caspase-3
Cbz-Asp-Glu-Val-AAsp-CH=CH—CO-Phe-OBzl for caspase-3
Cbz-Asp-Glu-Val-AAsp-CH=CH—CO-Pyr for caspase-3
Cbz-Ala-Ala-AAsn-CH=CH—COO$(CH_2)_2$-2-Napth for legumain
$PhCH_2CH_2$CO-Val-Ala-AAsp-CH=CH—$(CH_2)_2$Ph-3-F for caspase-1
$PhCH_2CH_2$CO-Val-Ala-AAsp-CH=CH—COO$(CH_2)_2$-2-Napth for caspase-1
Cbz-Leu-Glu-Thr-AAsp-CH=CH—COO$(CH_2)_2C_6H_4$-p-$NO_2$ for caspase-6
Cbz-Ala-Ala-AAsn-CH=CH—COO$(CH_2)_2C_6H_4$-p-CN for legumain
$PhCH_2CH_2$CO-Val-Ala-AAsp-CH=CH—COO$(CH_2)_2C_6H_4$-m-OPh for caspase-1
2,4-dinitrophenyl-Ahx-Gly-Phe-AAla-CH=CH—COOH for cathepsin L
Cbz-Leu-ALys-CH=CH—CON$(Bzl)_2$ for gingipain
Cbz-Leu-AOrn-CH=CH—CON$(Bzl)_2$ for gingipain
Cbz-Leu-ALys-CH=CH—CON$(Bzl)_2$ for clostripain
Cbz-Leu-AOrn-CH=CH—CON$(Bzl)_2$ for clostripain
Cbz-Leu-ALys-CH=CH—CO-Phe-OBzl for gingipain
Cbz-ALys-CH=CH—COOEt for gingipain
Cbz-AOrn-CH=CH—CON$(Bzl)_2$ for clostripain
Cbz-Lys(Biotinyl)-Val-Ala-AAsp-CH=CH—COOEt for caspase-1
Cbz-Leu-ALys-CH=CCl—CON$(Bzl)_2$ for clostripain
Cbz-Leu-AOrn-CH=CCl—CON$(Bzl)_2$ for clostripain
Cbz-Asp-Glu-Val-AAsp-CH=CF—CO—N$(Bzl)_2$ for caspase-3
Cbz-Ala-Ala-AAsn-CH=CF—CO—N$(Bzl)_2$ for legumain
Cbz-Glu-Ala-Gly-AArg-CH=CH—CO—N$(Bzl)_2$ for separase 2. In Vitro Uses.

To use the above inhibitors in vitro, they are dissolved in an organic solvent such as dimethylsulfoxide or ethanol, and are added to an aqueous solution containing serine and/or cysteine proteases. The final concentration of the organic solvent should be less than 25%. The inhibitors may also be added as solids or in suspension. The cysteine protease inhibitors of this disclosure would be useful in a variety of experimental procedures where proteolysis is a significant problem. Inclusion of these inhibitors in radioimmunoassay experiments would result in higher sensitivity. The use of these inhibitors in plasma fractionation procedures would result in higher yields of valuable plasma proteins and would make purification of the proteins easier. The inhibitors disclosed here could be used in cloning experiments utilizing bacterial cultures, yeast, and human cells to produce a purified cloned product in higher yield.

The novel compounds of this disclosure are effective in the prevention of unnecessary proteolysis caused by cysteine proteases in the process of purification, transport and storage of peptides and proteins as shown in Table 1-3 by effective inhibition of many cysteine proteases.

Diagnostic Reagents

Propenoyl hydrazides of the present disclosure can be used for the identification of proteases, for example novel cysteine proteases. One embodiment provides a method for screening a sample for the presence of a protease, particularly a cysteine protease, by contacting the sample with a propenoyl hydrazide, for example a propenoyl hydrazide of Formula I, and detecting the presence of the the propenoyl hydrazide-protease conjugate. Detection of the conjugate may be accomplished using known techniques. For example, propenoyl hydrazides of the present disclosure can be modified with a detectable label including but not limited to a radioisotope, fluorescent marker, biotin, antibody, enzyme conjugate such as horseradish peroxidase, or the like. The azapeptide conjugates can be fixed to a support, for example using known chemical fixatives, and a sample can then by added to the propenoyl hydrazide. Such support can be microarrays or the like. The fixed propenoyl hydrazide can then irreversible or reversibly bind a protease, for example a cysteine protease, in the sample. The support can be washed to remove excess sample. The propenoyl hydrazide-protease conjugate can then be eluted from the support and the protease can be detected or identified using conventional techniques. The support can be any durable substance including but not limited to metal, plastic, glass, quartz or the like. The propenoyl hydrazides can be linked to the support with a linker, for example a cleavable linker to facilliate the removal of propenoyl hydrazide-protease conjugates.

3. In Vivo Uses.

Effective inhibitors of the proteolytic function of caspases (Table 1) can be used to treat a variety of diseases. Excessive cell death can result from acquired or genetic conditions, which increase the accumulation of signals that induce apoptosis or that diminish the threshold at which such events induce apoptosis. Excessive apoptosis has been associated with a variety of disease states including neurodegenerative disorders, ischemic injuries, acquired immunodeficiency syndrome (AIDS), and osteoporosis. Apoptosis is involved in amyotrophic lateral sclerosis (ALS), Huntington's disease, Alzheimer's disease, Parkinson's disease, and spinal muscular atrophy. In multiple sclerosis (MS), the death of the oligodendrocytes is an important example of the glial degeneration through apoptosis.

Huntington, the first protein identified as a caspase substrate that is specifically involved in a neurodegenerative disease, is a substrate for proteolytic cleavage by caspase-3. Thus, propenoyl hydrazides would be useful for the treatment of Huntington's disease and other neurodegenerative diseases such as dentatorubropallidoluysian atrophy (DRPLA), spinocerebellar atrophy type 3 (SCA-3), and spinal bulbar muscular atrophy (SBMA).

Effector caspases cleave Alzheimer's gene products, presenilins 1 and 2 proteins. Recently, it has been shown that caspase-6 is involved in human neuronal cell apoptosis, amyloidogenesis, and Alzheimer's disease. Amyloid β peptide (Aβ), which builds up in the brains of people with Alzheimer's disease, causes cultured neurons to die by apoptosis. Thus effective caspase-6 propenoyl hydrazide inhibitors (Table 1) can be used for the treatment of Alzheimer's disease.

In models related to Parkinson disease, peptide caspase inhibitors protect against 1-methyl-4-phenylpyridinium (MPP$^+$)-induced apoptosis of cultured cerebellar granular neurons and increase the rate of survival. Also, in mice overexpressing Bcl-2, dopaminergic 1-methyl-4-phenyl-1,2,3,6-tetrahydropyridine (MPTP) caspase activity is blocked, toxicity is decreased, and substantial nigra neurons survive. Thus, effective caspase propenoyl hydrazide inhibitors (Table 1) can be used for the treatment of Parkinson's disease.

Neuronal apoptosis is also seen after acute injuries such as stroke, trauma, and ischemia. Apoptosis has been observed in striatal and cortical neurons in animal models of stroke. Transgenic mice, expressing a caspase-1 inhibitor, are protected from ischemic damage after middle cerebral artery occlusion. During ischemia, activated caspases dismantle the cell by cleaving multiple substrates such as the enzymes essential for cell repair and cytoskeletal proteins. Therefore, caspase activation develops in models of global ischemia and may accompany the ischemic component of head injury. The effect of irreversible inhibitors (Z-VAD-FMK, Z-DEVD-FMK, and YVAD-CMK) on ischemia-induced tissue shows that caspase-1 and caspase-3 are involved in the mechanism of cell death in ischemic and excitotoxic brain injury. Caspases are recognized as novel therapeutic targets for central nervous diseases in which cell death occurs mainly by the mechanism of apoptosis. Thus effective caspase propenoyl hydrazide inhibitors (Table 1) can be used for the treatment of many diseases involving apoptosis.

Legumain is involved in Schistosomiasis (blood flukes) and in immune disorders. Thus, legumain inhibitors can be used to treat Schistosomiasis and many immunological problems: Gingipain is involved in periodontal disease and thus gingipain inhibitors can be use to treat periodontal disease. Clostripain inhibitors should be useful as antibacterial agents. Separase inhibitors can be used to treat diseases, which involve cell mitosis.

4. Drug Delivery.

This disclosure also provides a pharmaceutical composition, which comprises a compound according to Formula I and a pharmaceutically accepted carrier, diluent or excipient. Accordingly, the compounds of Formula I may be used in the manufacture of a medicament. For therapeutic use, the peptide propenoyl hydrazides may be administered orally, topically, or parenterally. The term parenteral, as used, includes subcutaneous injection, intravenous, intramuscular, intrastemal injection, or infusion techniques. The dosage depends primarily on the specific formulation and on the object of the therapy or prophylaxis. The amount of the individual doses as well as the administration is best determined by individually assessing each case.

The pharmaceutical compositions containing the active ingredient may be in a form suitable for oral use, for example, as tablets, troches, lozenges, aqueous or oily suspensions, dispersible powders or granules, emulsions, hard or soft capsules, syrups, or elixirs. Dosage levels of the order of 0.2 mg to 140 mg per kilogram of body weight per day are useful in the treatment of the above-indicated conditions (10 mg to 7 gms per patient per day). The amount of active ingredient that may be combined with carrier materials to produce a single dosage form will vary depending upon the host treated and the particular mode of administration.

For injection, the therapeutic amount of the peptide propenoyl hydrazides or their pharmaceutically acceptable salts will normally be in the dosage range from 0.2 to 140 mg/kg of body weight. Administration is made by intravenous, intramuscular, or subcutaneous injection. Accordingly, pharmaceutical compositions for parenteral administration will contain from about 10 mg to 7 gms of the compounds per dose. In addition to the active ingredient, these pharmaceutical compositions will usually contain a buffer, e.g. a phosphate buffer, which keeps the pH in the range from 3.5 to 7 and sodium chloride, mannitol, or sorbitol for adjusting the isotonic pressure.

A composition for topical application can be formulated as an aqueous solution, lotion, jelly or an oily solution or suspension. A composition in the form of an aqueous solution is obtained by dissolving the compounds of this disclosure in aqueous buffer solution of pH 4 to 6.5 and, if desired, adding a polymeric binder. An oily formulation for topical application is obtained by suspending the compounds of this disclosure in an oil, optionally with the addition of a swelling agent such as aluminium stearate and/or a surfactant.

EXAMPLES

The following detailed examples are given to illustrate the disclosure and are not intended to limit it in any manner.

Example 1

General Procedure for the Preparation of Propenoyl Hydrazides.

Mixed Anhydride Coupling Method. Coupling of some of the bulky peptides, such as Cbz-Asp(O-tBu)-Glu(O-tBu)-Val-NHNHCH$_2$COO-tBu and Cbz-Leu-Glu(O-tBu)-Thr-NHNHCH$_2$COO-tBu, with the monoethyl fumarate, was accomplished using the mixed anhydride coupling method. To a solution of the monoethyl fumarate (5 eq) in DMF at 0° C. was added N-methylmorpholine (NMM, 5 eq) followed by isobutyl chloroformate (iBCF, 5 eq). After the reaction mixture was allowed to stir for 30 min, the substituted hydrazide (1 eq) dissolved in DMF, was added to the mixture. After 10 min the ice bath was removed and the reaction mixture was stirred for 16 hours at room temperature. The DMF was evaporated and the residue was washed and purified using the same procedure as described above for the EDC/HOBt coupling method. MS and $^1$H NMR (DMSO-d$_6$, CDCl$_3$ or acetone-d$_6$) were consistent with the proposed structures.

Example 1A

Cbz-Glu(O-tBu)-Val-AAsp(O-tBu)-CH=CH—COOEt was obtained using the mixed anhydride method and was purified using column chromatography on silica gel using 1:9:10 MeOH:CH$_2$Cl$_2$:EtOAc as the eluent, white solid, yield 49%. $^1$H NMR (DMSO-d$_6$): 0.90 (m, 6H, Val), 1.20 (t, 3H, OCH$_2$CH$_3$), 1.41 (m, 18H, tBu), 1.60-2.00 (m, 3H, Val, Glu), 2.21 (m, 2H, Glu), (m, 4H, NCH$_2$COOH, and OCH$_2$CH$_3$), 4.20-4.40 (m, 2H, α-H), 5.05 (m, 2H, Cbz), 7.10 (—CO—CH=CH—COOEt), 7.20-7.40 (m, 5H, Ph), 8.00 (m, 2H, NH). ESI (M+1) Calcd. for C$_{34}$H$_{51}$N$_4$O$_{11}$: 691.35. Observed m/z 691.30.

Example 2

The EDC/HOBt Coupling Method. Cbz-Val-AAsp(O-tBu)-CH=CH—COOEt. To a stirred solution of Cbz-Val-NHNHCH$_2$COOtBu (0.34 mmol, 1 eq), HOBt (0.37 mmol, 1.1 eq), and monoethyl fumarate (0.37 mmol, 1.1 eq) in DMF was added EDC (0.37 mmol, 1.1 eq) and the mixture was allowed to react for 16 h at room temperature (2 eq of EDC/HOBt were used with the tetrapeptides). The DMF was removed under vacuum and the residue was treated with 10 mL EtOAc. The organic layer was then washed with 2×10 mL 2% citric acid, 1×15 mL saturated NaHCO$_3$, and 2×10 mL brine. The organic layer was dried over Na$_2$SO$_4$, filtered and concentrated. Column chromatography on silica gel with 1:49:50 MeOH:CH$_2$Cl$_2$:EtOAc as the eluent gave the product as a white solid with 63% yield. MS and $^1$H NMR (DMSO-d$_6$) were consistent with the proposed structure. MS (ESI) m/z 506.3 [(M+1)$^+$]. $^1$H NMR (CDCl$_3$): 0.97-1.02 (dd, 6H, Val), 1.28 (t, 3H, OCH$_2$CH$_3$), 1.46 (s, 9H, tBu), 2.18 (m, 1H, Val), 3.98 (t, 1H, α-H), 4.21 (q, 2H, OCH$_2$CH$_3$), 5.11 (s, 2H, Cbz), 5.21 (d, 1H, NH), 6.86 (d, 1H, db), 7.33 (s, 6H, Ph and db), 8.49 (s, 1H, NH—N).

Example 2A

Cbz-Val-AAsp(O-tBu)-CH=CHCH$_3$ was obtained by the EDC/HOBt coupling method, and purified by column chromatography on silica gel with 0.5:49.5:50 MeOH:CH$_2$Cl$_2$:EtOAc as the eluent; white solid, yield 53%. MS (ESI) m/z 448.4 [(M+1)$^+$]. $^1$H NMR (DMSO-d$_6$): 0.85-0.89 (dd, 6H, Val), 1.39 (s, 9H, tBu), 1.94 (m, 1H, Val), 3.83 (t, 1H, α-H), 5.02 (q, 2H, Cbz), 6.41 (m, 1H, db), 6.72 (m, 1H, db), 7.32 (s, 5H, Ph), 7.58 (d, 1H, NH).

Example 2B

Cbz-Val-AAsp(O-tBu)-CH=CH—CH=CH—CH$_3$ was obtained by the EDC/HOBt coupling method, and purified by column chromatography on silica gel with 0.5:49.5:50 MeOH:CH$_2$Cl$_2$:EtOAc as the eluent; white solid, yield 8%. MS (ESI) m/z 474.3 [(M+1)$^+$]. $^1$H NMR (DMSO-d$_6$): 0.83-0.89 (dd, 6H, Val), 1.39 (s, 9H, tBu), 1.75 (d, 3H, CH$_3$), 1.92 (m, 1H, Val), 3.83 (t, 1H, α-H), 5.02 (q, 2H, Cbz), 6.14 (m, 2H, db), 6.40 (m, 1H, db), 7.09 (m, 1H, db), 7.33 (s, 5H, Ph), 7.58 (d, 1H, NH), 10.77 (s, 1H, NH—N).

Example 2C

Cbz-Val-AAsp(O-tBu)-CH=CHCH$_2$CH$_2$Ph was obtained by the EDC/HOBt coupling method, and purified by column chromatography on silica gel with 0.5:49.5:50 MeOH:CH$_2$Cl$_2$:EtOAc as the eluent; white solid, yield 53%. MS (ESI) m/z 538.3 [(M+1)$^+$].

Example 2D

Cbz-Val-AAsp(O-tBu)-cis-CH=CH—Cl was obtained by the EDC/HOBt coupling method, and purified by column chromatography on silica gel with 0.5:49.5:50 MeOH:CH$_2$Cl$_2$:EtOAc as the eluent; white solid, yield 25%. MS (ESI) m/z 468.4 [(M+1)$^+$]. $^1$H NMR (DMSO-d$_6$): 0.89 (d, 6H, Val), 1.43 (s, 9H, tBu), 1.95 (m, 1H, Val), 3.84 (t, 1H, α-H), 5.04 (s, 2H, Cbz), 6.59 (s, 1H, db), 6.81 (d, 1H, db), 7.35 (s, 5H, Ph), 7.56 (d, 1H, NH), 10.81 (s, 1H, NH—N).

Example 2E

Cbz-Val-AAsp(O-tBu)-CH=CH-Ph-4-Cl was obtained by the EDC/HOBt coupling method, and purified by column chromatography on silica gel with 0.5:49.5:50 MeOH:CH$_2$Cl$_2$:EtOAc as the eluent; white solid, yield 62%. MS (ESI) m/z 544.3 [(M+1)$^+$]. $^1$H NMR (DMSO-d$_6$): 0.86-0.93 (dd, 6H, Val), 1.41 (s, 9H, tBu), 1.98 (m, 1H, Val), 3.80 (t, 1H, α-H), 5.03 (q, 2H, Cbz), 7.30 (s, 5H, Ph), 7.40 (d, 1H, db), 7.52 (d, 1H, db), 7.76 (m, 4H, Ph-Cl), 10.95 (s, 1 H, NH—N).

Example 2F

Cbz-Val-AAsp(O-tBu)-CH=CH—CONH-nBu was obtained by the EDC/HOBt coupling method, and purified by column chromatography on silica gel with 1:9:10 MeOH:CH$_2$Cl$_2$:EtOAc as the eluent; white solid, yield 53%. MS (ESI) m/z 533.2 [(M+1)$^+$]. $^1$H NMR (DMSO-d$_6$): 0.83-0.87 (m, 9H, Val and NHCH$_2$CH$_2$CH$_2$CH$_3$), 1.27 (m, 2H, NHCH$_2$CH$_2$CH$_2$CH$_3$), 1.41 (s, 11H, tBu and NHCH$_2$CH$_2$CH$_2$CH$_3$), 1.96 (m, 1H, Val), 3.12 (dd, 2H, NHCH$_2$CH$_2$CH$_2$CH$_3$), 3.90 (t, 1H, α-H), 5.03 (q, 2H, Cbz), 6.91 (d, 1H, db), 7.08 (d, 1H, db), 7.28-7.34 (m, 5H, Ph), 7.47 (d, 1H, NH), 8.37 (t, 1H, NHCH$_2$CH$_2$CH$_3$), 10.93 (s, 1H, NH—N).

Example 2G

Cbz-Asp(O-tBu)-Glu(O-tBu)-Val-AAsp(O-tBu)-trans-CH=CH—COOEt was obtained using the EDC/HOBt coupling method from monoethyl fumarate, purified by column chromatography on silica gel with 50:45:5 CH$_2$Cl$_2$:EtOAc:MeOH as the eluent; white solid, yield 68%. $^1$H NMR (CDCl$_3$): 1.00 (d, 6H, Val CH$_3$), 1.29 (t, 3H, OEt), 1.45 (s, 27H, t-Bu), 1.90 (m, 1H, Val CH), 2.10 (d of m, 2H, Glu CH$_2$), 2.40 (d of m, 2H, Glu CH$_2$), 2.80 (d of m, 2H, Asp CH$_2$), 3.20 (s, 2H, AAsp CH$_2$), 4.19 (q, 3H, OEt and α-H), 4.30 (b, 1H, α-H), 4.45 (b, 1H, α-H), 5.12 (q, 2H, Cbz), 6.05 (d, 1H, NH), 6.81 and 7.20 (d of d, 2H, CH=CH), 7.33 (m, 6H, Ph and NH), 7.90 (d, 1H, NH), 9.00 (s, 1H, NH).

Example 2H

Cbz-Asp(O-tBu)-Glu(O-tBu)-Val-AAsp(O-tBu)-cis-CH=CH—COOEt was obtained using the EDC/HOBt coupling method from monoethyl maleate, purified by column chromatography on silica gel with 1:19:20 MeOH:CH$_2$Cl$_2$:EtOAc as the eluent; white solid, yield 53%. MS (ESI) m/z 862.5 [(M+1)$^+$]. $^1$H NMR (DMSO-d$_6$): 0.85 (d, 6H, Val), 1.18 (t, 3H, OCH$_2$CH$_3$), 1.33-1.39 (m, 27H, tBu), 1.74 (m, 1H, Glu), 1.86 (m, 1H, Glu), 1.95 (m, 1H, Val), 2.18 (m, 2H, Glu), 2.45 (dd, 1H, Asp), 2.61 (dd, 1H, Asp), 4.09 (t, 1H, α-H), 4.16 (q, 2H OCH$_2$CH$_3$), 4.33 (m, 2H, α-H), 5.01 (q, 2H, Cbz), 6.61 (d, 1H, db), 7.25 (d, 1H, db), 7.33 (s, 5H, Ph), 7.62 (d, 1H, NH), 7.93 (t, 2H, NH), 11.05 (s, 1H, NH—N).

Example 2I

Cbz-Asp(O-tBu)-Glu(O-tBu)-Val-AAsp(O-tBu)-CH=CH—COOCH$_2$Ph was obtained by the EDC/HOBt coupling method, and purified by column chromatography on silica gel with 1:499:500 MeOH:CH$_2$Cl$_2$:EtOAc as the eluent; white solid, yield 49%. MS (ESI) m/z 924.5 [(M+1)$^+$]. $^1$H NMR (DMSO-d$_6$): 0.80 (t, 6H, Val), 1.35-1.41 (m, 27H, tBu), 1.75 (m, 1H, Glu), 1.84 (m, 1H, Glu), 1.94 (m, 1H, Val), 2.17 (m, 2H, Glu), 2.45 (dd, 1H, Asp), 2.60 (dd, 1H, Asp), 4.13 (t, 1H, α-H), 4.28-4.35 (dm, 2H, α-H), 5.02 (q, 2H, Cbz), 5.19 (s, 2H, Bzl), 6.70 (d, 1H, db), 7.25-7.37 (m, 11H, Ph and db), 7.57 (d, 1H, NH), 7.92 (d, 1H, NH), 7.98 (d, 1H, NH), 11.02 (s, 1H, NH—N).

Example 2J

Cbz-Asp(O-tBu)-Glu(O-tBu)-Val-AAsp(O-tBu)-CH=CH—CONHCH$_2$Ph was obtained by the EDC/HOBt coupling method, and purified by column chromatography on silica gel with 1:9:10 MeOH:CH$_2$Cl$_2$:EtOAc as the eluent; white solid, yield 49%. MS (ESI) m/z 923.5 [(M+1)$^+$]. $^1$H NMR (DMSO-d$_6$): 0.85 (t, 6H, Val), 1.35-1.41 (m, 27H, tBu), 1.72 (m, 1H, Glu), 1.84 (m, 1H, Glu), 1.96 (m, 1H, Val), 2.17 (m, 2H, Glu), 2.44 (dd, 1H, Asp), 2.60 (dd, 1H, Asp), 4.17 (t, 1H, α-H), 4.28 (m, 2H, α-H), 4.36 (d, 2H, NHCH$_2$Ph), 5.02 (q, 2H, Cbz), 6.95 (d, 1H, db), 7.12 (d, 1H, db), 7.22-7.31 (m, 10H, Ph), 7.57 (d, 1H, NH), 7.94 (d, 1H, NH), 8.92 (t, 1H, NHCH$_2$Ph), 10.96 (s, 1H, NH—N).

Example 2K

Cbz-Asp(O-tBu)-Glu(O-tBu)-Val-AAsp(O-tBu)-CH=CH—CONHCH$_2$CH$_2$Ph was obtained by the EDC/HOBt coupling method, and purified by column chromatography on silica gel with 1:9:5 MeOH:CH$_2$Cl$_2$:EtOAc as the eluent, and then rechromatographed using 1:1 EtOAc:CH$_2$Cl$_2$ as the eluent; white solid, yield 29%. MS (ESI) m/z 937.5 [(M+1)$^+$]. $^1$H NMR (DMSO-d$_6$): 0.85 (t, 6H, Val), 1.35-1.41 (m, 27H, tBu), 1.72 (m, 1H, Glu), 1.86 (m, 1H, Glu), 2.00 (m, 1H, Val), 2.17 (m, 2H, Glu), 2.43 (dd, 1H, Asp), 2.61-2.64 (dd, 1H, Asp), 2.73 (t, 2H, NHCH$_2$CH$_2$Ph), 3.35 (q, 2H, NHCH$_2$CH$_2$Ph), 4.17 (t, 1H, α-H), 4.29-4.35 (m, 2H, α-H), 5.02 (q, 2H, Cbz), 6.89 (d, 1H, db), 7.07 (d, 1H, db), 7.17-7.31 (m, 10H, Ph), 7.59 (d, 1H, NH) (d, 1H, NH), 8.51 (t, 1H, NHCH$_2$CH$_2$Ph), 10.95 (s, 1H, NH—N).

Example 2L

Cbz-Asp(O-tBu)-Glu(O-tBu)-Val-AAsp(O-tBu)-CH=CH—CON(CH$_3$) CH$_2$Ph was obtained by the EDC/HOBt coupling method, and purified by column chromatography on silica gel with 1:9:5 MeOH:CH$_2$Cl$_2$:EtOAc as the eluent, and then rechromatographed using 1:1 EtOAc:hexanes as the eluent; white solid, yield 34%. MS (ESI) m/z 937.5 [(M+1)$^+$]. $^1$H NMR (DMSO-d$_6$): 0.86 (t, 6H, Val), 1.34-1.41 (m, 27H, tBu), 1.65 (m, 1H, Glu), 1.88 (m, 1H, Glu), 1.97 (m, 1H, Val), 2.17 (m, 2H, Glu), 2.43 (dd, 1H, Asp), 2.59 (dd, 1H, Asp), 2.88-2.98 (d, 3H, N(CH$_3$)CH$_2$Ph), 4.16 (t, 1H, α-H), 4.29-4.34 (dm, 2H, α-H), 4.54 (q, 1H, N(CH$_3$)CH$_2$Ph), 4.67 (s, 1H, N(CH$_3$)CH$_2$Ph), 5.02 (q, 2H, Cbz), 7.14 (d, 1H, db), 7.20 (d, 1H, db), 7.28-7.37 (m, 10H, Ph), 7.56 (d, 1H, NH), 7.94 (t, 1H, NH), 10.97 (s, 1H, NH—N).

Example 2M

Cbz-Asp(O-tBu)-Glu(O-tBu)-Val-AAsp(O-tBu)-CH=CH—CON(CH$_3$)CH$_2$CH$_2$Ph was obtained by the EDC/HOBt coupling method, and purified by column chromatography on silica gel with 1:19:20 MeOH:CH$_2$Cl$_2$:EtOAc as the eluent, and then rechromatographed using 1:1 EtOAc:CH$_2$Cl$_2$ as the eluent; white solid, yield 45%. MS (ESI) m/z 951.5 [(M+1)$^+$]. $^1$H NMR (acetone-d$_6$): 0.86 (t, 6H, Val), 1.41-1.48 (m, 27H, tBu), 1.75 (m, 1H, Glu), 1.89 (m, 1H, Glu), 2.01 (m, 1H, Val), 2.21 (m, 2H, Glu), 2.46 (dd, 1H, Asp), 2.62 (dd, 1H, Asp), 2.80 (t, 2H, N(CH$_3$)CH$_2$CH$_2$Ph), 2.85-2.98 (d, 3H, N(CH$_3$)CH$_2$CH$_2$Ph), 3.73 (m, 2H, N(CH$_3$)CH$_2$CH$_2$Ph), 4.18 (t, 1H, α-H), 4.32 (dm, 2H, α-H), 5.00 (q, 2H, Cbz), 6.88 (t, 1H, NH), 7.17-7.34 (m, 12H, Cbz-Ph, N(CH$_3$)CH$_2$CH$_2$Ph, and CH=CH), 7.59 (d, 1H, NH), 7.85 (d, 1H, NH), 7.97 (d, 1H, NH), 9.89 (d, 1H, NH—N).

Example 2N

Cbz-Asp(O-tBu)-Glu(O-tBu)-Val-AAsp(O-tBu)-CH=CH—CON(CH$_2$Ph)$_2$ was obtained by the EDC/HOBt coupling method, and purified by column chromatography on silica gel with 2:1 EtOAc:hexane as the eluent, and then rechromatographed using 1:1 EtOAc:hexanes as the eluent; white solid, yield 62%. MS (ESI) m/z 1013.4 [(M+1)$^+$]. $^1$H NMR (DMSO-d$_6$): 0.87 (t, 6H, Val), 1.35-1.39 (m, 27H, tBu), 1.73 (m, 1H, Glu), 1.87 (m, 1H, Glu), 2.02 (m, 1H, Val), 2.23 (m, 2H, Glu), 2.48 (dd, 1H, Asp), 2.65 (dd, 1H, Asp), 4.19 (t, 1H, α-H), 4.33 (m, 2H, α-H), 4.55 (d, 2H, N(CH$_2$Ph)$_2$), 4.63 (s, 2H, N(CH$_2$Ph)$_2$), 5.00 (q, 2H, Cbz), 7.14 (d, 1H, db), 7.21-7.34 (m, 16H, db, Cbz-Ph, and N(CH$_2$Ph)$_2$), 7.60 (d, 1H, NH), 7.91-7.98 (dd, 2H, NH), 11.00 (s, 1 H, NH—N).

Example 2O

Cbz-Asp(O-tBu)-Glu(O-tBu)-Val-AAsp(O-tBu)-CH=CH—CONHCH$_2$-4-F-Ph was obtained by the EDC/HOBt coupling method, and purified by column chromatography on silica gel with 1:19:20 MeOH:CH$_2$Cl$_2$:EtOAc as the eluent; white solid, yield 67%. MS (ESI) m/z 941.4 [(M+1)$^+$]. $^1$H NMR (DMSO-d$_6$): 0.86 (t, 6H, Val), 1.34-1.41 (m, 27H, tBu), 1.75 (m, 1H, Glu), 1.88 (m, 1H, Glu), 2.01 (m, 1H, Val), 2.20 (m, 2H, Glu), 2.48 (dd, 1H, Asp), 2.65 (dd, 1H, Asp), 4.18 (t, 1H, α-H), 4.34 (m, 4H, α-H and NHCH$_2$Ph-4-F), 5.01 (q, 2H, Cbz), 6.93 (d, 1H, db), 7.12 (d, 2H, NHCH$_2$Ph-4-F), 7.25-7.32 (m, 8H, Cbz-Ph, NHCH$_2$Ph-4-F, and db), 7.59 (d, 1H, NH), 7.90-7.99 (dd, 2H, NH), 8.94 (t, 1H, NHCH$_2$Ph-4-F), 10.98 (s, 1H, NH—N).

Example 2P

Cbz-Asp(O-tBu)-Glu(O-tBu)-Val-AAsp(O-tBu)-CH=CH—CO-tetrahydroquinoline was obtained by the EDC/HOBt coupling method, and purified by column chromatography on silica gel with 1:2 CH$_2$Cl$_2$:EtOAc as the eluent; yellow solid, yield 54%. MS (ESI) m/z 949.4 [(M+1)$^+$]. $^1$H NMR (DMSO-d$_6$): 0.89 (t, 6H, Val), 1.35-1.42 (m, 27H, tBu), 1.75 (m, 1H, Glu), 1.87 (m, 3H, Glu and NCH$_2$CH$_2$CH$_2$), 2.02 (m, 1H, Val), 2.20 (m, 2H, Glu), 2.48 (dd, 1H, Asp), 2.65 (dd, 1H, Asp), 2.70 (t, 2H, NCH$_2$CH$_2$CH$_2$), 3.73 (t, 2H, NCH$_2$CH$_2$CH$_2$), 4.19 (t, 1H, α-H), 4.33 (m, 2H, α-H), 5.01 (q, 2H, Cbz), 6.95 (m, 1H, db), 7.04 (d, 1H, db), 7.14-7.33 (m, 9H, Cbz-Ph, and quinoline), 7.60 (d, 1H, NH), 7.96 (dd, 2H, NH), 11.02 (s, 1H, NH—N).

Example 2Q

Cbz-Asp(O-tBu)-Glu(O-tBu)-Val-AAsp(O-tBu)-CH=CH—COPh was obtained by the EDC/HOBt coupling method, and purified by column chromatography on silica gel with 1:499:500 MeOH:CH$_2$Cl$_2$:EtOAc as the eluent; white solid, yield 40%. MS (ESI) m/z 894.4 [(M+1)$^+$]. $^1$H NMR (DMSO-d$_6$): 0.82 (t, 6H, Val), 1.34-1.42 (m, 27H, tBu), 1.70 (m, 1H, Glu), 1.85 (m, 1H, Glu), 1.96 (m, 1H, Val), 2.15 (m, 2H, Glu), 2.44 (dd, 1H, Asp), 2.58-2.60 (dd, 1H, Asp), 4.14 (t, 1H, α-H), 4.26-4.33 (dm, 2H, α-H), 5.02 (q, 2H, Cbz), 7.23 (d, 1H, db), 7.31 (s, 5H, Cbz), 7.51 (m, 3H, Ph), 7.66 (t, 1H, NH), 7.80 (d, 1H, db), 7.99 (d, 2H, Ph), 11.02 (s, 1H, NH—N).

Example 2R

Cbz-Ile-Glu(O-tBu)-Thr-AAsp(O-tBu)-CH=CH—COOEt was synthesized using the mixed anhydride coupling method and purified by column chromatography using 4:1 (1:9 MeOH:CH$_2$Cl$_2$):EtOAc as an eluent, and then rechromatographed using 4:1 (1:19 MeOH:CH$_2$Cl$_2$):EtOAc as the eluent; white solid, yield 36%. MS (ESI) m/z 806 [(M+1)$^+$].

Example 2S

Cbz-Ile-Glu(O-tBu)-Thr-AAsp(O-tBu)-CH=CH—COOCH$_2$Ph was obtained using the EDC/HOBt coupling method, purified by column chromatography on silica gel with 50:45:5 CH$_2$Cl$_2$:EtOAc:MeOH as the eluent; white solid, yield 37%. $^1$H NMR (CDCl$_3$): 0.91 and 0.94 (m, 6H, Ile CH$_3$), 1.20 (m, H, Ile CH$_2$ and Thr CH$_3$), 1.45 (s, 19H, t-Bu and Ile CH), 2.05 and 2.20 (d of m, 2H, Glu CH$_2$), 2.35 and 2.50 (d of m, 2H, Glu CH$_2$), 3.21 (s, 2H, AAsp CH$_2$), 4.12 (m, 2H, α-H), 4.30 (m, 2H, α-H), 4.44 (m, 1H, Thr CH), 5.10 (m, 4H, Cbz and CH$_2$Ph), 5.40 (d, 1H, NH), 6.85 and 7.20 (d of d, 2H, CH=CH), 7.20-7.40 (m, 10H, Ph), 7.50 (d, 1H, NH), 8.00 (d, 1H, NH), 9.40 (s, 1H, NH).

Example 2T

Cbz-Ile-Glu(O-tBu)-Thr-AAsp(O-tBu)-CH=CH—CONHPh was obtained using the EDC/HOBt coupling method, purified by column chromatography on silica gel with 50:45:5 CH$_2$Cl$_2$:EtOAc:MeOH as the eluent; white solid, yield 67%. $^1$H NMR (acetone-d$_6$): 0.89 and 0.99 (m, 6H, Ile CH$_3$), 1.24 (m, 5H, Thr CH$_3$ and Ile CH$_2$), 1.45 (s, 18H, t-Bu), 1.60 (m, 1H, Ile CH), 1.95 and 2.15 (d of m, 2H, Glu CH$_2$), 2.39 (m, 2H, Glu CH$_2$), 2.86 (s, 2H, AAsp CH$_2$), 4.16 (m, 1H, α-H), 4.35 (m, 1H, α-H), 4.45 (m, 2H, α-H and Thr CH), 5.10 (q, 2H, Cbz), 6.70 (d, 1H, NH), 6.80 and 7.20 (d of d, 2H, CH=CH), 7.08 (m, 2H, Ph), 7.35 (m, 6H, Ph), 7.52 (m, 1H, NH), 7.78 (t, 2H, Ph), 7.90 (b, 1H, NH), 9.60 (s, 1H, NH), 9.70 (s, 1H, NH).

Example 2U

Cbz-Ile-Glu(O-tBu)-Thr-AAsp(O-tBu)-CH=CH—CONHCH$_2$Ph was obtained using the EDC/HOBt coupling method, purified by column chromatography on silica gel with 50:45:5 CH$_2$Cl$_2$:EtOAc:MeOH as the eluent; white solid, yield 30%. $^1$H NMR (CDCl$_3$): 0.92 and 0.95 (m, 6H, Ile CH$_3$), 1.19 (m, 5H, Ile CH$_2$ and Thr CH$_3$), 1.45 (s, 18H, t-Bu), 1.80 (m, 1H, Ile CH), 1.90 (m, 2H, Glu CH$_2$), 2.30 and 2.40 (d of m, 2H, Glu CH$_2$), 3.20 (s, 2H, AAsp CH$_2$), 4.12 (m, 1H, α-H), 4.38 (m, 3H, α-H, Thr CH and CH$_2$Ph), 4.52 (m, 1H, CH$_2$Ph), 5.10 (s, 2H, Cbz), 5.53 (d, 1H, NH), 6.85 (d, 1H, CH=CH), 7.15-7.40 (m, 11H, CH=CH and Ph), 7.70 (s, 1H, NH), 8.05 (b, 1H, NH), 8.35 (b, 1H, NH), 9.45 (s, 1H, NH).

Example 2V

Cbz-Ile-Glu(O-tBu)-Thr-AAsp(O-tBu)-CH=CH—CONHCH$_2$CH$_2$Ph was obtained using the EDC/HOBt coupling method, purified by column chromatography on silica gel with 50:45:5 CH$_2$Cl$_2$:EtOAc:MeOH as the eluent; white solid, yield 77%. $^1$H NMR (CDCl$_3$): 0.92 and 0.98 (m, 6H, Ile CH$_3$), 1.19 (m, 5H, Ile CH$_2$ and Thr CH$_3$), 1.45 (s, 18H, t-Bu), 1.80 (m, 1H, Ile CH), 1.95 and 2.10 (d of m, 2H, Glu CH$_2$), 2.35 and 2.50 (d of m, 2H, Glu CH$_2$), 2.80 (m, 2H, CH$_2$Ph), 3.20 (s, 2H, AAsp CH$_2$), 3.52 (m, 2H, NCH$_2$), 4.15 (m, 2H, α-H), 4.25 (m, 1H, α-H), 4.40 (m, 1H, Thr CH), 5.11 (s, 2H, Cbz), 5.45 (d, 1H, NH), 6.85 (d, 1H, CH=CH), 7.15-7.40 (m, 12H, CH=CH, Ph and NH), 7.70 (b, 1H, NH), 8.05 (b, 1H, NH), 9.40 (s, 1H, NH).

Example 2W

Cbz-Ile-Glu(O-tBu)-Thr-AAsp(O-tBu)-CH=CH—CON(CH$_3$)CH$_2$Ph was obtained using the EDC/HOBt coupling method, purified by column chromatography on silica gel with 50:45:5 CH$_2$Cl$_2$:EtOAc:MeOH as the eluent; white solid, yield 77%. $^1$H NMR (acetone-d$_6$): 0.90 and 0.99 (m, 6H, Ile CH$_3$), 1.21 (m, 3H, Thr CH$_3$), 1.45 (s, 18H, t-Bu), 1.60 (m, 3H, Ile CH and CH$_2$), 1.96 (m, 2H, Glu CH$_2$), 2.38 (m, 2H, Glu CH$_2$), 2.84 (s, 2H, AAsp CH$_2$), 2.95 and 3.08 (d, 3H, NCH$_3$), 4.15-4.30 (m, 3H, α-H), 4.42 (m, 1H, Thr CH), 4.65 (s, 2H, CH$_2$Ph), 5.08 (q, 2H, Cbz), 6.63 (d, 1H, NH), 7.20-

7.40 (m, 13H, CH=CH, Ph and NH), 7.52 (d, 1H, NH), 7.84 (d, 1H, NH), 9.75 (s, 1H, NH).

Example 2X

Cbz-Ile-Glu(O-tBu)-Thr-AAsp(O-tBu)-CH=CH—CON(CH$_3$)CH$_2$CH$_2$Ph was obtained using the EDC/HOBt coupling method, purified by column chromatography on silica gel with 50:45:5 CH$_2$Cl$_2$:EtOAc:MeOH as the eluent; white solid, yield 71%. 1H NMR (CDCl$_3$): 0.90 (m, 3H, Ile CH$_3$), 0.96 (m, 3H, Ile CH$_3$), 1.20 (m, 3H, Thr CH$_3$), 1.45 (s, 18H, t-Bu), 1.80-1.90 (m, 3H, Ile CH and CH$_2$), 2.10 (m, 2H, Glu CH$_2$), 2.40 (m, 2H, Glu CH$_2$), 2.85 (m, 2H, CH$_2$Ph), 2.97 (d, 3H, NCH$_3$), 3.30 (m, 2H, AAsp CH$_2$), 3.54 (m, 2H, NCH$_2$), 4.20 (m, 2H, α-H), 4.41 (m, 2H, α-H and Thr CH), 5.11 (q, 2H, Cbz), 5.60 (d, 1H, NH), 7.10-7.40 (m, 13H, CH=CH, Ph and NH), 7.85 (b, 1H, NH), 9.50 (d, 1H, NH).

Example 2Y

Cbz-Ile-Glu(O-tBu)-Thr-AAsp(O-tBu)-CH=CH—CON(CH$_2$Ph)$_2$ was obtained using the EDC/HOBt coupling method, purified by column chromatography on silica gel with 50:45:5 CH$_2$Cl$_2$:EtOAc:MeOH as the eluent; white solid, yield 46%. 1H NMR (acetone-d$_6$): 0.89 and 0.99 (m, 6H, Ile CH$_3$), 1.21 (m, 3H, Thr CH$_3$), 1.45 (s, 18H, t-Bu), 1.60 (m, 3H, Ile CH and CH$_2$), 1.95 and 2.10 (d of m, 2H, Glu CH$_2$), 2.39 (m, 2H, Glu CH$_2$), 2.84 (s, 2H, AAsp, CH$_2$), 4.15 (t, 1H, α-H), 4.35 (m, 1H, α-H), 4.45 (m, 2H, α-H and Thr CH), 4.67 (m, 4H, CH$_2$Ph), 5.09 (q, 2H, Cbz), 5.60 (d, 1H, NH), 7.20-7.40 (m, 17H, CH=CH and Ph), 7.55 (d, 1H, NH), 7.85 (d, 1H, NH), 9.75 (s, 1H, NH).

Example 2Z

Cbz-Leu-Glu(O-tBu)-Thr-AAsp(O-tBu)-CH=CH—COOEt was synthesized using the mixed anhydride coupling method and purified by column chromatography using 4:1 (1:19 MeOH:CH$_2$Cl$_2$):EtOAc as the eluent; white solid, yield 35%. MS (ESI) m/z 806 [(M+1)$^+$]. $^1$H NMR (DMSO-d$_6$): 0.85 (t, 6H, Leu CH$_3$), 1.1 (d, 3H, Thr CH$_3$), 1.2-1.3 (t, 3H, OCH$_2$CH$_3$), 1.3-1.5 (d, 20H, tBu and Leu CH$_2$), 1.6 (m, 1H, CH Leu), 1.7 (m, 1H, Glu CH$_2$), 1.9 (m, 1H, Glu CH$_2$), 2.2 (m, 2H, Glu CH$_2$), 3.9-4.1 (m, 4H, NCH$_2$COOH and α-H), 4.1-4.2 (m, 3H, OCH$_2$CH$_3$ and CH—OH), 4.3 (m, 2H, α-H), 5.0 (s, 2H, Cbz), 6.6 (d, 1H, CH=CH), 7.20-7.40 (m, 6H, Ph and CH=CH), 7.50 (d, 1H, NH), 7.75 (d, 1H, NH), 8.0 (d, 1H, NH).

Example 2AA

Cbz-Leu-Glu(O-tBu)-Thr-AAsp(O-tBu)-CH=CH—COOCH$_2$Ph was obtained by the EDC/HOBt coupling method, and purified by column chromatography on silica gel with 1:499:500 MeOH:CH$_2$Cl$_2$:EtOAc as the eluent; white solid, yield 52%. MS (ESI) m/z 868.4 [(M+1)$^+$]. $^1$H NMR (DMSO-d$_6$): 0.83 (t, 6H, Leu), 1.02 (d, 3H, Thr), 1.36-1.40 (t, 20H, tBu and Leu), 1.60 (m, 1H, Glu), 1.72 (m, 1H, Glu), 1.88 (m, 1H, Leu), 2.21 (m, 2H, Glu), 3.92 (m, 1H, α-H), 4.03 (m, 1H, α-H), 4.17 (m, 1H, α-H), 4.34 (m, 1H, Thr), 4.99 (s, 2H, Cbz), 5.19 (s, 2H, Bzl), 6.67-6.71 (d, 1H, db), 7.32-7.38 (m, 10H, Ph), 7.40 (d, 1H, db), 7.76 (d, 1H, NH), 8.04 (d, 1H, NH), 10.80 (s, 1H, NH—N).

Example 2BB

Cbz-Leu-Glu(O-tBu)-Thr-AAsp(O-tBu)-CH=CH—CONHPh was obtained using the EDC/HOBt coupling method, purified by column chromatography on silica gel with 50:45:5 CH$_2$Cl$_2$:EtOAc:MeOH as the eluent; white solid, yield 80%. $^1$H NMR (acetone-d$_6$): 0.93 (d, 6H, Leu CH$_3$), 1.22 (m, 3H, Thr CH$_3$), 1.44 (s, 18H, t-Bu), 1.67 (t, 2H, Leu CH$_2$), 1.78 (m, 1H, Leu CH), 1.95 and 2.15 (d of m, 2H, Glu CH$_2$), 2.38 (m, 2H, Glu CH$_2$), 2.87 (s, 2H, AAsp CH$_2$), 4.30-4.35 (m, 3H, α-H), 4.42 (m, 1H, Thr CH), 5.09 (q, 2H, Cbz), 6.75 (d, 1H, NH), 6.80 and 7.20 (d of d, 2H, CH=CH), 7.08 (m, 2H, Ph), 7.35 (m, 6H, Ph), 7.52 (m, 1H, NH), 7.78 (t, 2H, Ph), 7.88 (b, 1H, NH), 9.63 (s, 1H, NH), 9.72 (s, 1H, NH).

Example 2CC

Cbz-Leu-Glu(O-tBu)-Thr-AAsp(O-tBu)-CH=CH—CONHCH$_2$Ph was obtained using the EDC/HOBt coupling method, purified by column chromatography on silica gel with 50:45:5 CH$_2$Cl$_2$:EtOAc:MeOH as the eluent; white solid, yield 38%. $^1$H NMR (CDCl$_3$): 0.94 (d, 6H, Leu CH$_3$), 1.20 (m, 3H, Thr CH$_3$), 1.45 (s, 18H, t-Bu), 1.64 (m, 3H, Leu CH and CH$_2$), 2.00 (m, 2H, Glu CH$_2$), 2.34 and 2.42 (d of m, 2H, Glu CH$_2$), 3.20 (s, 2H, AAsp CH$_2$), 4.10 (m, 1H, α-H), 4.21 (m, 2H, α-H), 4.40-4.50 (m, 3H, Thr CH and CH$_2$Ph), 5.05 (q, 2H, Cbz), 5.42 (d, 1H, NH), 6.85 (d, 1H, CH=CH), 7.15-7.40 (m, 11H, CH=CH and, Ph), 7.55 (b, 1H, NH), 7.70 (b, 1H, NH), 8.20 (b, 1H, NH), 9.40 (s, 1H, NH).

Example 2DD

Cbz-Leu-Glu(O-tBu)-Thr-AAsp(O-tBu)-CH=CH—CONHCH$_2$CH$_2$Ph was obtained using the EDC/HOBt coupling method, purified by column chromatography on silica gel with 50:45:5 CH$_2$Cl$_2$:EtOAc:MeOH as the eluent; white solid, yield 55%. $^1$H NMR (CDCl$_3$): 0.94 (d, 6H, Leu CH$_3$), 1.20 (m, 3H, Thr CH$_3$), 1.45 (s, 18H, t-Bu), 1.65 (m, 3H, Leu CH and CH$_2$), 2.05 (m, 2H, Glu CH$_2$), 2.40 (m, 2H, Glu CH$_2$), 2.78 (m, 2H, CH$_2$Ph), 3.20 (s, 2H, AAsp CH$_2$), 3.50 (m, 2H, NCH$_2$), 4.24 (m, 3H, α-H), 4.41 (m, 1H, Thr CH), 5.05 (s, 2H, Cbz), 5.62 (d, 1H, NH), 6.80 and 7.10 (d of d, 2H, CH=CH), 7.15-7.40 (m, 12H, Ph and NH), 8.00 (b, 1H, NH), 9.45 (s, 1H, NH).

Example 2EE

Cbz-Leu-Glu(O-tBu)-Thr-AAsp(O-tBu)-CH=CH—CON(CH$_3$)CH$_2$Ph was obtained using the EDC/HOBt coupling method, purified by column chromatography on silica gel with 50:45:5 CH$_2$Cl$_2$:EtOAc:MeOH as the eluent; white solid, yield 77%. $^1$H NMR (acetone-d$_6$): 0.94 (d, 6H, Leu CH$_3$), 1.20 (m, 3H, Thr CH$_3$), 1.45 (s, 18H, t-Bu), 1.65 (m, 2H, Leu CH$_2$), 1.80 (m, 1H, Leu CH), 1.95-2.10 (d of m, 2H, Glu CH$_2$), 2.38 (d of m, 2H, Glu CH$_2$), 2.85 (s, 2H, AAsp CH$_2$), 2.95 and 3.08 (d, 3H, NCH$_3$), 4.30 (m, 3H, α-H), 4.42 (m, 1H, Thr CH), 4.65 (s, 2H, CH$_2$Ph), 5.08 (q, 2H, Cbz), 6.75 (d, 1H, NH), 7.20-7.40 (m, 12H, CH=CH and Ph), 7.44 (d, 1H, NH), 7.90 (d, 1H, NH), 9.75 (s, 1H, NH).

Example 2FF

Cbz-Leu-Glu(O-tBu)-Thr-AAsp(O-tBu)-CH=CH—CON(CH$_3$)CH$_2$CH$_2$Ph was obtained using the EDC/HOBt coupling method, purified by column chromatography on silica gel with 50:45:5 CH$_2$Cl$_2$:EtOAc:MeOH as the eluent; white solid, yield 76%. $^1$H NMR (CDCl$_3$): 0.94 (m, 6H, Leu CH$_3$), 1.21 (m, 3H, Thr CH$_3$), 1.45 (s, 18H, t-Bu), 1.55 (m, 2H, Leu CH$_2$), 1.70 (m, 1H, Leu CH), 2.13 (m, 2H, Glu CH$_2$), 2.43 (m, 2H, Glu CH$_2$), 2.81 (m, 2H, CH$_2$Ph), 2.88 and 2.92 (d, 3H, NCH$_3$), 3.56 (m, 4H, NCH$_2$ and AAsp CH$_2$), 4.30 (m, 2H, α-H), 4.43 (m, 2H, α-H and Thr CH), 5.10 (q, 2H, Cbz), 5.55 (m, 1H, NH), 7.10-7.40 (m, 12H, CH=CH and Ph), 7.45 (d, 1H, NH), 7.95 (b, 1H, NH), 9.42 (d, 1H, NH).

Example 2GG

Cbz-Leu-Glu(O-tBu)-Thr-AAsp(O-tBu)-CH=CH—CON(CH$_2$Ph)$_2$ was obtained using the EDC/HOBt coupling method, purified by column chromatography on silica gel with 50:45:5 CH$_2$Cl$_2$:EtOAc:MeOH as the eluent; white solid, yield 85%. $^1$H NMR (acetone-d$_6$): 0.93 (d, 6H, Leu CH$_3$), 1.21 (m, 3H, Thr CH$_3$), 1.45 (s, 18H, t-Bu), 1.67 (m, 2H, Leu CH$_2$), 1.80 (m, 1H, Leu CH), 1.95 and 2.10 (d of m, 2H, Glu CH$_2$), 2.39 (m, 2H, Glu CH$_2$), 2.88 (s, 2H, AAsp CH$_2$), 4.25-4.35 (m, 3H, α-H), 4.43 (m, 1H, Thr CH), 4.66 (m, 4H, CH$_2$Ph), 5.09 (q, 2H, Cbz), 6.75 (d, 1H, NH), 7.20-7.40 (m, 17H, CH=CH and Ph), 7.55 (d, 1H, NH), 7.90 (b, 1H, NH), 9.75 (s, 1H, NH).

Example 2HH

Cbz-Leu-Glu(O-tBu)-Thr-AAsp(O-tBu)-CH=CH—CONHCH$_2$-4-F-Ph was obtained using the EDC/HOBt coupling method, purified by column chromatography on silica gel with 50:45:5 CH$_2$Cl$_2$:EtOAc:MeOH as the eluent; white solid, yield 46%. $^1$H NMR (acetone-d$_6$): 0.92 (d, 6H, Leu CH$_3$), 1.21 (d, 3H, Thr CH$_3$), 1.45 (s, 18H, t-Bu), 1.66 (t, 2H, Leu CH$_2$), 1.76 (m, 1H, Leu CH), 1.95 and 2.10 (d of m, 2H, Glu CH$_2$), 2.36 (m, 2H, Glu CH$_2$), 3.20 (s, 2H, AAsp CH$_2$), 4.29 (m, 3H, α-H), 4.40 (m, 1H, Thr CH), 4.50 (d, 2H, CH$_2$Ph), 5.10 (q, 2H, Cbz), 6.76 (d, 1H, NH), 6.91 (d, 1H, CH=CH), 7.07 (d. 2H, CH=CH and Ph), 7.25-7.40 (m, 8H, Ph), 7.50 (b, 1H, NH), 7.95 (b, 1H, NH), 8.23 (b, 1H, NH), 9.70 (s, 1H, NH).

Example 2II

Cbz-Leu-Glu(O-tBu)-Thr-AAsp(O-tBu)-CH=CH—CO-tetrahydroquinoline was obtained using the EDC/HOBt coupling method, purified by column chromatography on silica gel with 50:45:5 CH$_2$Cl$_2$:EtOAc:MeOH as the eluent; white solid, yield 85%. $^1$H NMR (CDCl$_3$): 0.94 (m, 6H, Leu CH$_3$), 1.21 (m, 3H, Thr CH$_3$), 1.45 (s, 18H, t-Bu), 1.60 (m, 2H, Leu CH$_2$), 1.70 (m, 1H, Leu CH), 1.90 (m, 2H, quinoline CH$_2$), 2.10 (m, 2H, Glu CH$_2$), 2.45 (m, 2H, Glu CH$_2$), 2.67 (t, 2H, quinoline CH$_2$), 3.40 (m, 2H, AAsp CH$_2$), 3.90 (m, 2H, NCH$_2$), 4.30 (m, 2H, α-H), 4.45 (m, 2H, α-H and Thr CH), 5.10 (q, 2H, Cbz), 5.55 (b, 1H, NH), 6.90 (b, 1H, NH), 7.10-7.40 (m, 10H, CH=CH and Ph), 7.50 (d, 1H, Ph), 7.95 (d, 1H, NH), 9.40 (d, 1H, NH).

Example 2JJ

Cbz-Leu-Glu(O-tBu)-Thr-AAsp(O-tBu)-CH=CH—CON(CH$_3$)CH$_2$-1-Napth was obtained using the EDC/HOBt coupling method, purified by column chromatography on silica gel with 50:45:5 CH$_2$Cl$_2$:EtOAc:MeOH as the eluent; white solid, yield 66%. 1H NMR (CDCl$_3$): 0.95 (m, 6H, Leu CH$_3$), 1.22 (m, 3H, Thr CH$_3$), 1.45 (s, 18H, t-Bu), 1.55 (m, 2H, Leu CH$_2$), 1.70 (m, 1H, Leu CH), 2.15 (m, 2H, Glu CH$_2$), 2.45 (m, 2H, Glu CH$_2$), 2.92 and 2.99 (d, 3H, NCH$_3$), 3.30 (m, 2H, AAsp CH$_2$), 4.31 (m, 2H, α-H), 4.47 (m, 2H, α-H and Thr CH), 5.09 (m, 4H, CH$_2$-napth and Cbz), 5.50 (b, 1H, NH), 7.10 (d, 1H, NH), 7.20-7.40 (m, 10H, CH=CH and Ph), 7.52 (m, 2H, napth), 7.79 (d, 1H, NH), 7.90 (m, 2H, napth), 9.45 (d, 1H, NH).

Example 2KK

Cbz-Val-Glu(O-tBu)-Val-AAsp(O-tBu)-CH=CH—COOEt was obtained by the EDC/HOBt coupling method, and purified by column chromatography on silica gel with 1:9:5 MeOH:CH$_2$Cl$_2$:EtOAc as the eluent; white solid, yield 71%. MS (ESI) m/z 790.3 [(M+1)$^+$]. $^1$H NMR (DMSO-d$_6$): 0.81-0.87 (dd, 12H, Val), 1.22 (t, 3H, OCH$_2$CH$_3$), 1.24-1.41 (d, 18H, tBu), 1.72 (m, 1H, Glu), 1.83 (m, 1H, Glu), 1.96 (m, 1H, Val), 2.19 (m, 2H, Glu), 3.86 (t, 1H, α-H), 4.17 (m, 3H, α-H and OCH$_2$CH$_3$), 4.32 (m, 1H, α-H), 5.01 (s, 2H, Cbz), 6.64 (d, 1H, db), 7.20 (d, 1H, db), 7.30-7.33 (m, 5H, Ph), 7.97 (t, 2H, NH), 11.02 (s, 1H, NH—N).

Example 3A

N$^2$—(N-Benzyloxycarbonylalanylalanyl)-N$^1$-carbamoylmethyl-N$^1$-trans-(3-ethylesterpropenoyl)hydrazine (Cbz-Ala-Ala-AAsn-CH=CH—COOEt) was synthesized using the EDC/HOBt coupling method, purified by chromatography on a silica gel column using 1:13 MeOH:CH$_2$Cl$_2$ as the eluent, and then recrystallized from EtOAc/hexane; white solid, yield 33%. $^1$H NMR (DMSO-d$_6$): 1.15-1.3 (m, 9H, CH$_3$), 3.3 (m, 2H, NCH$_2$CO), 4.05 (m, 1H, α-H), 4.1-4.2 (q, 2H, OCH$_2$CH$_3$), 4.3 (m, 1H, α-H), 5.0 (m, 2H, Cbz), 6.55-6.65 (d, 1H, CH=CH), 7.1-7.2 (m, 2H, NH and CH=CH), 7.2-7.4 (m, 5H, Ph), 7.5 (s, 1H, NH), 8.15 (d, 1H, NH). HRMS (FAB) Calcd. for C$_{22}$H$_{30}$N$_5$O$_8$: 492.20944. Observed m/z 492.20565. Anal. Calcd. for C$_{22}$H$_{29}$N$_5$O$_8$: C, 53.76; H, 5.95; N, 14.25. Found: C, 53.52; H, 5.87; N, 14.11.

Example 3B

N$^2$—(N-Benzyloxycarbonylalanylalanyl)-N$^1$-trans-(3-benzyloxycarbonylpropenoyl)-N$^1$-carbamoylmethylhydrazine (Cbz-Ala-Ala-AAsn-CH=CH—COOBzl). This compound was obtained using the HOBt/EDC coupling method and purified by column chromatography on silica gel using 10% MeOH/CH$_2$Cl$_2$ as the eluent and then recrystallized from EtOAc/hexane to give a white powder (20% yield). $^1$H-NMR ((CD$_3$)$_2$CO): 1.37 (m, 6H, 2×Ala-CH$_3$), 2.88 (s, 2H, NCH$_2$CO), 4.21-4.24 (m, 1H, α-H), 4.50 (m, 1H, α-H), 5.10 (m, 2H, Cbz), 5.24 (s, 2H, O—CH$_2$-Ph), 6.58-6.33 (m, 2H, NH and CH=CH), 6.74-6.88 (d, 1H, CH=CH), 7.31-7.44 (m, 11H, 2×Ph and NH), 7.76 (s, 1H, NH), 8.16 (d, 1H, NH), 9.89 (s, 1H, NH). MS (ESI) m/z 554 [(M+1)$^+$]. HRMS (ESI) calculated for C$_{27}$H$_{32}$N$_5$O$_8$: 554.2219. Observed m/z 554.225088. Anal. Calcd. for C$_{27}$H$_{31}$N$_5$O$_8$.0.2H$_2$O: C, 58.20; H, 5.68; N, 12.57. Found: C, 58.16; H, 5.60; N, 12.47.

Example 3C

N$^2$—(N-Benzyloxycarbonylalanylalanyl)-N$^1$-carbamoylmethyl-N$^1$-trans-(3-diethylcarbamoylpropenoyl)hydrazine (Cbz-Ala-Ala-AAsn-CH=CH—CONEt$_2$). This compound was obtained using the HOBt/EDC coupling method and purified by column chromatography on silica gel using 10% MeOH/CH$_2$Cl$_2$ as the eluent and then recrystallized from EtOAc/hexane to give a white powder (11% yield). $^1$H-NMR (DMSO-d$_6$): 1.02-1.05 (t, 3H, NCH$_2$CH$_3$), 1.08-1.11 (t, 3H, NCH$_2$CH$_3$), 1.17-1.19 (d, 2H, Ala-CH$_3$), 1.24-1.26 (d, 2H, Ala-CH$_3$), 3.20-3.32 (d, 6H, NCH$_2$CO and 2×N—CH$_2$), 4.02-4.07 (m, 1H, α-H), 4.27-4.31 (m, 1H, α-H), 4.99 (m, 2H, Cbz), 7.00-7.04 (d, 1H, CH=CHCON), 7.18 (s, 1H, NH), 7.33 (m, 6H, Ph and CH=CHCON), 7.39 (d, 1H, NH), 8.20 (d, 1H, NH), 10.68 (s, 1H, NH). MS (ESI) m/z 519 [(M+1)$^+$]. HRMS (ESI) calculated for $C_{24}H_{35}N_6O_7$: 519.2608. Observed m/z 519.2657. Anal. Calcd. for $C_{24}H_{34}N_6O_7 \cdot 0.7H_2O$: C, 54.27; H, 6.72; N, 15.82. Found: C, 54.25; H, 6.69; N, 15.87.

Example 3D $N^2$—(N-Benzyloxycarbonylalanylalanyl)-$N^1$-carbamoylmethyl-$N^1$-trans-(3-dibutylcarbamoylpropenoyl)hydrazine (Cbz-Ala-Ala-AAsn-CH=CH—CON(nBu)$_2$). This compound was obtained using the HOBt/EDC coupling method and purified by column chromatography on silica gel using 10% MeOH/CH$_2$Cl$_2$ as the eluent and then recrystallized from EtOAc/hexane to give a white powder (15% yield). $^1$H-NMR (DMSO-d$_6$): 0.95 (m, 6H, 2×nBu-CH$_3$), 1.11-1.27 (m, 6H, 2×Ala-CH$_3$), 1.30-1.37 (m, 4H, 2×CH$_2$CH$_2$CH$_2$CH$_3$), 1.53 -1.59 (m, 4H, 2×CH$_2$CH$_2$CH$_2$CH$_3$), 3.20-3.32 (d, 6H, NCH$_2$CO and 2×N—CH$_2$), 4.00-4.01 (m, 1H, α-H), 4.25-4.30 (m, 1H, α-H), 4.99 (m, 2H, Cbz), 7.00-7.04 (d, 1H, CH=CHCON), 7.21 (s, 1H, NH), 7.33 (m, 6H, Ph and CH=CHCON), 7.42 (d, 1H, NH), 8.20 (d, 1H, NH), 10.73 (s, 1H, NH). MS (FAB) m/z 575 [(M+1)$^+$]. HRMS (FAB) calculated for $C_{28}H_{43}N_6O_7$:575.32052. Observed m/z 575.31932. Anal. Calcd. for $C_{28}H_{42}N_6O_7 \cdot 0.8H_2O$: C, 57.16; H, 7.35; N, 14.28. Found: C, 57.18; H, 7.35; N, 14.28.

Example 3E $N^2$—(N-Benzyloxycarbonylalanylalanyl)-$N^1$-carbamoylmethyl-$N^1$-trans-(3-(1-piperidyloxo)propenoyl)hydrazine (Cbz-Ala-Ala-AAsn-CH=CH—CO-Pip). This compound was obtained using the HOBt/EDC coupling method and purified by column chromatography on silica gel using 10% MeOH/CH$_2$Cl$_2$ as the eluent and recrystallized from hexane/EtOAc to give a white powder (10% yield). $^1$H-NMR ((CD$_3$)CO): 1.28 (m, 2H, piperidine-CH$_2$), 1.37 (d, 3H, Ala-CH$_3$), 1.41 (d, 3H, Ala-CH$_3$), 1.52-1.67 (m, 4H, 2×piperidine-CH$_2$), 2.80 (s, 2H, NCH$_2$CO), 3.55 (m, 4H, CH$_2$—N—CH$_2$), 4.24 (m, 1H, α-H), 4.50 (m, 1H, α-H), 5.10 (m, 2H, Cbz), 7.11-7.15 (d, 1H, J=14.8 Hz, CH=CHCON), 7.30-7.44 (m, 7H, CH=CHCON and Ph and NH), 7.77 (s, 1H, NH), 9.82 (s, 1H, NH). MS (ESI) m/z 531 [(M+1)$^+$]. HRMS (ESI) calculated for $C_{25}H_{35}N_6O_7$: 531.2532. Observed m/z 531.256723. Anal. Calcd. for $C_{25}H_{34}N_6O_7 \cdot 0.7H_2O$: C, 55.32; H, 6.50; N, 15.48. Found: C, 55.26; H, 6.43; N, 15.28.

Example 3F $N^2$—(N-Benzyloxycarbonylalanylalanyl)-$N^1$-carbamoylmethyl-$N^1$-trans-(3-phenylcarbamoylpropenoyl)hydrazine (Cbz-Ala-Ala-AAsn-CH=CH—CONHPh). This compound was obtained using the HOBt/EDC coupling method with minimal NaHCO$_3$ washing during the workup. The product was isolated as a yellow solid without chromatography by recrystallization from 10% MeOH/CH$_2$Cl$_2$ (21% yield). $^1$H-NMR (DMSO-d$_6$): 1.18-1.27 (m, 6H, 2×Ala-CH$_3$), 3.20-3.32 (d, 2H, NCH$_2$CO), 4.04-4.08 (m, 1H, α-H), 4.28-4.31 (m, 1H, α-H), 4.99 (m, 2H, Cbz), 7.05-7.42 (m, 11H, 2×Ph, NH CH=CHCON and CH=CHCON), 7.63-7.65 (d, 2H, Ph), 7.52 (s, 1H, NH), 8.15 (d, 1H, NH), 10.42 (s, 1H, NH), 10.72 (s, 1H, NH). MS (ESI) m/z 539 [(M+1)$^+$]. HRMS (ESI) calculated for $C_{26}H_{31}N_6O_7$: 539.2208. Observed m/z 539.2254. Anal. Calcd. for $C_{26}H_{30}N_6O_7$: C, 57.98; H, 5.61; N, 15.60. Found: C, 57.73; H, 5.58; N, 15.72.

Example 3G $N^2$—(N-Benzyloxycarbonylalanylalanyl)-$N^1$-carbamoylmethyl-$N^1$-trans-(3-benzylcarbamoylpropenoyl)hydrazine (Cbz-Ala-Ala-AAsn-CH=CH—CONHBzl). This compound was obtained using the HOBt/EDC coupling method with minimal washing during the workup and purified by recrystallization from ice cold EtOAc without column chromatography (18% yield). $^1$H-NMR (DMSO-d$_6$): 1.17-1.26 (m, 6H, 2×Ala-CH$_3$), 3.30-3.32 (d, 2H, NCH$_2$CO), 4.02-4.07 (m, 1H, α-H), 4.27-4.32 (m, 1H, α-H), 4.35-4.36 (d, 2H, CH$_2$Ph), 4.99 (m, 2H, Cbz), 6.89-6.92 (d, 1H, J=14.2 Hz, CH=CHCON), 7.06-7.10 (d, 1H, J=14.8 Hz, CH=CHCON), 7.16-7.41 (m, 11H, 2×Ph and NH), 7.42 (d, 1H, NH), 8.16 (d, 1H; NH), 8.94 (t, 1H, NH), 10.72 (s, 1H, NH). MS (ESI) m/z 553 [(M+1)$^+$]. HRMS (ESI) calculated for $C_{27}H_{33}N_6O_7$: 553.2397. Observed m/z 553.2411. Anal. Calcd. for $C_{27}H_{32}N_6O_7 \cdot 0.3H_2O$: C, 58.12; H, 5.89; N, 15.06. Found: C, 58.07; H, 5.81; N, 15.03.

Example 3H $N^2$—(N-Benzyloxycarbonylalanylalanyl)-$N^1$-carbamoylmethyl-$N^1$-trans-(3-(4-fluorobenzyl)carbamoylpropenoyl) hydrazine (Cbz-Ala-Ala-AAsn-CH=CH—CONH-Bzl-4-F). This compound was obtained using the HOBt/EDC coupling method and purified by column chromatography using 10% MeOH/CH$_2$Cl$_2$ as the eluent to give a pink powder (8% yield). $^1$H-NMR (DMSO-d$_6$): 1.17-1.26 (m, 6H, 2×Ala-CH$_3$), 3.30-3.32 (d, 2H, NCH$_2$CO), 4.02-4.07 (m, 1H, α-H), 4.27-4.35 (m, 3H, α-H and CH$_2$PhF), 4.99 (m, 2H, Cbz), 6.88-6.92 (d, 1H, J=16 Hz, CH=CHCON), 7.06-7.32 (m, 11H, CH=CHCON and NH and 2×Ph), 7.43 (d, 1H, NH), 7.53 (s, 1H, NH), 8.19 (d, 1H, NH), 8.97 (t, 1H, NH), 10.72 (s, 1H, NH). MS (ESI) m/z 571 [(M+1)$^+$]. HRMS (ESI) calculated for $C_{27}H_{32}N_6O_7F$: 571.2323. Observed m/z 571.231651. Anal. Calcd. for $C_{27}H_{31}N_6O_7F$: C, 56.84; H, 5.48; N, 14.73. Found: C, 56.73; H, 5.58; N, 14.68.

Example 3I $N^2$—(N-Benzyloxycarbonylalanylalanyl)-$N^1$-carbamoylmethyl-$N^1$-trans-(3-phenethylcarbamoylpropenoyl)hydrazine (Cbz-Ala-Ala-AAsn-CH=CH—CONHCH$_2$CH$_2$Ph). This compound was obtained using the HOBt/EDC coupling method with minimal washing during the workup and purified by column chromatography on silica gel using 10% MeOH/CH$_2$Cl$_2$ as the eluent and then washed with EtOAc to give a white powder (12% yield). $^1$H-NMR (DMSO-d$_6$): 1.18-1.27 (m, 6H, 2×Ala-CH$_3$), 2.74 (m, 2H, N—CH$_2$CH$_2$Ph), 3.20-3.32 (d, 2H, NCH$_2$CO), 3.52-3.58 (m, 2H, N—CH$_2$CH$_2$Ph), 4.04-4.08 (m, 1H, α-H), 4.28-4.31 (m, 1H, α-H), 4.99 (m, 2H, Cbz), 6.86-6.89 (d, 1H, J=14.4 Hz, CH=CHCON), 7.04-7.08 (d, 1H, J=14.8 Hz, CH=CHCON), 7.16-7.41 (m, 11H, 2×Ph and NH), 7.50 (d, 1H, NH), 8.16 (d, 1H, NH), 8.53 (s, 1H, NH), 10.72 (s, 1H, NH). MS (ESI) m/z 567 [(M+1)$^+$]. HRMS (ESI) calculated for $C_{28}H_{35}N_6O_7$: 567.2596. Observed m/z 567.256723. Anal. Calcd. for $C_{28}H_{34}N_6O_7 \cdot 0.3H_2O \cdot 0.2$hexane: C, 59.52; H, 6.40; N, 14.26. Found: C, 59.71; H, 6.18; N, 13.99.

Example 3J $N^2$—(N-Benzyloxycarbonylalanylalanyl)-$N^1$-carbamoylmethyl-$N^1$-trans-(3-(methylphenylcarbamoyl)propenoyl) hydrazine (Cbz-Ala-Ala-AAsn-CH=CH—CON(CH$_3$)Ph).

This compound was obtained using the HOBt/EDC coupling method. The product was isolated by chromatography with 10% MeOH/CH$_2$Cl$_2$ as the eluent and recrystallized from hexane/EtOAc to give a white powder (34% yield). $^1$H-NMR (DMSO-d$_6$): 1.18-1.27 (m, 6H, 2×Ala-CH$_3$), 3.20-3.32 (m, 5H, NCH$_2$CO and N—CH$_3$), 4.02-4.07 (m, 1H, α-H), 4.30 (m, 1H, α-H), 4.99 (m, 2H, Cbz), 6.56 (d, 1H, CH=CHCON), 7.06-7.10 (d, 1H, CH=CHCON), 7.14 (s, 1H, NH), 7.29-7.46 (m, 11H, 2×Ph, NH), 8.14 (d, 1H, NH), 10.65 (s, 1H, NH). MS (ESI) m/z 553 [(M+1)$^+$]. HRMS (ESI) calculated for C$_{27}$H$_{33}$N$_6$O$_7$: 553.2356. Observed m/z 553.2411. Anal. Calcd. for C$_{27}$H$_{32}$N$_6$O$_7$: C, 58.69; H. 5.84; N, 15.21. Found: C, 58.43; H, 5.90; N, 15.20.

Example 3K

N$^2$—(N-Benzyloxycarbonylalanylalanyl)-N$^1$-carbamoylmethyl-N$^1$-trans-(3-benzylmethylcarbamoylpropenoyl)hydrazine (Cbz-Ala-Ala-AAsn-CH=CH—CON(CH$_3$)Bzl). This compound was synthesized using the HOBt/EDC coupling method and purified by column chromatography on silica gel using 10% MeOH/CH$_2$Cl$_2$ as the eluent and then recrystallized from EtOAc/hexane to give a white powder (54% yield). $^1$H-NMR (DMSO-d$_6$): 1.18-1.27 (m, 6H, 2×Ala-CH$_3$), 2.89 (s, 3H, N—CH$_3$), 3.20-3.32 (d, 2H, NCH$_2$CO), 4.04-4.08 (m, 1H, α-H), 4.28-4.31 (m, 1H, α-H), 4.57 (m, 2H, N—CH$_2$-Ph), 4.99 (m, 2H, Cbz), 7.05-7.41 (m, 13H, CH=CHCON and CH=CHCON and 2×Ph and NH), 7.49 (d, 1H, NH), 8.16 (d, 1H, NH), 10.72 (s, 1H, NH). MS (ESI) m/z 567 [(M+1)$^+$]. HRMS (ESI) calculated for C$_{28}$H$_{35}$N$_6$O$_7$: 567.2604. Observed m/z 567.256723. Anal. Calcd. for C$_{28}$H$_{34}$N$_6$O$_7$.0.9H$_2$O: C, 57.70; H. 6.19; N. 14.42. Found: C, 57.91; H. 6.25; N, 14.27.

Example 3L

N$^2$—(N-Benzyloxycarbonylalanylalanyl)-N$^1$-carbamoylmethyl-N$^1$-trans-(3-(methyl-1-naphthylmethylcarbamoyl)propenoyl)hydrazine (Cbz-Ala-Ala-AAsn-CH=CH—CON(CH$_3$)CH$_2$-1-Napth). This compound was obtained using the HOBt/FDC coupling method and purified by column chromatography on silica gel using 10% MeOH/CH$_2$Cl$_2$ as the eluent and then recrystallized from EtOAc/hexane to give a yellow powder (31% yield). $^1$H-NMR (DMSO-d$_6$): 1.18-1.27 (m, 6H, 2×Ala-CH$_3$), 3.10 (s, 3H, N—CH$_3$), 3.20-3.32 (d, 2H, NCH$_2$CO), 4.04-4.08 (m, 1H, α-H), 4.28-4.31 (m, 1H, α-H), 4.99 (m, 4H, Cbz and N—CH$_2$-naphthyl), 7.07-7.61 (m, 12H, naphthyl and Ph CH=CHCON and CH=CHCON and NH), 7.85-8.10 (m, 3H, naphthyl), 8.15 (d, 1H, NH), 10.42 (s, 1H, NH), 10.72 (s, 1H, NH). MS (ESI) m/z 617 [(M+1)$^+$]. HRMS (ESI) calculated for C$_{32}$H$_{37}$N$_6$O$_7$: 617.265. Observed m/z 617.2724. Anal. Calcd. for C$_{32}$H$_{36}$N$_6$O$_7$.0.5H$_2$O: C, 61.43; H, 5.96; N, 13.43. Found: C, 61.48; H, 6.03; N, 13.25.

Example 3M

N$^2$—(N-Benzyloxycarbonylalanylalanyl)-N$^1$-carbamoylmethyl-N$^1$-trans-(3-(Methylphenethylcarbamoyl)propenoyl)hydrazine (Cbz-Ala-Ala-AAsn-CH=CH—CON(CH$_3$)CH$_2$CH$_2$Ph). This compound was obtained using the HOBt/EDC coupling method and purified by column chromatography on silica gel using 10% MeOH/CH$_2$Cl$_2$ as the eluent and then recrystallized from EtOAc/hexane to give a white powder (28% yield). $^1$H-NMR (DMSO-d$_6$): 1.18-1.27 (m, 6H, 2×Ala-CH$_3$), 2.74-2.82 (m, 2H, N—CH$_2$CH$_2$Ph), 4.04-4.08 (m, 1H, NH), CH$_3$), 3.20-3.32 (d, 2H, NCH$_2$CO), 3.52-3.58 (m, 2H, N—CH$_2$CH$_2$Ph), 4.04-4.08 (m, 1H, α-H), 4.28-4.31 (m, 1H, α-H), 4.99 (m, 2H, Cbz), 6.86-6.89 (d, 1H, J=14.4 Hz, CH=CHCON), 7.04-7.08 (d, 1H, J=14.8 Hz, CH=CHCON), 7.16-7.41 (m, 11H, 2×Ph and NH), 7.50 (d, 1H, NH), 8.16 (d, 1H, NH), 10.72 (s, 1H, NH). MS (ESI) m/z 581 [(M+1)$^+$]. HRMS (ESI) calculated for C$_{29}$H$_{37}$N$_6$O$_7$: 581.2717. Observed m/z 581.272373. Anal. Calcd. for C$_{29}$H$_{36}$N$_6$O$_7$.0.6H$_2$O.0.1hexane: C, 59.25; H, 6.48; N, 14.01. Found: C, 59.27; H, 6.50; N, 13.82.

Example 3N

N$^2$—(N-Benzyloxycarbonylalanylalanyl)-N$^1$-carbamoylmethyl-N$^1$-trans-(3-phenylbenzylcarbamoylpropenoyl)hydrazine (Cbz-Ala-Ala-AAsn-CH=CH—CON(Bzl)Ph). This compound was obtained using the HOBt/EDC coupling method and purified by column chromatography on silica gel using 10% MeOHICH$_2$Cl$_2$ as the eluent to give a white powder (14% yield). $^1$H-NMR (DMSO-d$_6$): 1.20-1.21 (d, 3H, Ala-CH$_3$), 1.26 (d, 3H, Ala-CH$_3$), 3.31 (s, 2H, NCH$_2$CO), 4.04-4.08 (m, 1H, α-H), 4.28-4.31 (m, 1H, α-H), 4.96-4.99 (d, 4H, N—CH$_2$-Ph and Cbz), 6.57-6.61 (d, 1H, J=15.2 Hz, CH=CHCON), 7.14-7.45 (m, 18H, CH=CHCON and 3×Ph and 2×NH), 8.16 (d, 1H, NH), 10.71 (s, 1H, NH). MS (ESI) m/z 629 [(M+1)$^+$]. HRMS (ESI) calculated for C$_{33}$H$_{37}$N$_6$O$_7$: 629.2691. Observed m/z 629.272373. Anal. Calcd. for C$_{33}$H$_{36}$N$_6$O$_7$.0.09H$_2$O.0.17hexane: C, 62.15; H, 6.05; N, 12.83. Found: C, 62.15; H, 5.96; N, 12.66.

Example 3O

N$^2$—(N-Benzyloxycarbonylalanylalanyl)-N$^1$-carbamoylmethyl-N$^1$-trans-(3-dibenzylcarbamoylpropenoyl)hydrazine (Cbz-Ala-Ala-AAsn-CH=CH—CON(Bzl)$_2$). This compound was obtained using the HOBt/EDC coupling method and purified by column chromatography on silica gel using 10% MeOH/CH$_2$Cl$_2$ as the eluent to give-a white powder (34% yield). $^1$-NMR (DMSO-d$_6$): 1.19 (d, 3H, Ala-CH$_3$), 1.26 (d, 3H, Ala-CH$_3$), 3.31 (s, 2H, NCH$_2$CO), 4.04-4.08 (m, 1H, α-H), 4.28-4.31 (m, 1H, α-H), 4.56 (s, 2H, N—CH$_2$-Ph), 4.63 (s, 2H, N—CH$_2$-Ph), 5.00 (m, 2H, Cbz), 7.13-7.41 (m, 17H, CH=CHCON and CH=CHCON and 3×Ph and NH), 7.48 (s, 1H, NH), 8.14 (d, 1H, NH), 10.71 (s, 1H, NH). MS (ESI) m/z 643 [(M+1)$^+$]. HRMS (ESI) calculated for C$_{34}$H$_{39}$N$_6$O$_7$: 643.2843. Observed m/z 643.288023. Anal. Calcd. for C$_{34}$H$_{38}$N$_6$O$_7$: C, 63.54; H, 5.96; N, 13.08. Found: C, 63.75; H, 6.02; N, 12.81.

Example 3P

N$^2$—(N-Benzyloxycarbonylalanylalanyl)-N$^1$-trans-(3-benzyl-(4-methoxybenzyl)carbamoyl)propenoyl-N$^1$-carbamoylmethylhydrazine (Cbz-Ala-Ala-AAsn-CH=CH—CON(Bzl-4-OMe)Bzl). This compound was obtained using the HOBt/EDC coupling method and purified by recrystallization from 10% MeOH/CH$_2$Cl$_2$ to give a yellow powder (9%. yield). $^1$H-NMR (DMSO-d$_6$): 1.19-1.20 (d, 3H, Ala-CH$_3$), 1.26-1.28 (d, 3H, Ala-CH$_3$), 3.32 (s, 2H, NCH$_2$CO), 3.72 (s, 3H, OCH$_3$), 4.04-4.09 (m, 1H, α-H), 4.28-4.32 (m, 1H, α-H), 4.48-4.54 (d, 2H, N—CH$_2$-Ph), 4.54-4.59 (d, 2H, N—CH$_2$-Ph), 5.00 (m, 2H, Cbz), 6.84-6.91 (2×d, 2H, Ph), 7.06-7.08 (d, 1H, J=8.8 Hz, CH=CHCON), 7.12-7.42 (m, 14H, CH=CHCON and 3×Ph and NH), 7.50 (s, 1H, NH), 8.16-8.17 (d, 1H, NH), 10.71 (s, 1H, NH). MS (ESI) m/z 673 [(M+1)$^+$]. HRMS (ESI) calculated for C$_{35}$H$_{41}$N$_6$O$_8$: 673.3001. Observed m/z 673.298588. Anal. Calcd. for C$_{35}$H$_{40}$N$_6$O$_8$.0.5CH$_2$Cl$_2$: C, 59.61; H, 5.78; N, 11.75. Found: C, 59.76; H, 5.71; N, 11.54.

Example 3Q

N²—(N-Benzyloxycarbonylalanylalanyl)-N¹-trans-(3-benzyl(4-fluorobenzyl)carbamoylpropenoyl)-N¹-carbamoylmethylhydrazine (Cbz-Ala-Ala-AAsn-CH=CH—CON(Bzl-4-F)Bzl). This compound was obtained using the HOBt/EDC coupling method and purified by column chromatography using 10% MeOH/CH$_2$Cl$_2$ as the eluent. Recrystallization with hexane/EtOAc gave a white powder (11% yield). $^1$H-NMR (DMSO-d$_6$): 1.19-1.20 (d, 3H, Ala-CH$_3$), 1.26-1.28 (d, 3H, Ala-CH$_3$), 3.32 (s, 2H, NCH$_2$CO), 4.05-4.09 (m, 1H, α-H), 4.28-4.32 (m, 1H, α-H), 4.35 (s, 2H, CH$_2$Ph), 4.62-4.64 (d, 2H, N—CH$_2$-Ph), 5.00 (m, 2H, Cbz), 7.09-7.34 (m, 17H, CH=CHCON and CH=CHCON and 3×Ph and NH), 7.40-7.42 (d, 1H, NH), 7.50 (s, 1H, NH), 8.15-8.16 (d, 1H, NH), 10.71 (s, 1H, NH). MS (ESI) m/z 661 [(M+1)$^+$]. HRMS (ESI) calculated for C$_{34}$H$_{38}$N$_6$O$_7$F: 661.2781. Observed m/z 661.278601. Anal. Calcd. for C$_{34}$H$_{37}$N$_6$O$_7$F.0.35H$_2$O: C, 61.22; H, 5.70; N, 12.60. Found: C, 61.16; H, 5.71; N, 12.60.

Example 3R

N²—(N-Benzyloxycarbonylalanylalanyl)-N¹-carbamoylmethyl-N¹-trans-(3-bis-(2-furylmethyl)carbamoylpropenoyl)hydrazine (Cbz-Ala-Ala-AAsn-CH=CH—CON(CH$_2$-2-furyl)$_2$). This compound was obtained using the HOBt/EDC coupling method. The product was isolated by chromatography with 10% MeOH/CH$_2$Cl$_2$ as the eluent and recrystallized from hexane/EtOAc to give a white powder (34% yield). $^1$H-NMR (DMSO-d$_6$): 1.18-1.27 (m, 6H, 2×Ala-CH$_3$), 2.92 (d, 1H, furyl), 3.28-3.38 (m, 4H, N-CH$_2$ and NCH$_2$CO and furyl), 3.47-3.50 (d, 1H, N—CH$_2$), 3.99-4.07 (m, 2H, α-H and N—CH$_2$), 4.30-4.49 (m, 2H, α-H and N—CH$_2$), 4.99 (m, 2H, Cbz), 6.02 (s, 1H, NH), 6.11 (s, 1H, NH), 6.31(s, 1H, CH=CHCON), 6.39 (s, 1H, CH=CHCON), 6.55 (t, 1H, furyl), 7.12 (s, 1H, NH), 7.32 (m, 5H, Ph), 7.41-7.59 (m, 3H, furyl), 8.21 (d, 1H, NH), 10.58 (s, 1H, NH). MS (ESI) m/z 623 [(M+1)$^+$]. HRMS (ESI) calculated for C$_{30}$H$_{35}$N$_6$O$_9$: 623.2486. Observed m/z 623.2466. Anal. Calcd. for C$_{30}$H$_{34}$N$_6$O$_9$.1H$_2$O: C, 56.24; H, 5.66; N, 13.12. Found: C, 56.38; H, 5.58; N, 13.15.

Example 3S

N²—(N-Benzyloxycarbonylalanylalanyl)-N¹-trans-(3-benzyl-2-naphthylmethylcarbamoylpropenoyl)-N¹-carbamoylmethylhydrazine (Cbz-Ala-Ala-AAsn-CH=CH—CON(Bzl)-2-CH$_2$-Napth). This compound was obtained using the HOBt/EDC coupling method and purified by column chromatography on silica gel using 10% MeOH/CH$_2$Cl$_2$ as the eluent and then recrystallized from EtOAc/hexane to give a yellow powder (11% yield). $^1$H-NMR (DMSO-d$_6$): 1.18-1.28 (m, 6H, 2×Ala-CH$_3$), 3.29-3.32 (d, 2H, NCH$_2$CO), 4.04-4.08 (m, 1H, α-H), 4.28-4.31 (m, 1H, α-H), 4.63-4.69 (d, 2H, N—CH$_2$), 4.73-4.80 (d, 2H, N—CH$_2$), 4.99 (m, 2H, Cbz), 7.14-7.48 (m, 18H, naphthyl and 2×Ph and CH=CHCON and CH=CHCON and 2×NH), 7.84-7.90 (m, 3H, naphthyl), 8.15 (d, 1H, NH), 10.72 (s, 1H, NH). MS (ESI) m/z 693 [(M+1)$^+$]. HRMS (ESI) calculated for C$_{38}$H$_{41}$N$_6$O$_7$: 693.2998. Observed m/z 693.303673. Anal. Calcd. for C$_{38}$H$_{40}$N$_6$O$_7$.0.63H$_2$O: C, 64.82; H, 5.91; N, 11.94. Found: C, 64.83; H, 6.02; N, 11.83.

Example 3T

N²—(N-Benzyloxycarbonylalanylalanyl)-N¹-trans-(3-benzyl-1-naphthylmethylcarbamoylpropenoyl)-N¹-carbamoylmethylhydrazine (Cbz-Ala-Ala-AAsn-CH=CH—CON(Bzl)-1-CH$_2$-Napth). This compound was obtained using the HOBt/EDC coupling method and purified by column chromatography on silica gel using 10% MeOH/CH$_2$Cl$_2$ as the eluent and then recrystallized from EtOAc/hexane to give a white powder (17% yield). $^1$H-NMR (DMSO-d$_6$): 1.19-1.29 (m, 6H, 2×Ala-CH$_3$), 3.30-3.32 (d, 2H, NCH$_2$CO), 4.04-4.08 (m, 1H, α-H), 4.29-4.33 (m, 1H, α-H), 4.64-4.67 (d, 2H, N—CH$_2$), 4.99 (m, 2H, Cbz), 5.06-5.17 (d, 2H, N—CH$_2$), 7.14-7.48 (m, 18H, naphthyl and 2×Ph and CH=CHCON and CH=CHCON and 2×NH), 7.84-7.90 (m, 3H, naphthyl), 8.15 (d, 1H, NH), 10.72 (s, 1H, NH). Anal. Calcd. for C$_{38}$H$_{40}$N$_6$O$_7$.0.2H$_2$O: C, 65.54; H, 5.85; N, 12.07. Found: C, 65.54; H, 5.93; N, 11.81.

Example 3U

N²—(N-Benzyloxycarbonylalanylalanyl)-N¹-carbamoylmethyl-N¹-trans-(3-(3,4-dihydro-2H-quinolin-1-yloxo)propenoyl)hydrazine (Cbz-Ala-Ala-AAsn-CH=CH—CO-tetrahydroquinoline). This compound was obtained using the HOBt/EDC coupling method and purified by column chromatography on silica gel using 10% MeOH/CH$_2$Cl$_2$ as the eluent and then recrystallized from EtOAc/hexane to give a yellow powder (28% yield). $^1$H-NMR (DMSO-d$_6$): 1.18-1.27 (m, 6H, 2×Ala-CH$_3$), 1.87 (m, 2H, N—CH$_2$—CH$_2$—CH$_2$), 2.70 (t, 2H, N—CH$_2$—CH$_2$—CH$_2$), 3.29-3.32 (d, 2H, NCH$_2$CO), 3.73 (m, 2H, N—CH$_2$—CH$_2$), 4.02-4.06 (m, 1H, α-H), 4.31 (m, 1H, α-H), 4.99 (m, 2H, Cbz), 7.02-7.07 (dd, 2H, J=14.8 Hz, CH=CHCON), 7.15-7.41 (m, 11H, quinoline and Ph and NH and CH=CHCON), 7.49 (s, 1H, NH), 8.16 (d, 1H, NH), 10.73 (s, 1H, NH). MS (ESI) m/z 579 [(M+1)$^+$]. HRMS (ESI) calculated for C$_{29}$H$_{35}$N$_6$O$_7$: 579.2525. Observed m/z 579.2567. Anal. Calcd. for C$_{29}$H$_{34}$N$_6$O$_7$.0.7H$_2$O: C, 58.91; H, 6.03; N, 14.21. Found: C, 58.87; H, 6.00; N, 14.24.

Example 3V

N²—(N-Benzyloxycarbonylalanylalanyl)-N¹-carbamoylmethyl-N¹-trans-(3-(3,4-dihydro-2H-quinolin-1-yloxo)propenoyl)hydrazine (Cbz-Ala-Ala-AAsn-CH=CH—CO-tetrahydroisoquinoline). This compound was obtained using the HOBt/EDC coupling method and purified by column chromatography on silica gel using 10% MeOH/CH$_2$Cl$_2$ as the eluent and then recrystallized from EtOAc/hexane to give a yellow powder (28% yield). $^1$H-NMR (DMSO-d$_6$): 1.18-1.27 (m, 6H, 2×Ala-CH$_3$), 1.87 (m, 2H, N—CH$_2$—CH$_2$—CH$_2$), 2.70 (t, 2H, N—CH$_2$—CH$_2$—CH$_2$), 3.29-3.32 (d, 2H, NCH$_2$CO), 3.73 (m, 2H, N—CH$_2$—CH$_2$), 4.02-4.06 (m, 1H, α-H), 4.31 (m, 1H, α-H), 4.99 (m, 2H, Cbz), 7.02-7.07 (dd, 2H, J=14.8 Hz, CH=CHCON), 7.15-7.41 (m, 11H, quinoline and Ph and NH and CH=CHCON), 7.49 (s, 1H, NH), 8.16 (d, 1H, NH), 10.73 (s, 1H, NH). MS (ESI) m/z 579 [(M+1)$^+$]. HRMS (ESI) calculated for C$_{29}$H$_{35}$N$_6$O$_7$: 579.2525. Observed m/z 579.2567. Anal. Calcd. for C$_{29}$H$_{34}$N$_6$O$_7$.0.9H$_2$O.0.1hexane: C, 58.92; H, 6.21; N, 13.92. Found: C, 58.81; H, 6.04; N, 13.79.

Example 3W

N$^2$—(N-Benzyloxycarbonylalanylalanyl)-N$^1$-carbamoyl-methyl-N$^1$-trans-(3-(2,3-dihydroindol-1-yloxo)propenoyl)hydrazine (Cbz-Ala-Ala-AAsn-CH=CH—CO-indoline). This compound was obtained using the HOBt/EDC coupling method and purified by column chromatography on silica gel using 10% MeOH/CH$_2$Cl$_2$ as the eluent and then recrystallized from EtOAc/hexane to give a bright yellow, flaky powder (15% yield). $^1$H-NMR (DMSO-d$_6$): 1.18-1.19 (d, 3H, Ala-CH$_3$), 1.27-1.28 (d, 3H, Ala-CH$_3$), 3.15 (t, 2H, N—CH$_2$CH$_2$), 3.20-3.31 (d, 2H, NCH$_2$CO), 4.02-4.06 (m, 1H, α-H), 4.06 (t, 2H, N—CH$_2$—CH$_2$), 4.31 (m, 1H, α-H), 4.99 (m, 2H, Cbz), 7.02 (t, 1H, indoline-H), 7.13-7.41 (m, 10H, indoline and Ph and NH and CH=CHCON and CH=CHCON), 7.52 (s, 1H, NH), 8.13 (d, 1H, NH), 8.15-8.16 (d, 1H, indoline-H), 10.76 (s, 1H, NH). MS (ESI) m/z 565 [(M+1)$^+$]. HRMS (ESI) calculated for C$_{28}$H$_{33}$N$_6$O$_7$: 565.2416. Observed m/z 565.241073. Anal. Calcd. for C$_{28}$H$_{32}$N$_6$O$_7$·0.4H$_2$O: C, 58.82; H, 5.78; N, 14.70. Found: C, 58.87; H, 5.82; N, 14.68.

Example 3X

N$^2$—(N-Benzyloxycarbonylalanylalanyl)-N$^1$-carbamoyl-methyl-N$^1$-trans-(3-(1,3-dihydroisoindol-2-yloxo)propenoyl)hydrazine (Cbz-Ala-Ala-AAsn-CH=CH—CO-isoindoline). This compound was obtained using the HOBt/EDC coupling method and purified by column chromatography on silica gel using 10% MeOH/CH$_2$Cl$_2$ as the eluent and then recrystallized from EtOAc/hexane to give a bright yellow, flaky powder (15% yield). $^1$H-NMR (DMSO-d$_6$): 1.18-1.19 (d, 3H, Ala-CH$_3$), 1.27-1.28 (d, 3H, Ala-CH$_3$), 3.20-3.31 (d, 2H, NCH$_2$CO), 4.04-4.07 (m, 1H, α-H), 4.29-4.33 (m, 1H, α-H), 4.72 (s, 2H, NCH$_2$), 4.99 (m, 2H, Cbz and NCH$_2$), 7.11-7.32 (m, 11H, indoline and Ph and NH and CH=CHCON and CH=CHCON), 7.39 (d, 1H, NH), 7.52 (s, 1H, NH), 8.14 (d, 1H, NH), 10.76 (s, 1H, NH). MS (ESI) m/z 565 [(M+1)$^+$]. HRMS (ESI) calculated for C$_{28}$H$_{33}$N$_6$O$_7$: 565.2414. Observed m/z 565.241073. Anal. Calcd. for C$_{28}$H$_{32}$N$_6$O$_7$·0.3H$_2$O: C, 59.00; H, 5.76; N, 14.74. Found: C, 59.04; H, 5.54; N, 14.56.

Example 3Y

N$^2$—(N-Benzyloxycarbonylalanylalanyl)-N$^1$-carbamoyl-methyl-N$^1$-trans-(3-(4-phenyl-5,6-dihydro-2H-pyridin-1-yloxo)propenoyl)hydrazine (Cbz-Ala-Ala-AAsn-CH=CH—CO-(4-Ph-Py)). This compound was obtained using the HOBt/EDC coupling method and purified by column chromatography using 10% MeOH/CH$_2$Cl$_2$ as the eluent to give a white solid (11% yield). $^1$H-NMR (DMSO-d$_6$): 1.15-1.26 (m, 6H, 2×Ala-CH$_3$), 2.56 (s, 2H, pyridyl-CH$_2$), 3.30-3.32 (d, 2H, NCH$_2$CO), 3.74 (t, 2H, pyridyl-CH$_2$), 4.02-4.07 (m, 1H, α-H), 4.17 (s, 2H, pyridyl-CH$_2$), 4.27-4.35 (m, 1H, α-H), 4.99 (m, 2H, Cbz), 6.16 (s, 1H, pyridyl-CH=), 7.02-7.06 (d, 1H, J=15.2 Hz, CH=CHCON), 7.19 (s, 1H, NH), 7.23-7.42 (m, 11H, CH=CHCON and 2×Ph), 7.51 (d, 1H, NH), 8.14-8.15 (d, 1H, NH), 10.72 (s, 1H, NH). MS (ESI) m/z 605 [(M+1)$^+$]. HRMS (ESI) calculated for C$_{31}$H$_{37}$N$_6$O$_7$: 605.2757. Observed m/z 605.272373. Anal. Calcd. for C$_{31}$H$_{36}$N$_6$O$_7$·1H$_2$O: C, 59.80; H, 6.15; N, 13.50. Found: C, 59.71; H, 6.02; N, 13.27.

Example 3Z

N$^2$—(N-Benzyloxycarbonylalanylalanyl)-N$^1$-carbamoyl-methyl-N$^1$-trans-(3-methyl-(1-methylphenethylcarbamoyl)phenylethylcarbamoylpropenoyl)hydrazine (Cbz-Ala-Ala-AAsn-CH=CH—CO-Phe(Me)-N(Me)(CH$_2$)$_2$Ph). This compound was obtained using the HOBt/EDC coupling method and purified by column chromatography using 10% MeOH/CH$_2$Cl$_2$ as the eluent. Recrystallization with hexane/EtOAc gave a yellow powder (11% yield). $^1$H-NMR (DMSO-d$_6$): 1.19-1.20 (d, 3H, Ala-CH$_3$), 1.26-1.28 (d, 3H, Ala-CH$_3$), 2.61-2.95 (m, 10H, Phe-CH$_2$ and CH$_2$Ph and 2×N-Me), 3.32 (s, 2H, NCH$_2$CO), 3.62 (m, 2H, N—CH$_2$), 4.05-4.09 (m, 1H, α-H), 4.28-4.32 (m, 1H, α-H), 4.99 (m, 2H, Cbz), 5.52 (m, 1H, α-H), 6.93-7.32 (m, 18H, CH=CHCON and CH=CHCON and 3×Ph and NH), 7.40-7.42 (d, 1H, NH), 7.50 (s, 1H, NH), 8.15-8.16 (d, 1H, NH), 10.71 (s, 1H, NH). MS (ESI) m/z 607 [(M−HN(CH$_3$)CH$_2$CH$_2$Ph+1, 100%)$^+$]. HRMS (ESI) calculated for C$_{39}$H$_{48}$N$_7$O$_8$: 742.3575. Observed m/z 742.3564. Anal. Calcd. for C$_{39}$H$_{47}$N$_7$O$_8$·1.23H$_2$O·0.3hexane: C, 62.09; H, 6.78; N, 12.42. Found: C, 61.99; H, 6.62; N, 12.49.

Example 3AA trans-N$^2$—(N-Benzyloxycarbonylalanylalanyl)-N$^1$-carbamoylmethyl-N$^1$-trans-(3-benzoylpropenoyl)hydrazine (Cbz-Ala-Ala-AAsn-CH=CH—COPh). This compound was obtained using the HOBt/EDC coupling method starting from the peptide precursor Z-Ala-Ala-NHNHCH$_2$CONH$_2$ and commercially available trans-3-benzoylacrylic acid. The workup omitted the NaHCO$_3$ washings. The crude product was purified by column chromatography on silica gel using 10% MeOH/CH$_2$Cl$_2$ as the eluent and then washed with EtOAc to give a white powder (39% yield). $^1$H-NMR (DMSO-d$_6$): 1.18-1.27 (m, 6H, 2×Ala-CH$_3$), 3.20-3.32 (d, 2H, NCH$_2$CO), 3.98-4.05 (m, 1H, α-H), 4.26-4.29 (m, 1H, α-H), 4.99 (m, 2H, Cbz), 7.14-7.21 (m, 2H, CH=CHCOPh and NH), 7.32-7.35 (m, 5H, Ph), 7.54 (t, 2H, Ph), 7.69 (t, 1H, Ph), 7.76-7.80 (d, 1H, J=15.6 Hz, CH=CHCOPh), 7.97-7.99 (d, 2H, Ph), 8.14 (d, 1H, NH), 10.77 (s, 1H, NH). MS (ESI) m/z 524 [(M+1)$^+$]. HRMS (ESI) calculated for C$_{26}$H$_{30}$N$_5$O$_7$: 524.2056. Observed m/z 524.2145. Anal. Calcd. for C$_{26}$H$_{29}$N$_5$O$_7$: C, 59.65; H, 5.58; N, 13.38. Found: C, 59.42; H, 5.50; N, 13.16.

Example 3BB

N$^2$—(N-Benzyloxycarbonylalanylalanyl)-N$^1$-carbamoyl-methyl-N$^1$-trans-trans-hexa-2,4-dienoylhydrazine (Cbz-Ala-Ala-AAsn-CH=CHCH=CHCH$_3$). This compound was synthesized by coupling the peptide precursor Z-Ala-Ala-NHNHCH$_2$CONH$_2$ and commercially available 2,4-hexadienoic acid using HOBt/EDC and was purified by column chromatography on silica gel using 10% MeOH/CH$_2$Cl$_2$ as the eluent and then recrystallized from CH$_2$Cl$_2$/hexane to give a white powder (14% yield). $^1$H-NMR (DMSO-d$_6$): 1.18-1.24 (m, 6H, 2×Ala-CH$_3$), 1.79 (d, 3H, CH$_3$—CH=CH—), 3.30-3.32 (d, 2H, NCH$_2$CO), 4.06 (m, 1H, α-H), 4.25 (m, 1H, α-H), 4.98 (m, 2H, Cbz), 6.19 (m, 3H, CH$_3$—CH=CH—CH), 7.21 (m, 2H, NH and CH=CH—CO), 7.33 (m, 5H, Ph), 7.5 (d, 1H, NH), 8.19 (d, 1H, NH), 10.53 (s, 1H, NH). MS (ESI) m/z 460 [(M+1)$^+$]. HRMS (ESI) calculated for C$_{22}$H$_{30}$N$_5$O$_6$: 460.2157. Observed m/z 460.219609. Anal. Calcd. for $C_{22}H_{29}N_5O_6.0.3EtOAc$: C, 57.39; H, 6.44; N, 14.42. Found: C, 57.14; H, 6.72; N, 14.44.

Example 3CC $N^2$—(N-Benzyloxycarbonylalanylalanyl)-$N^1$-carbamoylmethyl-$N^1$-trans-(3-(2-furyl)propenoyl)hydrazine (Cbz-Ala-Ala-AAsn-CH=CH-2-furyl). This compound was obtained using the HOBt/EDC coupling method starting with the peptide precursor Cbz-Ala-Ala-NHNHCH$_2$CONH$_2$ and commercially available 2-furylacrylic acid and purified by column chromatography on silica gel using 10% MeOH/CH$_2$Cl$_2$ as the eluent. Recrystallization from hexane/EtOAc gave a white powder (23% yield). $^1$H-NMR ((CD$_3$)CO): 1.37 (d, 3H, Ala-CH$_3$), 1.44 (d, 3H, Ala-CH$_3$), 2.88 (s, 2H, NCH$_2$CO), 4.24 (m, 1H, α-H), 4.52 (m, 1H, α-H), 5.10 (m, 2H, Cbz), 6.41 (m, 1H, furyl-H), 6.55 (m, 1H, furyl-H), 6.68 (m, 1H, CH=CH—CON), 6.88 (s, 2H, NH$_2$), 7.31-7.36 (m, 5H, Ph), 7.39-7.43 (d, 1H, J=15.6 Hz, CH=CHCON), 7.48 (s, 1H, NH), 7.65 (s, 1H, furyl-H), 7.81 (s, 1H, NH), 9.83 (s, 1H, NH). MS (ESI) m/z 486 [(M+1)$^+$]. HRMS (ESI) calculated for $C_{23}H_{28}N_5O_7$: 486.1957. Observed m/z 486.198874. Anal. Calcd. for $C_{23}H_{27}N_5O_7.0.3H_2O.0.1hexane$: C, 56.14; H, 5.91; N, 13.87. Found: C, 56.09; H, 5.85; N, 13.78.

Example 3DD $N^2$—(N-Benzyloxycarbonylalanylalanyl)-$N^1$-carbamoylmethyl-$N^1$-trans-(3-(3-pyridyl)propenoyl)hydrazine (Cbz-Ala-Ala-AAsn-CH=CH-3-Py). This compound was obtained using the HOBt/EDC coupling method starting from the peptide precursor Z-Ala-Ala-NHNHCH$_2$CONH$_2$ and commercially available 3-pyridyl acrylic acid. Upon completion of the reaction sat. NaHCO$_3$ was added, and the volatiles were evaporated. Without further workup, the crude product was chromatographed on silica gel using 10% to 20% MeOH/CH$_2$Cl$_2$ as the eluent and recrystallized from hexane/EtOAc to give a white powder (7% yield). $^1$H-NMR ((CD$_3$)CO): 1.37 (d, 3H, Ala-CH$_3$), 1.44 (d, 3H, Ala-CH$_3$), 2.91 (s, 2H, NCH$_2$CO), 4.24 (m, 1H, α-H), 4.42 (m, 1H, α-H), 5.10 (m, 2H, Cbz), 6.53 (m, 1H, pyridine-H), 6.68 (d, 1H, CH=CHCON), 7.31-7.36 (m, 5H, Ph), 7.59-7.64 (m, 1H, NH and CH=CHCON), 7.98 (s, 1H, pyridine-H), 8.32 (s, 1H, NH), 7.53 (s, 1H, pyridine-H), 8.90 (s, 1H, pyridine-H), 10.08 (s, 1H, NH). MS (ESI) m/z 497 [(M+1)$^+$]. HRMS (ESI) calculated for $C_{24}H_{29}N_6O_6$: 497.2078. Observed m/z 497.2149. Anal. Calcd. for $C_{24}H_{28}N_6O_6.1H_2O$: C, 56.02; H, 5.88; N, 16.33. Found: C, 56.21; H, 5.77; N, 16.93.

Example 4

Deblocking of the t-Butyl Protecting Group in the Aza-Asp Peptide Inhibitors. The aza-peptide inhibitors were treated with 1:1 TFA: CH$_2$Cl$_2$ at 0° C. for 1 h and at room temperature for 2 h. TFA and CH$_2$Cl$_2$ were removed under vacuum and the final products were recrystallized from ether/hexanes mostly as white solids.

Example 4A $N^2$—(N-Benzyloxycarbonylvalyl)-$N^1$-carboxymethyl-$N^1$-trans-(3-ethoxycarbonylpropenoyl)hydrazine (Cbz-Val-AAsp-CH=CH—COOEt). $^1$H NMR (DMSO-d$_6$): 0.87 (d, 6H, Val), 1.15-1.23 (m, 3H, OCH$_2$CH$_3$), 1.98 (m, 1H, Val), 3.89 (t, 1H, α-H), 4.13 (q, 2H, OCH$_2$CH$_3$), 5.03 (s, 2H, Cbz), 6.65 (d, 1H, db), 7.28-7.34 (m, 6H, db and Ph), 7.54 (d, 1H, NH), 11.00 (s, 1H, NH). HRMS (FAB) Calcd. for $C_{21}H_{27}N_3O_8$: 449.1798; Observed m/z: 449.1876. Anal. Calcd. for $C_{21}H_{27}N_3O_8.0.29H_2O$: C, 55.47; H, 6.13; N, 9.26. Found: C, 55.47; H, 6.11; N, 9.24.

Example 4B $N^2$—(N-Benzyloxycarbonylvalyl)-$N^1$-trans-(but-2-enoyl)-$N^1$-carboxymethylhydrazine (Cbz-Val-AAsp-CH=CHCH$_3$). HRMS (ESI) Calcd. for $C_{19}H_{25}N_3O_6$; 391.1822; Observed m/z: 391.1797.

Example 4C $N^2$—(N-Benzyloxycarbonylvalyl)-$N^1$-carboxymethyl-$N^1$-trans-(hexa-2,4-dienoyl)hydrazine (Cbz-Val-AAsp-CH=CHCH=CHCH$_3$). $^1$H NMR (DMSO-d$_6$): 0.90 (d, 6H, Val), 1.78 (d, 3H, CH$_3$), 1.97 (m, 1H, Val), 3.87 (t, 1H, α-H), 5.05 (q, 2H, Cbz), 6.14 (m, 2H, db), 6.38 (m, 1H, db), 7.09 (dd, 2H, db), 7.33 (m, 5H, Ph), 7.59 (d, 1H, NH), 10.81 (s, 1H, NH—N). HRMS (ESI) Calcd. for $C_{21}H_{27}N_3O_6$: 417.1978; Observed m/z: 417.1974. Anal. Calcd. for $C_{21}H_{27}N_3O_6.1.43H_2O.0.05TFA$: C, 56.45; H, 6.72; N, 9.36. Found: C, 56.36; H, 6.43; N, 9.66.

Example 4D $N^2$—(N-Benzyloxycarbonylvalyl)-$N^1$-carboxymethyl-$N^1$-trans-(3-phenethylpropenoyl)hydrazine (Cbz-Val-AAsp-CH=CHCH$_2$CH$_2$Ph). HRMS (ESI) Calcd. for $C_{26}H_{31}N_3O_6$: 482.2291; Observed m/z: 482.2301. Anal. Calcd. for $C_{26}H_{31}N_3O_6.0.84H_2O$: C, 62.87; H, 6.63; N, 8.46. Found: C, 62.87; H, 6.51; N, 8.28.

Example 4E $N^2$—(N-Benzyloxycarbonylvalyl)-$N^1$-carboxymethyl-$N^1$-cis-(3-chloropropenoyl)hydrazine (Cbz-Val-AAsp-cis-CH=CH—Cl). $^1$H NMR (DMSO-d$_6$): 0.86 (d, 6H, Val), 1.93 (m, 1H, Val), 3.84 (t, 1H, α-H), 5.01 (s, 2H, Cbz), 6.57 (s, 1H, db), 6.76 (d, 1H, db), 7.29-7.34 (m, 5H, Ph), 7.53 (d, 1H, NH), 10.80 (s, 1H, NH—N). HRMS (ESI) Calcd. for $C_{18}H_{22}N_3O_6Cl$: 411.1275; Observed m/z: 411.1195. Anal. Calcd. for $C_{18}H_{22}N_3O_6Cl.0.04H_2O$: C, 52.40; H, 5.39; N, 1019. Found: C, 52.40; H, 5.46; N, 10.30.

Example 4F $N^2$—(N-Benzyloxycarbonylvalyl)-$N^1$-carboxymethyl-$N^1$-trans-(3-(4-chlorophenyl)propenoyl)hydrazine (Cbz-Val-AAsp-CH=CH-Ph-4-Cl). $^1$H NMR (DMSO-d$_6$): 0.86-0.95 (dd, 6H, Val), 1.94 (m, 1H, Val), 3.84 (t, 1H, α-H), 5.03 (q, 2H, Cbz), 7.27-7.32 (m, 5H, Ph), 7.42 (d, 1H, db), 7.55 (d, 1H, db), 7.77 (m, 4H, Ph-Cl), 10.97 (s, 1H, NH—N). HRMS (ESI) Calcd. for $C_{24}H_{26}N_3O_6Cl$: 488.1588; Observed m/z: 488.1563. Anal. Calcd. for $C_{24}H_{26}N_3O_6Cl.0.29H_2O$: C, 58.45; H, 5.43; N, 8.51. Found: C, 58.46; H, 5.43; N, 8.51.

Example 4G $N^2$—(N-Benzyloxycarbonylvalyl)-$N^1$-trans-(3-butylcarbamoylpropenoyl)-$N^1$-carboxymethylhydrazine (Cbz-Val-AAsp-CH=CH—CONH-nBu). $^1$H NMR (DMSO-d$_6$): 0.83-0.87 (m, 9H, Val and NHCH$_2$CH$_2$CH$_2$CH$_3$), 1.27 (m, 2H, NHCH$_2$CH$_2$CH$_2$CH$_3$), 1.37-1.41 (m, 2H, NHCH$_2$CH$_2$CH$_2$CH$_3$), 1.97 (m, 1H, Val), 3.12 (dd, 2H, NHCH$_2$CH$_2$CH$_2$C$_3$), 3.93 (t, 1H, α-H), 5.03 (q, 2H, Cbz), 6.91 (d, 1H, db), 7.08 (d, 1H, db), 7.28-7.34 (m, 5H, Ph), 7.47

Example 4H

N$^1$-trans-(3-Benzylcarbamoylpropenoyl)-N$^2$—(N-benzyloxycarbonylvalyl)-N$^1$-carboxymethylhydrazine (Cbz-Val-AAsp-CH=CH—CONHCH$_2$Ph). $^1$H NMR (DMSO-d$_6$): 0.85 (d, 6H, Val), 1.97 (m, 1H, Val), 3.96 (t, 1H, α-H), 4.35 (d, 2H, NHCH$_2$Ph), 5.01 (s, 2H, Cbz), 6.97 (d, 1H, db), 7.15 (d, 1H, db), 7.19-7.32 (m, 10H, Ph), 7.47 (d, 1H, NH), 8.91 (t, 1H, NHCH$_2$Ph), 10.94 (s, 1H, NH—N). HRMS (ESI) Calcd. for C$_{26}$H$_{30}$N$_4$O$_7$: 510.2193; Observed m/z: 510.2208. Anal. Calcd. for C$_{26}$H$_{30}$N$_4$O$_7$.0.56H$_2$O: C, 59.98; H, 6.02; N, 10.79. Found: C, 59.99; H, 6.08; N, 10.76.

Example 4I

N$^2$—(N-Benzyloxycarbonylglutamylvalyl)-N$^1$-carboxymethyl-N$^1$-trans-(3-ethoxycarbonylpropenoyl)hydrazine (Cbz-Glu-Val-AAsp-CH=CH—COOEt). $^1$H NMR (DMSO-d$_6$): 0.84 (m, 6H, Val), 1.20-1.21 (t, 3H, OCH$_2$CH$_3$), 1.70-2.10 (m, 3H, Val, Glu), 2.21 (m, 2H, Glu), 2.40 (CH=CH—COOEt) 4.05-4.22 (m, 4H, NCH$_2$COOH and OCH$_2$CH$_3$), 4.50-4.60 (m, 2H, α-H), 5.05 (m, 2H, Cbz), 7.12 (CO—CH=CH—COOEt) 7.20-7.40 (m, 5H, Ph), 7.60 (1H, NH), 7.85 (m, 2H, NH), 11.00 (m, COOH). HRMS (FAB) Calcd. for C$_{26}$H$_{35}$N$_4$O$_{11}$: 579.2302; Observed m/z 579.2342. Anal. Calcd. for C$_{26}$H$_{34}$N$_4$O$_{11}$: C, 53.97; H, 5.92; N, 9.68. Found: C, 54.30; H, 6.12; N, 9.47.

Example 4J

N$^2$—(N-Benzyloxycarbonylaspartylglutamylthreonyl)-N$^1$-carboxylmethyl-N$^1$-trans-(3-ethoxycarbonylpropenoyl)hydrazine (Cbz-Asp-Glu-Val-AAsp-CH=CH—COOEt). $^1$H NMR (DMSO-d$_6$): 0.86 (d, 6H, Val CH$_3$), 1.21 (t, 3H, OEt), 1.75 and 1.98 (d of m, 2H, Glu CH$_2$), 1.85 (m, 1H, Val CH), 2.18 (m, 2H, Glu CH$_2$), 2.47 and 2.60 (d of m, 2H, Asp CH$_2$), 3.32 (s, 2H, AAsp CH$_2$), 4.15 (q, 2H, OEt), 4.31 (m, 3H, α-H), 5.00 (s, 2H, Z), 6.58 (d, 1H, CH=CH), 7.20-7.35 (m, 7H, CH=CH, Ph and NH), 7.58 (d, 1H, NH), 7.97 (m, 2H, NH), 10.95 (b, 3H, COOH). HRMS (FAB) calcd. for C$_{30}$H40N$_5$O$_{14}$: 694.2572; Observed m/z 694.2599. Anal. Calcd. for C$_{30}$H$_{39}$N$_5$O$_{14}$: C, 51.95; H, 5.67; N, 10.10. Found: C, 51.65; H, 5.71; N, 10.03.

Example 4K

N$^2$—(N-Benzyloxycarbonylaspartylglutamylvalyl)-N$^1$-carboxylmethyl-N$^1$-cis-(3-ethoxycarbonylpropenoyl)hydrazine (Cbz-Asp-Glu-Val-AAsp-cis-CH=CH—COOEt). $^1$H NMR (DMSO-d$_6$): 0.85 (d, 6H, Val), 1.18 (t, 3H, OCH$_2$CH$_3$), 1.74 (m, 1H, Glu), 1.86 (m, 1H, Glu), 1.95 (m, 1H, Val), 2.18 (m, 2H, Glu), 2.45 (dd, 1H, Asp), 2.61 (dd, 1H, Asp), 4.09 (t, 1H, α-H), 4.16 (q, 2H, OCH$_2$CH$_3$), 4.33 (m, 2H, α-H), 5.01 (s, 2H, Cbz), 6.61 (d, 1H, db), 7.25 (d, 1H, db), 7.33 (s, 5H, Ph), 7.62 (d, 1H, NH), 7.93 (t, 2H, NH), 11.05 (s, 1H, NH—N). HRMS (ESI) Calcd. for C$_{30}$H$_{39}$N$_5$O$_{14}$: 693.2566; Observed m/z: 693.2516. Anal. Calcd. for C$_{30}$H$_{39}$N$_5$O$_{14}$.1H$_2$O: C, 50.63; H, 5.81; N, 9.67. Found: C, 50.61; H, 5.82; N, 9.67.

Example 4L

N$^1$-trans-(3-Benzyloxycarbonylpropenoyl)-N$^2$—(N-benzyloxycarbonylaspartylglutamylvalyl)-N$^1$-carboxymethylhydrazine (Cbz-Asp-Glu-Val-AAsp-CH=CH—COOCH$_2$Ph). $^1$H NMR (DMSO-d$_6$): 0.81 (d, 6H, Val), 1.74 (m, 1H, Glu), 1.86 (m, 1H, Glu), 1.95 (m, 1H, Val), 2.18 (m, 2H, Glu), 2.45 (dd, 1H, Asp), 2.61 (dd, 1H, Asp), 4.13 (t, 1H, α-H), 4.29 (m, 2H, α-H), 4.99 (s, 2H, Cbz), 5.18 (s, 2H, Bzl), 6.69 (d, 1H, db), 7.25-7.37 (m, 11H, Ph, and db), 7.60 (d, 1H, NH), 7.93 (t, 2H, NH), 11.02 (s, 1H, NH—N). HRMS (ESI) Calcd. for C$_{35}$H$_{41}$N$_5$O$_{14}$: 755.2728; Observed m/z: 755.2631. Anal. Calcd. for C$_{35}$H$_{41}$N$_5$O$_{14}$.0.59H$_2$O: C, 54.86; H, 5.55; N, 9.14. Found: C, 54.86; H, 5.67; N, 9.11.

Example 4M

N$^1$-trans-(3-Benzylcarbamoylpropenoyl)-N$^2$—(N-benzyloxycarbonylaspartylglutamylvalyl)-N$^1$-carboxymethylhydrazine (Cbz-Asp-Glu-Val-AAsp-CH=CH—CONHCH$_2$Ph). $^1$H NMR (DMSO-d$_6$): 0.85 (t, 6H, Val), 1.75 (m, 1H, Glu), 1.88 (m, 1H, Glu), 2.01 (m, 1H, Val), 2.19 (m, 2H, Glu), 2.48 (dd, 1H, Asp), 2.61 (dd, 1H, Asp), 4.17 (t, 1H, α-H), 4.30 (m, 2H, α-H), 4.35 (d, 2H, NHCH$_2$Ph), 5.00 (s, 2H, Cbz), 6.96 (d, 1H, db), 7.12 (d, 1H, db), 7.21-7.32 (m, 10H, Ph), 7.58 (d, 1H, NH), 7.90 (d, 1H, NH), 7.96 (d, 1H, NH), 8.92 (t, 1H, NHCH$_2$Ph), 10.97 (s, 1H, NH—N). HRMS (ESI) Calcd. for C$_{35}$H$_{42}$N$_6$O$_{13}$: 754.2888; Observed m/z: 754.2853. Anal. Calcd. for C$_{35}$H$_{42}$N$_6$O$_{13}$.1.63H$_2$O: C, 53.61; H, 5.82; N, 10.72. Found: C, 53.82; H, 5.74; N, 10.42.

Example 4Q

N$^2$—(N-Benzyloxycarbonylaspartylglutamylvalyl)-N$^1$-carboxymethyl-N$^1$-trans-(3-phenethylcarbamoylpropenoyl)hydrazine (Cbz-Asp-Glu-Val-AAsp-CH=CH—CONHCH$_2$CH$_2$Ph). $^1$H NMR (DMSO-d$_6$): 0.87 (t, 6H, Val), 1.75 (m, 1H, Glu), 1.89 (m, 1H, Glu), 2.01 (m, 1H, Val), 2.21 (m, 2H, Glu), 2.46 (dd, 1H, Asp), 2.62 (dd, 1H, Asp), 2.73 (t, 2H, NHCH$_2$CH$_2$Ph), 3.73 (d, 2H, NHCH$_2$CH$_2$Ph), 4.18 (t, 1H, α-H), 4.32 (m, 2H, α-H), 5.01 (s, 2H, Cbz), 6.89 (d, 1H, db), 7.08 (d, 1H, db), 7.16-7.32 (m, 10H, Ph), 7.59 (d, 1H, NH), 7.89 (d, 1H, NH), 7.98 (d, 1H, NH), 8.52 (t, 1H, NHCH$_2$CH$_2$Ph), 10.97 (s, 1H, NH—N). HRMS (ESI) Calcd. for C$_{36}$H$_{44}$N$_6$O$_{13}$: 768.3044; Observed m/z: 768.2949. Anal. Calcd. for C$_{36}$H$_{44}$N$_6$O$_{13}$.1.22H$_2$O: C, 54.68; H, 5.92; N, 10.63. Found: C, 54.86; H, 5.91; N, 10.33.

Example 4R

N$^1$-trans-(3-Benzylmethylcarbamoylpropenoyl)-N$^2$—(N-benzyloxycarbonylaspartylglutamylvalyl)-N$^1$-carboxymethylhydrazine (Cbz-Asp-Glu-Val-AAsp-CH=CH—CON(CH$_3$)CH$_2$Ph). $^1$H NMR (DMSO-d$_6$): 0.85 (d, 6H, Val), 1.73 (m, 1H, Glu), 1.87 (m, 1H, Glu), 1.97 (m, 1H, Val), 2.20 (m, 2H, Glu), 2.48 (dd, 1H, Asp), 2.63 (dd, 1H, Asp), 2.88-2.98 (d, 3H, N(CH$_3$)CH$_2$Ph), 4.17 (t, 1H, α-H), 4.32 (m, 2H, α-H), 4.47-4.58 (q, 1H, N(CH$_3$)CH$_2$Ph), 4.66 (s, 1H, N(CH$_3$)CH$_2$Ph), 5.00 (s, 2H, Cbz), 7.14 (d, 1H, db), 7.20 (d, 1H, db), 7.28-7.36 (m, 10H, Ph), 7.57 (d, 1H, NH), 7.91-7.95 (m, 2H, NH), 10.99 (s, 1H, NH—N). HRMS (ESI) Calcd. for C$_{36}$H$_{44}$N$_6$O$_{13}$: 768.3045; Observed m/z: 768.3039. Anal.

Calcd. for $C_{36}H_{44}N_6O_{13}$·EtOAc: C, 55.44; H, 6.20 N, 9.95. Found: C, 55.32; H, 6.20; N, 9.95.

Example 4S $N^2$—(N-Benzyloxycarbonylaspartylglutamylvalyl)-$N^1$-carboxymethyl-$N^1$-trans-(3-phenethylmethylcarbamoylpropenoyl)hydrazine (Cbz-Asp-Glu-Val-AAsp-CH=CH—CON(CH$_3$)CH$_2$CH$_2$Ph). $^1$H NMR (DMSO-d$_6$): 0.86 (t, 6H, Val), 1.75 (m, 1H, Glu), 1.89 (m, 1H, Glu), 2.01 (m, 1H, Val), 2.21 (m, 2H, Glu), 2.46 (dd, 1H, Asp), 2.62 (dd, 1H, Asp), 2.80(t, 2H, N(CH$_3$)CH$_2$CH$_2$Ph), 2.85-2.98 (d, 3H, N(CH$_3$)CH$_2$CH$_2$Ph), 3.73 (d, 2H, N(CH$_3$)CH$_2$CH$_2$Ph), 4.18 (t, 1H, α-H), 4.32 (m, 2H, α-H), 5.00 (s, 2H, Cbz), 6.94 (d, 1H, db), 7.05 (dd, 1H, db), 7.15-7.32 (m, 10H, Ph), 7.59 (d, 1H, NH), 7.91 (d, 1H, NH), 7.97 (d, 1H, NH), 10.93 (d, 1H, NH—N). HRMS (ESI) Calcd. for $C_{37}H_{46}N_6O_{13}$: 783.3196; Observed m/z: 783.3182. Anal. Calcd. for $C_{37}H_{46}N_6O_{13}$·1.09H$_2$O·0.24TFA: C, 54.32; H, 5.77; N, 10.14. Found: C, 54.32; H, 5.91; N, 9.92.

Example 4T $N^2$—(N-Benzyloxycarbonylaspartylglutamylvalyl)-$N^1$-carboxymethyl-$N^1$-trans-(3-dibenzylcarbamoylpropenoyl)hydrazine (Cbz-Asp-Glu-Val-AAsp-CH=CH—CON(CH$_2$Ph)$_2$). $^1$H NMR (DMSO-d$_6$): 0.87 (t, 6H, Val), 1.73 (m, 1H, Glu), 1.87 (m, 1H, Glu), 2.02 (m, 1H, Val), 2.23 (m, 2H, Glu), 2.48 (dd, 1H, Asp), 2.65 (dd, 1H, Asp), 4.19 (t, 1H, α-H), 4.33 (m, 2H, α-H), 4.55 (d, 2H, N(CH$_2$Ph)$_2$), 4.63 (s, 2H, N(CH$_2$Ph)$_2$), 5.00 (s, 2H, Cbz), 7.14 (d, 1H, db), 7.21-7.34 (m, 16H, db, Cbz-Ph, and N(CH$_2$Ph)$_2$), 7.60 (d, 1H, NH), 7.91-7.98 (dd, 2H, NH), 11.00 (s, 1H, NH—N). HRMS (ESI) Calcd. for $C_{42}H_{48}N_6O_{13}$: 844.3352; Observed m/z: 844.3210. Anal. Calcd. for $C_{42}H_{48}N_6O_{13}$·0.53H$_2$O·0.40TFA: C, 57.12; H, 5.54 N, 9.34. Found: C, 57.12; H, 5.64; N, 9.11.

Example 4U $N^2$—(N-Benzyloxycarbonylaspartylglutamylvalyl)-$N^1$-carboxymethyl-$N^1$-trans-(3-(4-fluorobenzyl)carbamoylpropenoyl)hydrazine (Cbz-Asp-Glu-Val-AAsp-CH=CH—CONHCH$_2$-4-F-Ph). $^1$H NMR (DMSO-d$_6$): 0.86 (t, 6H, Val), 1.75 (m, 1H, Glu), 1.88 (m, 1H, Glu), 2.01 (m, 1H, Val), 2.20 (m, 2H, Glu), 2.48 (dd, 1H, Asp), 2.65 (dd, 1H, Asp), 4.18 (t, 1H, α-H), 4.34 (m, 4H, α-H and NHCH$_2$Ph-4-F), 5.01 (s, 2H, Cbz), 6.93 (d, 1H, db), 7.12 (d, 2H, NHCH$_2$Ph-4-F), 7.25-7.32 (m, 8H, Cbz-Ph, NHCH$_2$Ph-4-F, and db), 7.59 (d, 1H, NH), 7.90-7.99 (dd, 2H, NH), 8.94 (t, 1H, NHCH$_2$Ph-4-F), 10.98 (s, 1H, NH—N). HRMS (ESI) Calcd. for $C_{35}H_{41}N_6O_{13}F$: 772.2788; Observed m/z: 772.2747. Anal. Calcd. for $C_{35}H_{41}N_6O_{13}F$·2.08H$_2$O: C, 51.92; H, 5.62; N, 10.38. Found: C, 51.92; H, 5.40; N, 10.21.

Example 4V $N^2$—(N-Benzyloxycarbonylaspartylglutamylvalyl)-$N^1$-carboxymethyl-$N^1$-trans-(3-(3,4-dihydro-2H-quinolin-1-ylcarbonyl)propenoyl)hydrazine (Cbz-Asp-Glu-Val-AAsp-CH=CH—CO-tetrahydroquinoline). $^1$H NMR (DMSO-d$_6$): 0.89 (t, 6H, Val), 1.75 (m, 1H, Glu), 1.87 (m, 3H, Glu and NCH$_2$CH$_2$CH$_2$), 2.02 (m, 1H, Val), 2.20 (m, 2H, Glu), 2.48 (dd, 1H, Asp), 2.65 (dd, 1H, Asp), 2.70 (t, 2H, NCH$_2$CH$_2$CH$_2$), 3.73 (t, 2H, NCH$_2$CH$_2$CH$_2$), 4.19 (t, 1H, α-H), 4.33 (m, 2H, α-H), 5.01 (s, 2H, Cbz), 6.95 (m, 1H, db), 7.04 (d, 1H, db), 7.14-7.33 (m, 9H, Cbz-Ph, and quinoline), 7.60 (d, 1H, NH), 7.96 (dd, 2H, NH), 11.02 (s, 1H, NH—N). HRMS (ESI) Calcd. for $C_{37}H_{44}N_6O_{13}$: 780.3039; Observed m/z: 780.2954. Anal. Calcd. for $C_{37}H_{44}N_6O_{13}$·0.48H$_2$O·0.47TFA: C, 54.06; H, 5.43 N, 9.97. Found: C, 54.16; H, 5.72; N, 9.67.

Example 4W $N^2$—(N-Benzyloxycarbonylaspartylglutamylvalyl)-$N^1$-trans-(3-benzoylpropenoyl)-$N^1$-carboxymethylhydrazine (Cbz-Asp-Glu-Val-AAsp-CH=CH—COPh). $^1$H NMR (DMSO-d$_6$): 0.82 (d, 6H, Val), 1.73 (m, 1H, Glu), 1.85 (m, 1H, Glu), 1.98 (m, 1H, Val), 2.20 (m, 2H, Glu), 2.48 (dd, 1H, Asp), 2.62 (dd, 1H, Asp), 4.16 (t, 1H, α-H), 4.33 (m, 2H, α-H), 5.01 (s, 2H, Cbz), 7.24 (d, 1H, db), 7.32 (s, 5H, Ph), 7.54 (t, 3H, Ph), 7.67 (t, 1H, NH), 7.79 (d, 1H, NH), 7.93 (t, 1H, NH), 7.97 (d, 2H, Ph), 11.06 (s, 1H, NH—N). HRMS (ESI) Calcd. for $C_{34}H_{39}N_5O_{13}$: 725.2623; Observed m/z: 725.2543. Anal. Calcd. for $C_{34}H_{39}N_5O_{13}$·H$_2$O·0.61TFA: C, 52.02; H, 5.16; N, 8.61. Found: C, 52.01; H, 5.10; N, 8.54.

Example 4X $N^2$—(N-Benzyloxycarbonylisoleucylglutamylthreonyl)-$N^1$-carboxymethyl-$N^1$-trans-(3-ethoxycarbonylpropenoyl)hydrazine (Cbz-Ile-Glu-Thr-AAsp-CH=CH—COOEt). $^1$H NMR (DMSO-d$_6$): 0.8 (m, 6H, Ile CH$_3$), 1-1.2 (m, 4H, Thr CH$_3$ and Ile CH$_2$), 1.2-1.3 (t, 3H, OCH$_2$CH$_3$), 1.4 (m, 1H, Ile CH$_2$), 1.6-1.8 (m, 2H, CH Ile and Glu CH$_2$), 1.8-2.0 (m, 1H, Glu CH$_2$), 2.15-2.35 (m, 2H, Glu CH$_2$), 3.85-4.05 (m, 3H, NCH$_2$COOH and CH—OH), 4.1-4.3 (m, 3H, OCH$_2$CH$_3$ and α-H), 4.4 (m, 2H, α-H), 5.05 (m, 2H, Cbz), 6.6-6.65 (d, 1H, CH=CH), 7.20-7.40 (m, 6H, Ph and CH=CH), 7.80 (m, 1H, NH), 8.1 (m, 1H, NH). HRMS (FAB) Calcd. for $C_{31}H_{44}N_5O_{13}$: 694.29356; Observed m/z 694.29979. Anal. Calcd. for $C_{31}H_{43}N_5O_{13}$·H$_2$O: C, 52.32; H, 6.33; N, 9.84. Found: C, 52.38; H, 6.35; N, 9.83.

Example 4Y $N^1$-trans-(3-Benzyloxycarbonylpropenoyl)-$N^2$—(N-benzyloxycarbonylisoleucylglutamylthreonyl)-$N^1$-carboxylmethylhydrazine (Cbz-Ile-Glu-Thr-AAsp-CH=CH—COOCH$_2$Ph). $^1$H NMR (DMSO-d$_6$): 0.80 (m, 6H, Ile CH$_3$), 1.02 (m, 3H, Thr CH$_3$), 1.10 (m, 2H, Ile CH$_2$), 1.65 (m, 1H, Ile CH), 1.75 and 1.85 (d of m, 2H, Glu CH$_2$), 2.25 (m, 2H, Glu CH$_2$), 3.30 (s, 2H, AAsp CH$_2$), 3.90 (m, 2H, α-H), 4.25 (m, 1H, α-H), 4.39 (m, 1H, Thr CH), 5.00 (s, 2H, Z), 5.20 (s, 2H, CH$_2$Ph), 6.70 (d, 1H, NH), 7.20-7.40 (m, 12H, Ph and CH=CH), 7.90 (b, 1H, NH), 8.10 (b, 1H, NH), 8.60 (m, 1H, NH), 10.70 (b, 2H, COOH). HRMS (FAB) Calcd. for $C_{36}H_{46}N_5O_{13}$: 756.3092; Observed m/z 756.3037. Anal. Calcd; for $C_{36}H_{45}N_5O_{13}$·2H$_2$O: C, 54.61; H, 6.24; N, 8.84. Found: C, 54.82; H, 6.64; N, 9.08.

Example 4Z $N^2$—(N-Benzyloxycarbonylisoleucylglutamylthreonyl)-$N^1$-carboxylmethyl-$N^1$-trans-(3-phenylcarbamoylpropenoyl)hydrazine (Cbz-Ile-Glu-Thr-AAsp-CH=CH—CONHPh). $^1$H NMR (DMSO-d$_6$): 0.84 (t, 6H, Ile CH$_3$), 1.06 (m, 3H, Thr CH$_3$), 1.45 (m, 2H, Ile CH$_2$), 1.70 (m, 1H, Ile CH), 1.80 and 1.90 (d of m, 2H, Glu CH$_2$), 2.25 (m, 2H, Glu CH$_2$), 3.33 (s, 2H, AAsp CH$_2$), 3.88 (t, 1H, α-H), 4.00 (m, 1H, α-H), 4.25 (m, 1H, α-H), 4.39 (m, 1H, Thr CH), 5.00 (s, 2H, Z), 7.00-7.10 (m, 4H, CH=CH and Ph), 7.30 (m, 7H, Ph and NH), 7.64 (d, 2H, Ph), 7.85 (b, 1H, NH), 8.05 (d, 1H, NH), 8.35 (m, 1H, NH), 8.60 (m, 1H, NH), 10.45 (b, 2H, COOH).

HRMS (FAB) Calcd. for $C_{35}H_{45}N_6O_{12}$: 741.3095; Observed m/z 741.3106. Anal. Calcd. for $C_{35}H_{44}N_6O_{12}\cdot2H_2O$: C, 54.12; H, 6.23; N, 10.82. Found: C, 53.07; H, 5.88; N, 10.98.

Example 4AA $N^1$-trans-(3-Benzylcarbamoylpropenoyl)-$N^2$—(N-benzyloxycarbonylisoleucylglutamylthreonyl)-$N^1$-carboxylmethylhydrazine (Cbz-Ile-Glu-Thr-AAsp-CH=CH—CONHCH$_2$Ph). $^1$H NMR (DMSO-$d_6$): 0.75-0.87 (m, 6H, Ile CH$_3$), 1.02 (m, 3H, Thr CH$_3$), 1.49 (m, 2H, Ile CH$_2$), 1.65 (m, 1H, Ile CH), 1.74 and 1.85 (d of m, 2H, Glu CH$_2$), 2.25 (m, 2H, Glu CH$_2$), 3.32 (s, 2H, AAsp CH$_2$), 4.00 (m, 2H, α-H), 4.25 (m, 1H, α-H), 4.40 (m, 3H, Thr CH and CH$_2$Ph), 5.00 (s, 2H, Z), 7.00 (d, 1H, CH=CH), 7.40-7.40 (m, 13H, CH=CH, Ph and NH), 7.90 (b, 1H, NH), 8.05 (b, 1H, NH), 8.90 (b, 1H, NH), 10.60 (b, 2H, COOH). HRMS (FAB) Calcd. for $C_{36}H_{47}N_6O_{12}$: 755.3252; Observed m/z 755.3200. Anal. Calcd. for $C_{36}H_{46}N_6O_{12}\cdot2H_2O$: C, 54.68; H, 6.37; N, 10.63. Found: C, 55.02; H, 6.32; N, 10.70.

Example 4BB $N^2$—(N-Benzyloxycarbonylisoleucylglutamylthreonyl)-$N^1$-carboxylmethyl-$N^1$-trans-(3-phenyethylcarbamoylpropenoyl)hydrazine (Cbz-Ile-Glu-Thr-AAsp-CH=CH—CONHCH$_2$CH$_2$Ph). $^1$H NMR (DMSO-$d_6$): 0.82 (m, 6H, Ile CH$_3$), 1.04 (m, 3H, Thr CH$_3$), 1.45 (m, 2H, Ile CH$_2$), 1.65 (m, 1H, Ile CH), 1.75 and 1.90 (d of m, 2H, Glu CH$_2$), 2.24 (m, 2H, Glu CH$_2$), 2.73 (t, 2H, CH$_2$Ph), 3.32 (m, 4H, AAsp CH$_2$ and NCH$_2$), 3.95 (m, 2H, α-H), 4.22 (m, 1H, α-H), 4.40 (m, 1H, Thr CH), 5.00 (s, 2H, Z), 6.88 (d, 1H, CH=CH), 7.10-7.45 (m, 13H, CH=CH, Ph and NH), 7.90 (b, 2H, NH), 8.05 (b, 1H, NH), 8.52 (b, 1H, NH), 10.73 (b, 2H, COOH). HRMS (FAB) Calcd. for $C_{37}H_{49}N_6O_{12}$: 769.3408; Observed m/z 769.3332. Anal. Calcd. for $C_{37}H_{48}N_6O_{12}\cdot2H_2O$: C, 55.22; H, 6.51; N, 10.44. Found: C, 55.34; H, 6.46; N, 10.55.

Example 4CC $N^1$-trans-(3-Benzylmethylcarbamoylpropenoyl)-$N^2$—(N-benzyloxycarbonylisoleucylglutamylthreonyl)-$N^1$-carboxylmethylhydrazine (Cbz-Ile-Glu-Thr-AAsp-CH=CH—CON(CH$_3$)CH$_2$Ph). $^1$H NMR (DMSO-$d_6$): 0.80 (m, 6H, Ile CH$_3$), 1.06 (m, 3H, Thr CH$_3$), 1.49 (m, 2H, Ile CH$_2$), 1.65 (m, 1H, Ile CH), 1.80 and 1.92 (d of m, 2H, Glu CH$_2$), 2.24 (m, 2H, Glu CH$_2$), 2.88 and 2.99 (d, 3H, NCH$_3$), 3.32 (s, 2H, AAsp CH$_2$), 4.02 (m, 2H, α-H), 4.20 (m, 1H, α-H), 4.40 (m, 1H, Thr CH), 4.55 (m, 2H, CH$_2$Ph), 5.00 (s, 2H, Z), 7.10-7.45 (m, 14H, CH=CH, Ph and NH), 7.80 (m, 1H, NH), 8.05 (m, 1H, NH),10.90 (b, 2H, COOH). HRMS (FAB) Calcd. for $C_{37}H_{49}N_6O_{12}$: 769.3408; Observed m/z 769.3394. Anal. Calcd. for $C_{37}H_{48}N_6O_{12}\cdot2H_2O$: C, 55.22; H, 6.51; N, 10.44. Found: C, 55.02; H, 6.03; N, 10.26.

Example 4DD $N^2$—(N-Benzyloxycarbonylisoleucylglutamylthreonyl)-$N^1$-carboxylmethyl-$N^1$-trans-(3-methylphenylethylcarbamoylpropenoyl)hydrazine (Cbz-Ile-Glu-Thr-AAsp-CH=CH—CON(CH$_3$)CH$_2$CH$_2$Ph). $^1$H NMR (acetone-$d_6$): 0.88 (m, 3H, Ile CH$_3$), 0.97 (m, 3H, Ile CH$_3$), 0.97 (m, 3H, Ile CH$_3$), 1.21 (m, 3H, Thr CH$_3$), 1.60 (m, 3H, Ile CH and CH$_2$), 2.00 (m, 2H, Glu CH$_2$), 2.47 (m, 2H, Glu CH$_2$), 2.88 (m, 4H, CH$_2$Ph and AAsp CH$_2$), 2.98 and 3.10 (d, 3H, CH$_3$), 3.67 (m, 2H, CH$_2$N), 4.13 (m, 1H, α-H), 4.32 (m, 1H, α-H), 4.50 (m, 2H, α-H and Thr CH), 5.09 (m, 2H, Z), 6.62 (b, 1H, NH), 7.10-7.40 (m, 13H, CH=CH, NH and Ph), 7.65 (b, 1H, NH), 7.90 (b, 1H, NH). HRMS (FAB) Calcd. for $C_{38}H_{51}N_6O_{12}$: 783.3565; Observed m/z 783.3569. Anal. Calcd. for $C_{38}H_{50}N_6O_{12}\cdot2H_2O$: C, 55.74; H, 6.65; N, 10.26. Found: C, 55.59; H, 6.23; N, 10.07.

Example 4EE $N^2$—(N-Benzyloxycarbonylisoleucylglutamylthreonyl)-$N^1$-carboxymethyl-$N^1$-trans-(3-dibenzylcarbamoylpropenoyl)hydrazine (Cbz-Ile-Glu-Thr-AAsp-CH=CH—CON(CH$_2$Ph)$_2$). $^1$H NMR (DMSO-$d_6$): 0.80 (m, 6H, Ile CH$_3$), 1.06 (m, 3H, Thr CH$_3$), 1.50 (m, 2H, Ile CH$_2$), 1.65 (m, 1H, Ile CH), 1.78 and 1.90 (d of m, 2H, Glu CH$_2$), 2.25 (m, 2H, Glu CH$_2$), 3.32 (s, 2H, AAsp CH$_2$), 4.00 (m, 2H, α-H), 4.25 (m, 1H, α-H), 4.40 (m, 1H, Thr CH), 4.60 (d, 4H, CH$_2$Ph), 5.00 (s, 2H, Z), 7.00-7.35 (m, 13H, CH=CH, Ph and NH), 7.85 (b, 1H, NH), 8.10 (d, 1H, NH), 8.60 (b, 1H, NH), 10.75 (b, 2H, COOH). HRMS (FAB) Calcd. for $C_{43}H_{53}N_6O_{12}$: 845.3721; Observed m/z 845.3731. Anal. Calcd. for $C_{43}H_{52}N_6O_{12}\cdot2H_2O$: C, 58.63; H, 6.41; N, 9.54. Found: C, 58.40; H, 6.14; N, 9.68.

Example 4FF $N^2$—(N-Berzyloxycarbonylleucylglutamylthreonyl)-$N^1$-carboxymethyl-$N^1$-trans-(3-ethoxycarbonylpropenoyl)hydrazine (Cbz-Leu-Glu-Thr-AAsp-CH=CH—COOEt). $^1$H NMR (DMSO-$d_6$): 0.85 (t, 6H, Leu CH$_3$), 1.05 (d, 3H, Thr CH$_3$), 1.25 (t, 3H, OCH$_2$CH$_3$), 1.4 (m, 2H, Leu CH$_2$), 1.6 (m, 1H, CH Leu), 1.75 (m, 1H, Glu CH$_2$), 1.9 (m, 1H, Glu CH$_2$), 2.25 (m, 2H, Glu CH$_2$), 3.9-4.1 (m, 3H, NCH$_2$COOH and α-H), 4.1-4.3 (m, 3H, OCH$_2$CH$_3$ and CH—OH), 4.3-4.4 (m, 2H, α-H), 5.02 (m, 2H, Cbz), 6.6-6.65 (d, 1H, CH=CH), 7.20-7.40 (m, 6H, Ph and CH=CH), 7.50 (d, 1H, NH), 7.78 (m, 1H, NH), 8.05 (m, 1H, NH). HRMS (FAB) Calcd. for $C_{31}H_{44}N_5O_{13}$: 694.29356; Observed m/z 694.29963. Anal. Calcd. for $C_{31}H_{43}N_5O_{13}\cdot H_2O$: C, 52.32; H, 6.33; N, 9.84. Found: C, 52.54; H, 6.28; N, 9.69.

Example 4GG $N^1$-trans-(3-Benzyloxycarbonylpropenoyl)-$N^2$—(N-benzyloxycarbonylleucylglutamylthreonyl)-$N^1$-carboxymethylhydrazine (Cbz-Leu-Glu-Thr-AAsp-CH=CH—COOCH$_2$Ph). $^1$H NMR (DMSO-$d_6$): 0.84 (t, 6H, Leu), 1.02 (d, 3H, Thr), 1.40 (m, 2H, Leu), 1.60 (m, 1H, Glu), 1.73 (m, 1H, Glu), 1.90 (m, 1H, Leu), 2.22 (m, 2H, Glu), 3.94 (m, 1H, α-H), 4.03 (m, 1H, α-H), 4.20 (m, 1H, α-H), 4.37 (m, 1H, Thr), 4.99 (s, 2H, Cbz), 5.19 (s, 2H, Bzl), 6.65 (d, 1H, db), 7.32-7.36 (m, 10H, Ph), 7.42 (d, 1H, db), 7.76 (d, 1H, NH), 8.03 (d, 1H, NH), 10.84 (s, 1H, NH—N). HRMS (ESI) Calcd. for $C_{36}H_{45}N_5O_{13}$: 755.3092; Observed m/z: 755.3150. Anal. Calcd. for $C_{36}H_{45}N_5O_{13}\cdot0.27H_2O\cdot0.28TFA$: C, 55.41; H, 5.83; N, 8.84. Found: C, 55.41; H, 5.77; N, 8.77.

Example 4HH $N^2$—(N-Benzyloxycarbonylleucylglutamylthreonyl)-$N^1$-carboxylmethyl-$N^1$-trans-(3-phenylcarbamoylpropenoyl)hydrazine (Cbz-Leu-Glu-Thr-AAsp-CH=CH—CONHPh). $^1$H NMR (DMSO-$d_6$): 0.85 (t, 6H, Leu CH$_3$), 1.06 (m, 3H, Thr CH$_3$), 1.49 (m, 2H, Leu CH$_2$), 1.61 (m, 1H, Leu CH), 1.80 and 1.95 (d of m, 2H, Glu CH$_2$), 2.26 (m, 2H, Glu CH$_2$), 3.32 (s, 2H, AAsp CH$_2$), 4.03 (m, 2H, α-H), 4.25 (m, 1H, α-H), 4.40 (m, 1H, Thr CH), 5.00 (s, 2H, Z), 7.00-7.10 (m, 4H, CH=CH and Ph), 7.30 (m, 7H, Ph and NH), 7.64 (d, 2H, Ph), 7.85 (m, 1H, NH), 8.05 (b, 1H, NH), 8.20 (m, 1H, NH), 8.75 (b, 1H, NH), 10.45 (s, 2H, COOH). HRMS (FAB) Calcd. for $C_{35}H_{45}N_6O_{12}$: 741.3095; Observed m/z 741.3064. Anal. Calcd. for $C_{35}H_{44}N_6O_{12}\cdot 2H_2O$: C, 54.12; H, 6.23; N, 10.82. Found: C, 53.86; H, 5.81; N, 10.85.

Example 4II $N^1$-trans-(3-Benzylcarbamoylpropenoyl)-$N^2$—(N-benzyloxycarbonylleucylglutamylthreonyl)-$N^1$-carboxylmethylhydrazine (Cbz-Leu-Glu-Thr-AAsp-CH=CH—CONHCH$_2$Ph). $^1$H NMR (DMSO-d$_6$): 0.85 (t, 6H, Leu CH$_3$), 1.06 (m, 3H, Thr CH$_3$), 1.49 (m, 2H, Leu CH$_2$), 1.61 (m, 1H, Leu CH), 1.80 and 1.90 (d of m, 2H, Glu CH$_2$), 2.26 (m, 2H, Glu CH$_2$), 3.32 (s, 2H, AAsp CH$_2$), 4.03 (m, 2H, α-H), 4.25 (m, 1H, α-H), 4.45 (m, 3H, Thr CH and CH$_2$Ph), 5.00 (s, 2H, Z), 7.00 (d, 1H, CH=CH), 7.20-7.40 (m, 13H, CH=CH, Ph and NH), 7.80 (b, 1H, NH), 8.05 (d, 1H, NH), 8.90 (d, 1H, NH), 10.65 (b, 2H, COOH). HRMS (FAB) Calcd. for $C_{36}H_{47}N_6O_{12}$: 755.3252; Observed m/z 755.3184. Anal. Calcd. for $C_{36}H_{46}N_6O_{12}\cdot 2H_2O$: C, 54.68; H, 6.37; N, 10.63. Found: C, 54.96; H, 6.72; N, 10.85.

Example 4JJ $N^2$—(N-Benzyloxycarbonylleucylglutamylthreonyl)-$N^1$-carboxylmethyl-$N^1$-trans-(3-phenylethylcarbamoylpropenoyl)hydrazine (Cbz-Leu-Glu-Thr-AAsp-CH=CH—CONHCH$_2$CH$_2$Ph). $^1$H NMR (DMSO-d$_6$): 0.85 (t, 6H, Leu CH$_3$), 1.06 (m, 3H, Thr CH$_3$), 1.45 (m, 2H, Leu CH$_2$), 1.60 (m, 1H, Leu CH), 1.75 and 1.88 (d of m, 2H, Glu CH$_2$), 2.25 (m, 2H, Glu CH$_2$), 2.75 (t, 2H, CH$_2$Ph), 3.30-3.35 (m, 4H, CH$_2$N and AAsp CH$_2$), 4.00 (m, 2H, α-H), 4.20 (m, 1H, α-H), 4.38 (m, 1H, Thr CH), 5.00 (s, 2H, Z), 6.90-7.15 (d of d, 2H, CH=CH), 7.20-7.40 (m, 12H, Ph and NH), 7.86 (m, 1H, NH), 8.06 (d, 1H, NH), 8.50 (b, 1H, NH), 10.60 (b, 2H, COOH). HRMS (FAB) Calcd. for $C_{37}H_{49}N_6O_{12}$: 769.3408; Observed m/z 769.3201. Anal. Calcd. for $C_{37}H_{48}N_6O_{12}\cdot 2H_2O$: C, 55.22; H, 6.51; N, 10.44. Found: C, 55.78; H, 6.15; N, 10.61.

Example 4KK $N^1$-trans-(3-Benzylmethylcarbamoylpropenoyl)-$N^2$—(N-benzyloxycarbonylleucylglutamylthreonyl)-$N^1$-carboxylmethylhydrazine (Cbz-Leu-Glu-Thr-AAsp-CH=CH—CON(CH$_3$)CH$_2$Ph). $^1$H NMR (DMSO-d$_6$): 0.83 (t, 6H, Leu CH$_3$), 1.06 (m, 3H, Thr CH$_3$), 1.49 (m, 2H, Leu CH$_2$), 1.65 (m, 1H, Leu CH), 1.80 and 1.92 (d of m, 2H, Glu CH$_2$), 2.24 (m, 2H, Glu CH$_2$), 2.88 and 2.99 (d, 2H, CH$_3$), 3.32 (s, 2H, AAsp CH$_2$), 4.02 (m, 2H, α-H), 4.20 (m, 1H, α-H), 4.40 (m, 1H, Thr CH), 4.55 (m, 2H, CH$_2$Ph), 5.00 (s, 2H, Z), 7.10-7.45 (m, 14H, CH=CH, Ph and NH), 7.80 (m, 1H, NH), 8.05 (m, 1H, NH),10.85 (b, 2H, COOH). HRMS (FAB) Calcd. for $C_{37}H_{49}N_6O_{12}$: 769.3408; Observed m/z 769.3320. Anal. Calcd. for $C_{37}H_{48}N_6O_{12}\cdot 2H_2O$: C, 55.22; H, 6.51; N, 10.44. Found: C, 55.02; H, 6.03; N, 10.26.

Example 4LL $N^2$—(N-Benzyloxycarbonylleucylglutamylthreonyl)-$N^1$-carboxylmethyl-$N^1$-trans-(3-methylphenylethylcarbamoylpropenoyl)hydrazine (Cbz-Leu-Glu-Thr-AAsp-CH=CH—CON(CH$_3$)CH$_2$CH$_2$Ph). $^1$H NMR (acetone-d$_6$): 0.94 (m, 6H, Leu CH$_3$), 1.20 (m, 3H, Thr CH$_3$), 1.65 (m, 2H, Leu CH$_2$), 1.75 (m, 1H, Leu CH), 2.00 (m, 2H, Glu CH$_2$), 2.46 (m, 2H, Glu CH$_2$), 2.88 (m, 4H, CH$_2$Ph and AAsp CH$_2$), 2.98 and 3.11 (d, 3H, NCH$_3$), 3.68 (m, 2H, NCH$_2$), 4.30 (m, 2H, α-H), 4.50 (m, 2H, α-H and Thr CH), 5.09 (m, 2H, Z), 5.65 (b, 1H, NH), 6.75 (b, 1H, NH), 7.10-7.40 (m, 12H, CH=CH and Ph), 7.85 (b, 1H, NH), 7.95 (b, 1H, NH). HRMS (FAB) Calcd. for $C_{38}H_{51}N_6O_{12}$: 783.3565; Observed m/z 783.3493. Anal. Calcd. for $C_{38}H_{50}N_6O_{12}\cdot 2H_2O$: C, 55.74; H, 6.65; N, 10.26. Found: C, 55.60; H, 6.84; N, 9.99.

Example 4MM $N^2$—(N-Benzyloxycarbonylleucylglutamylthreonyl)-$N^1$-carboxylmethyl-$N^1$-trans-(3-dibenzylcarbamoylpropenoyl)hydrazine (Cbz-Leu-Glu-Thr-AAsp-CH=CH—CON(CH$_2$Ph)$_2$). $^1$H NMR (DMSO-d$_6$): 0.85 (t, 6H, Leu CH$_3$), 1.06 (m, 3H, Thr CH$_3$), 1.45 (m, 2H, Leu CH$_2$), 1.60 (m, 1H, Leu CH), 1.80 and 1.90 (d of m, 2H, Glu CH$_2$), 2.25 (m, 2H, Glu CH$_2$), 3.32 (s, 2H, AAsp CH$_2$), 4.03 (m, 2H, α-H), 4.25 (m, 1H, α-H), 4.40 (m, 1H, Thr CH), 4.60 (d, 4H, CH$_2$Ph), 5.00 (s, 2H, Z), 7.10-7.35 (m, 12H, CH=CH and Ph), 7.40 (b, 1H, NH), 7.80 (b, 1H, NH), 8.07 (b, 1H, NH), 8.65 (m, 1H, NH), 10.75 (b, 2H, COOH). HRMS (FAB) Calcd. for $C_{43}H_{53}N_6O_{12}$: 845.3721; Observed m/z 845.3777. Anal. Calcd. for $C_{43}H_{52}N_6O_{12}\cdot 2H_2O$: C, 58.63; H, 6.41; N, 9.54. Found: C, 58.50; H, 6.00; N, 9.45.

Example 4NN $N^2$—(N-Benzyloxycarbonylleucylglutamylthreonyl)-$N^1$-carboxylmethyl-$N^1$-trans-(3-(4-fluorobenzyl)carbamoylpropenoyl)hydrazine (Cbz-Leu-Glu-Thr-AAsp-CH=CH—CONHCH$_2$-4-F-Ph). $^1$H NMR (DMSO-d$_6$): 0.85 (t, 6H, Leu CH$_3$), 1.04 (m, 3H, Thr CH$_3$), 1.60 (m, 2H, Leu CH$_2$), 1.75 (m, 1H, Leu CH), 1.90 (m, 2H, Glu CH$_2$), 2.24 (m, 2H, Glu CH$_2$), 3.32 (s, 2H, AAsp CH$_2$), 4.03 (m, 2H, α-H), 4.25 (m, 1H, α-H), 4.40 (m, 3H, Thr CH and CH$_2$Ph), 5.00 (s, 2H, Z), 6.93 (d, 1H, CH=CH), 7.10-7.40 (m, 10H, CH=CH and Ph), 7.85 (b, 1H, NH), 8.05 (d, 1H, NH), 8.70 (b, 1H, NH), 8.94 (m, 2H, NH), 10.60 (b, 2H, COOH). HRMS (FAB) Calcd. for $C_{36}H_{46}N_6O_{12}F$: 773.3153; Observed m/z 773.3061. Anal. Calcd. for $C_{36}H_{45}N_6O_{12}F\cdot 2H_2O$: C, 53.46; H, 6.11; N, 10.39. Found: C, 53.62; H, 6.05; N, 10.16.

Example 4OO $N^2$—(N-Benzyloxycarbonylleucylglutamylthreonyl)-$N^1$-carboxylmethyl-$N^1$-trans-(3-(3,4-dihydro-2H-quinolin-1-yloxo)propenoyl)hydrazinee (Cbz-Leu-Glu-Thr-AAsp-CH=CH—CO-tetrahydroquinoline). $^1$H NMR (acetone-d$_6$): 0.94 (m, 6H, Leu CH$_3$), 1.22 (m, 3H, Thr CH$_3$), 1.66 (m, 2H, Leu CH$_2$), 1.78 (m, 1H, Leu CH), 1.98 (m, 2H, quinoline CH$_2$), 2.00 (m, 2H, Glu CH$_2$), 2.46 (m, 2H, Glu CH$_2$), 2.80 (m, 4H, quinoline CH$_2$ and Asp CH$_2$), 3.81 (m, 2H, NCH$_2$), 4.28 (m, 1H, α-H), 4.38 (m, 1H, α-H), 4.50 (m, 2H, α-H and Thr CH), 5.09 (m, 2H, Z), 6.75 (b, 1H, NH), 7.10-7.40 (m, 10H, CH=CH and Ph), 7.48 (d, 1H, Ph), 7.60 (d, 1H, NH), 7.90 (d, 1H, NH), 9.00 (s, 1H, NH). HRMS (FAB) Calcd. for $C_{38}H_{49}N_6O_{12}$: 781.3408; Observed m/z 781.3367. Anal. Calcd. for $C_{38}H_{48}N_6O_{12}\cdot 2H_2O$: C, 55.87; H, 6.42; N, 10.29. Found: C, 55.98; H, 6.02; N, 10.32.

Example 4PP $N^2$—(N-Benzyloxycarbonylleucylglutamylthreonyl)-$N^1$-carboxylmethyl-$N^1$-trans-(3-(methyl-1-naphthylmethyl)carbamoylpropenoyl)hydrazine (Cbz-Leu-Glu-Thr-AAsp-CH=CH—CON(CH$_3$)CH$_2$-1-Napth). $^1$H NMR (acetone-d$_6$): 0.92 (m, 6H, Leu CH$_3$), 1.22 (m, 3H, Thr CH$_3$), 1.65 (m, 2H, Leu CH$_2$), 1.75 (m, 1H, Leu CH), 2.00 (m, 2H, Glu CH$_2$), 2.47 (m, 2H, Glu CH$_2$), 3.08 (d, 4H, AAsp CH$_2$ and NCH$_3$), 4.25 (m, 1H, α-H), 4.35 (m, 2H, α-H), 4.50 (m, 1H, Thr CH), 5.07 (m, 2H, Z), 5.15 (m, 2H, CH$_2$-napth), 6.75 (b, 1H, NH), 7.20-7.35 (m, 6H, CH=CH and Ph), 7.40-7.60 (m, 7H, Ph and NH), 7.90 (m, 2H, napth), 7.80 (b, 1H, NH), 8.10 (b, 1H, NH). HRMS (FAB) Calcd. for C$_{41}$H$_{51}$N$_6$O$_{12}$, 819.3565; Observed m/z 819.3521. Anal. Calcd. for C$_{41}$H$_{50}$N$_6$O$_{12}$.2H$_2$O: C, 57.60; H, 6.37; N, 9.83. Found: C, 57.63; H, 6.07; N, 9.78.

Example 4QQ

N$^2$—(N-Benzyloxycarbonylvalylglutamylvalyl)-N$^1$-carboxymethyl-N$^1$-trans-(3-ethoxycarbonylpropenoyl)hydrazine (Cbz-Val-Glu-Val-AAsp-CH=CH—COOEt). $^1$H NMR (DMSO-d$_6$): 0.80-0.87 (dd, 12H, Val), 1.21 (t, 3H, OCH$_2$CH$_3$), 1.74 (m, 1H, Glu), 1.89 (m, 1H, Glu), 1.94 (m, 1H, Val), 2.20 (m, 2H, Glu), 3.87 (t, 1H, α-H), 4.16 (m, 3H, α-H and OCH$_2$CH$_3$), 4.33 (t, 1H, α-H), 5.01 (s, 2H, Cbz), 6.63 (d, 1H, db), 7.20 (d, 1H, db), 7.33 (m, 5H, Ph), 7.97 (t, 2H, NH), 11.02 (s, 1H, NH—N). HRMS (ESI) Calcd. for C$_{31}$H$_{43}$N$_5$O$_{12}$: 677.2986; Observed m/z: 677.2978. Anal. Calcd. for C$_{31}$H$_{43}$N$_5$O$_{12}$.1.41H$_2$O.0.51hex: C, 54.84; H, 7.02: N, 9.39. Found: C, 54.84; H, 6.73; N, 9.16.

The above specification and Examples fully disclose how to make and use the compounds of the present disclosure. However, the present disclosure is not limited to the particular embodiments described hereinabove, but includes all modifications thereof within the scope of the following claims. The various references to journals, patents, and other publications which are cited herein comprise the state of the art and are incorporated herein by reference.

What is claimed is:

1. A compound of the formula:

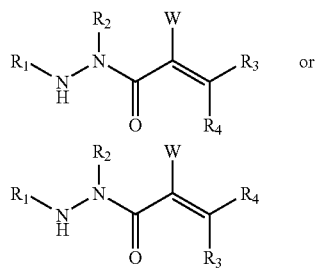

wherein, $R_1$ is selected from the group consisting of $M_1$-$AA_1$, $M_1$-$AA_2$-$AA_1$, and $M_1$-$AA_3$-$AA_2$-$AA_1$;

W is selected from the group consisting of halogen, cyano, and hydrogen;

$M_1$ is selected from the group consisting of H, $NH_2$—CO—, $NH_2$—CS—, $NH_2$—$SO_2$—, X—NH—CO—, $X_2N$—CO—, X—NH—CS—, $X_2N$—CS—, X—NH—$SO_2$—, $X_2N$—$SO_2$—, X—CO—, X—CS—, X—, Y—$SO_2$—, Y—O—CO—, Y—O—CS—, morpholine-CO—, and biotinyl;

X is selected from the group consisting of H, $C_{1-10}$ alkyl, $C_{3-15}$ cyclized alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, pentafluorophenyl, phenyl monosubstituted with K, phenyl disubstituted with K, phenyl trisubstituted with K, naphthyl, naphthyl monosubstituted with K, naphthyl disubstituted with K, naphthyl trisubstituted with K, $C_{1-10}$ fluoroalkyl with an attached phenyl group, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached naphthyl group, $C_{1-10}$ alkyl with an attached naphthyl group substituted with K, $C_{1-10}$ alkyl with an attached phenoxy group, and $C_{1-10}$ alkyl with an attached phenoxy group substituted with K on the phenoxy group;

Y is selected from the group consisting of $C_{1-10}$ alkyl, $C_{3-15}$ cyclized alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl monosubstituted with K, phenyl disubstituted with K, phenyl trisubstituted with K, naphthyl, naphthyl monosubstituted with K, naphthyl disubstituted with K, naphthyl trisubstituted with K, $C_{1-10}$ fluoroalkyl with an attached phenyl group, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached naphthyl group, $C_{1-10}$ alkyl with an attached naphthyl group substituted with K, $C_{1-10}$ alkyl with an attached phenoxy group, and $C_{1-10}$ alkyl with an attached phenoxy group substituted with K on the phenoxy group;

J is selected from the group consisting of halogen, $CO_2H$, OH, CN, $NO_2$, amino, $C_{1-10}$ alkoxy, $C_{1-10}$ alkylamino, $C_{2-12}$ dialkylamino, $C_{1-10}$ alkyl-O—CO—, $C_{1-10}$ alkyl-O—CO—NH—, and $C_{1-10}$ alkyl-S—;

K is selected from the group consisting of halogen, $C_{1-10}$ alkyl, $C_{1-10}$ perfluoroalkyl, $C_{1-10}$ alkoxy, phenoxy, $NO_2$, CN, OH, $CO_2H$, $CONH_2$, amino, $C_{1-10}$ alkylamino, $C_{2-12}$ dialkylamino, $C_{1-10}$ acyl, and $C_{1-10}$ alkoxy-CO—, and $C_{1-10}$ alkyl-S—;

$AA_1$, $AA_2$, and $AA_3$ are side chain blocked or unblocked amino acids with the L configuration, D configuration, or no chirality at the alpha-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutanoic acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—CH($CH_2CHEt_2$)—$CO_2H$, alpha-aminoheptanoic acid, $NH_2$—CH($CH_2$-1-naphthyl)-$CO_2H$, $NH_2$—CH($CH_2$-2-naphthyl)-$CO_2H$, $NH_2$—CH($CH_2CH_2CH_2$-phenyl)-$CO_2H$, $NH_2$—CH($CH_2$-cyclohexyl)-$CO_2H$, $NH_2$—CH($CH_2$-cyclopentyl)-$CO_2H$, $NH_2$—CH($CH_2$-cyclobutyl)—$CO_2H$, $NH_2$—CH($CH_2$-cyclopropyl)-$CO_2H$, trifluoroleucine, 4-fluorophenylalanine, lysine substituted on the epsilon nitrogen with a biotinyl group, hexafluoroleucine,

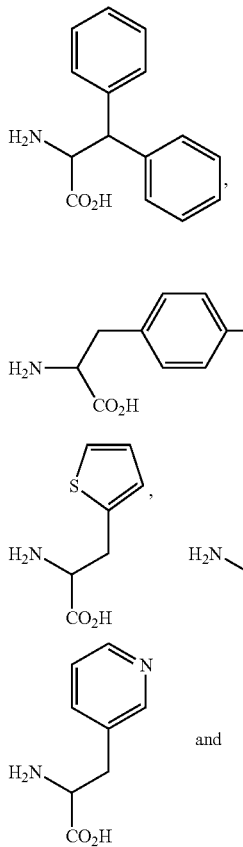

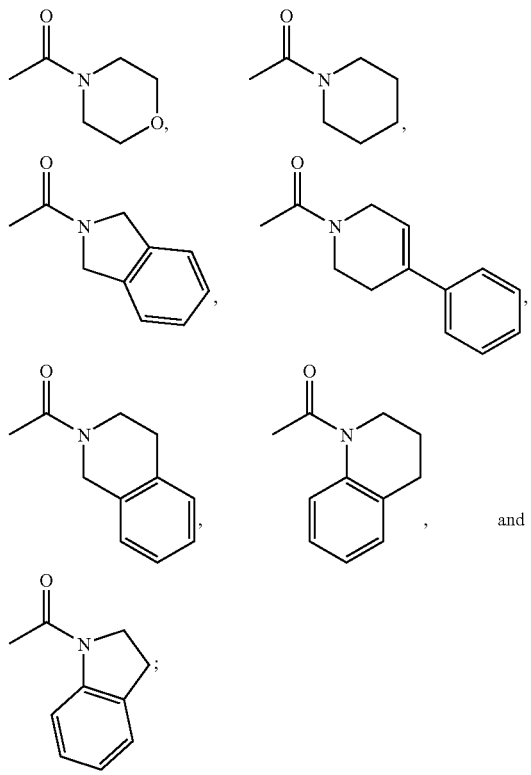

R$_2$ is selected from the group consisting of C$_{1-10}$ alkyl, C$_{1-10}$ perfluoroalkyl, C$_{1-10}$ alkyl substituted with Q, C$_{1-10}$ alkyl substituted with phenyl, C$_{1-10}$ alkyl with an attached phenyl substituted with K, C$_{1-10}$ alkyl substituted with naphthyl, C$_{1-10}$ alkyl with an attached naphthyl substituted with K, phenyl, phenyl substituted with K, naphthyl, naphthyl substituted with K, C$_{1-10}$ alkyl substituted with CONH$_2$, C$_{1-10}$ alkyl substituted with CONHR$_5$, C$_{1-10}$ alkyl substituted with CO$_2$H, C$_{1-10}$ alkyl substituted with SO$_2$NH$_2$, C$_{1-10}$ alkyl substituted with SO$_3$H, 2-furyl, 3-furyl, 2-thienyl, 3-thienyl, 2-furyl substituted with K, 3-furyl substituted with K, 2-thienyl substituted with K, 3-thienyl substituted with K, 2-furyl substituted with G, 3-furyl substituted with G, 2-thienyl substituted with G, 3-thienyl substituted with G, C$_{1-10}$ alkyl substituted with CO$_2$R$_5$, CH$_2$CH$_2$SCH$_3$, CH$_2$-3-indolyl, C$_{1-2}$ alkyl with an attached 2-furyl, C$_{1-2}$ alkyl with an attached 3-furyl, C$_{1-2}$ alkyl with an attached 2-thienyl, C$_{1-2}$ alkyl with an attached 3-thienyl, C$_{1-2}$ alkyl with an attached 2-furyl substituted with K, C$_{1-2}$ alkyl with an attached 3-furyl substituted with K, C$_{1-2}$ alkyl with an attached 2-thienyl substituted with K, C$_{1-2}$ alkyl with an attached 3-thienyl substituted with K, C$_{1-2}$ alkyl with an attached 2-furyl substituted with G, C$_{1-2}$ alkyl with an attached 3-furyl substituted with G, C$_{1-2}$ alkyl with an attached 2-thienyl substituted with G, C$_{1-2}$ alkyl with an attached 3-thienyl substituted with G, CH$_2$-2-imidazyl, C$_{1-10}$ alkyl substituted with G, C$_{1-10}$ alkyl with an attached phenyl substituted with G, C$_{1-10}$ alkyl with an attached naphthyl substituted with G, phenyl substituted with G, and naphthyl substituted with G;

R$_5$ is selected from the group consisting of C$_{1-10}$ alkyl and C$_{1-10}$ alkyl substituted with phenyl;

Q is selected independently from the group consisting of C$_{1-10}$ alkoxy, C$_{1-10}$ alkyl-S—, C$_{1-10}$ alkoxy substituted with phenyl, and C$_{1-10}$ alkyl-S-substituted with phenyl;

G is selected from the group consisting of cyano, amidino (—C(=NH)NH$_2$), guanidino (—NHC(=NH)NH$_2$), isothiureido (—S—C(=NH)NH$_2$), amino, C$_{1-6}$ alkylamino, C$_{2-12}$ dialkylamino, and imidazyl;

R$_3$ is selected independently from the group consisting of H, R$_6$, halogen, CN, CO—C$_6$H$_5$, benzoyl substituted with K on the phenyl, CO$_2$H, CO$_2$R$_7$, CONHR$_8$, CONR$_8$R$_9$, CO-AA$_4$-T, R$_4$ is selected from the group consisting of R$_6$, halogen, CN, CO—C$_6$H$_5$, benzoyl substituted with K on the phenyl, CO$_2$H, CO$_2$R$_7$, CONHR$_8$, CONR$_8$R$_9$, CO-AA$_4$-T,

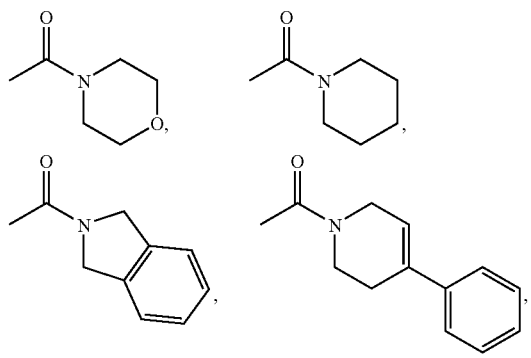

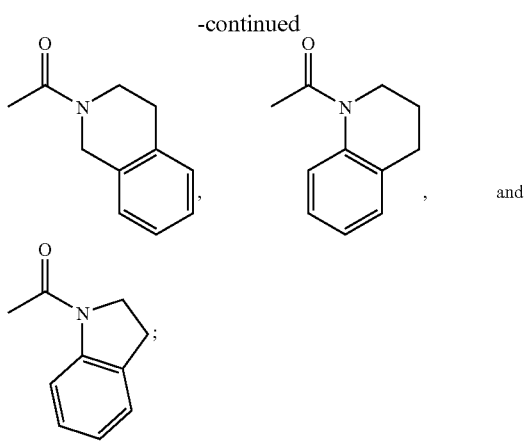

$R_6$ is selected independently from the group consisting of phenyl, phenyl monosubstituted with K, phenyl disubstituted with K, phenyl trisubstituted with K, naphthyl, naphthyl monosubstituted with K, naphthyl disubstituted with K, naphthyl trisubstituted with K, $C_{1-10}$ alkenyl, $C_{3-15}$ cyclized alkyl, $C_{1-10}$ alkyl with a phenyl group attached to the $C_{1-10}$ alkyl, $C_{3-15}$ cyclized alkyl with an attached phenyl group, $C_{1-10}$ alkyl with an attached phenyl group monosubstituted with K, $C_{1-10}$ alkyl with an attached phenyl group disubstituted with K, $C_{1-10}$ alkyl with an attached phenyl group trisubstituted with K, $C_{3-15}$ cyclized alkyl with an attached phenyl group substituted with K, $C_{1-10}$ alkyl with a naphthyl group attached to the $C_{1-10}$ alkyl, $C_{3-15}$ cyclized alkyl with an attached naphthyl group, $C_{1-10}$ alkyl with an attached naphthyl group monosubstituted with K, $C_{1-10}$ alkyl with an attached naphthyl group disubstituted with K, $C_{1-10}$ alkyl with an attached naphthyl group trisubstituted with K, $C_{3-15}$ cyclized alkyl with an attached naphthyl group substituted with K, $C_{1-10}$ alkyl with an attached 2-furyl group, $C_{1-10}$ alkyl with an attached 3-furyl group, $C_{1-10}$ alkyl with an attached 2-pyridyl group, $C_{1-10}$ alkyl with an attached 3-pyridyl group, $C_{1-10}$ alkyl with an attached 4-pyridyl group, 2-furyl, 3-furyl, 2-pyridyl, 3-pyridyl, and 4-pyridyl;

$R_7$ is selected independently from the group consisting of phenyl, phenyl monosubstituted with K, phenyl disubstituted with K, phenyl trisubstituted with K, naphthyl, naphthyl monosubstituted with K, naphthyl disubstituted with K, naphthyl trisubstituted with K, $C_{1-10}$ alkyl, $C_{1-10}$ alkenyl, $C_{3-15}$ cyclized alkyl, $C_{1-10}$ alkyl with a phenyl group attached to the $C_{1-10}$ alkyl, $C_{3-15}$ cyclized alkyl with an attached phenyl group, $C_{1-10}$ alkyl with an attached phenyl group substituted with K, $C_{1-10}$ alkyl with an attached phenyl group disubstituted with K, $C_{1-10}$ alkyl with an attached phenyl group trisubstituted with K, $C_{3-15}$ cyclized alkyl with an attached phenyl group monosubstituted with K, $C_{3-15}$ cyclized alkyl with an attached phenyl group disubstituted with K, $C_{3-15}$ cyclized alkyl with an attached phenyl group trisubstituted with K, $C_{1-10}$ alkyl with a naphthyl group attached to the $C_{1-10}$ alkyl, $C_{3-15}$ cyclized alkyl with an attached naphthyl group, $C_{1-10}$ alkyl with an attached naphthyl group monosubstituted with K, $C_{1-10}$ alkyl with an attached naphthyl group disubstituted with K, $C_{1-10}$ alkyl with an attached naphthyl group trisubstituted with K, $C_{3-15}$ cyclized alkyl with an attached naphthyl group monosubstituted with K, $C_{3-15}$ cyclized alkyl with an attached naphthyl group disubstituted with K, $C_{3-15}$ cyclized alkyl with an attached naphthyl group trisubstituted with K, $C_{1-10}$ alkyl with an attached 2-furyl group, $C_{1-10}$ alkyl with an attached 3-furyl group, $C_{1-10}$ alkyl with an attached 2-pyridyl group, $C_{1-10}$ alkyl with an attached 3-pyridyl group, and $C_{1-10}$ alkyl with an attached 4-pyridyl group;

T is selected independently from the group consisting of OH, $OR_{10}$, $NHR_{11}$, and $NR_{10}R_{11}$;

$AA_4$ is a side chain blocked or unblocked amino acid with the L configuration, D configuration, or no chirality at the alpha-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutanoic acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—$CH(CH_2CHEt_2)$-$CO_2H$, alpha-aminoheptanoic acid, $NH_2$—$CH(CH_2$-1-naphthyl)-$CO_2H$, $NH_2$—$CH(CH_2$-2-naphthyl)-$CO_2H$, $NH_2$—$CH(CH_2CH_2CH_2$-phenyl)-$CO_2H$, $NH_2$—$CH(CH_2$-cyclohexyl)-$CO_2H$, $NH_2$—$CH(CH_2$-cyclopentyl)-$CO_2H$, $NH_2$—$CH(CH_2$-cyclobutyl)-$CO_2H$, $NH_2$—$CH(CH_2$-cyclopropyl)-$CO_2H$, trifluoroleucine, 4-fluorophenylalanine, lysine substituted on the epsilon nitrogen with a biotinyl group, hexafluoroleucine, and

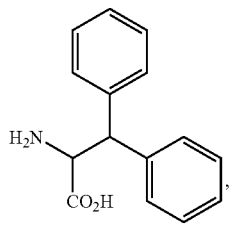

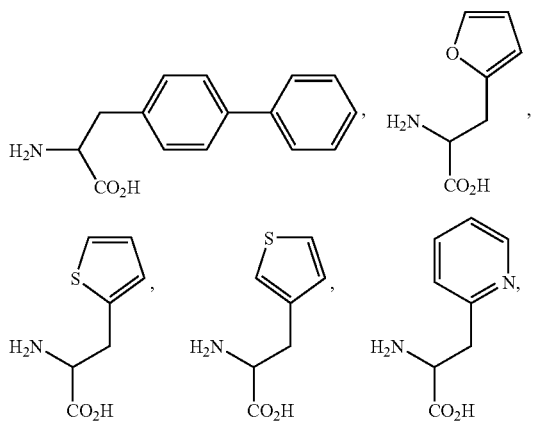

-continued

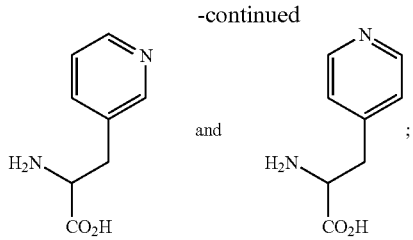

and $R_8$ and $R_9$ are selected independently from the group consisting of H, $C_{1-10}$ alkyl, $C_{1-10}$ alkenyl, $C_{3-20}$ cyclized alkyl, $C_{1-10}$ alkyl with a phenyl group attached to the $C_{1-10}$ alkyl, $C_{1-10}$ alkyl with two phenyl groups attached to the $C_{1-10}$ alkyl, $C_{3-20}$ cyclized alkyl with an attached phenyl group, phenyl, phenyl substituted with K, $C_{1-10}$ alkyl with an attached phenyl group substituted with K, $C_{1-10}$ alkyl with an attached phenyl group disubstituted with K, $C_{1-10}$ alkyl with an attached phenyl group trisubstituted with K, $C_{1-10}$ alkyl with two phenyl groups attached to the $C_{1-10}$ alkyl and substituted with K on the phenyl group, $C_{1-10}$ alkyl with two phenyl groups attached to the $C_{1-10}$ alkyl and disubstituted with K on the phenyl groups, $C_{3-20}$ cyclized alkyl with an attached phenyl group substituted with K, $C_{1-10}$ alkyl with a morpholine [—N(CH$_2$CH$_2$)O] ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl, $C_{1-20}$ alkyl with an OH group attached to the alkyl, —CH$_2$CH$_2$CH$_2$OCH$_3$, $C_{1-10}$ alkyl substituted by 1-naphthyl, $C_{1-10}$ alkyl substituted by 2-naphthyl, $C_{1-10}$ alkyl with an attached cyclohexyl group, —NH—CH$_2$CH$_2$-(4-hydroxyphenyl), —NH—CH$_2$CH$_2$-(3-indolyl), $C_{1-10}$ alkyl with an attached 2-furyl group, $C_{1-10}$ alkyl with an attached 3-furyl group, $C_{1-10}$ alkyl with an attached 2-pyridyl group, $C_{1-10}$ alkyl with an attached 3-pyridyl group, $C_{1-10}$ alkyl with an attached 4-pyridyl group, and $C_{1-5}$ alkyl with an attached phenyl and a hydroxyl attached to the $C_{1-5}$ alkyl;

$R_{10}$ and $R_{11}$ are selected independently from the group consisting of H, $C_{1-10}$ alkyl, phenyl, nitrophenyl, and $C_{1-10}$ alkyl substituted with phenyl;

or a pharmaceutically acceptable salt, pharmaceutically derivative, hydrate or solvate thereof.

2. A compound according to claim 1 wherein:
W is selected from the group consisting of hydrogen and halogen.

3. A compound according to claim 2 wherein:
$AA_1$, $AA_2$, and $AA_3$ are side chain blocked or unblocked amino acids with the L configuration, D configuration, or no chirality at the alpha-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutanoic acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, NH$_2$—CH(CH$_2$CHEt$_2$)-CO$_2$H, alpha-aminoheptanoic acid, NH$_2$—CH(CH$_2$-1-naphthyl)-CO$_2$H, NH$_2$—CH(CH$_2$-2-naphthyl)-CO$_2$H, NH$_2$—CH(CH$_2$CH$_2$CH$_2$-phenyl)-CO$_2$H, NH$_2$—CH(CH$_2$-cyclohexyl)-CO$_2$H, NH$_2$—CH(CH$_2$-cyclopentyl)-CO$_2$H, NH$_2$—CH(CH$_2$-cyclobutyl)-CO$_2$H, NH$_2$—CH(CH$_2$-cyclopropyl)-CO$_2$H, trifluoroleucine, 4-fluorophenylalanine, lysine substituted on the epsilon nitrogen with a biotinyl group, hexafluoroleucine;

$R_2$ is selected from the group consisting of $C_{1-10}$ alkyl, $C_{1-10}$ perfluoroalkyl, $C_{1-10}$ alkyl substituted with Q, $C_{1-10}$ alkyl substituted with phenyl, $C_{1-10}$ alkyl with an attached phenyl substituted with K, $C_{1-10}$ alkyl substituted with naphthyl, $C_{1-10}$ alkyl with an attached naphthyl substituted with K, phenyl, phenyl substituted with K, naphthyl, naphthyl substituted with K, $C_{1-10}$ alkyl substituted with CONH$_2$, $C_{1-10}$ alkyl substituted with CONHR$_5$, $C_{1-10}$ alkyl substituted with CO$_2$H, $C_{1-10}$ alkyl substituted with SO$_2$NH$_2$, $C_{1-10}$ alkyl substituted with SO$_3$H, $C_{1-10}$ alkyl substituted with CO$_2$R$_5$, CH$_2$CH$_2$SCH$_3$, CH$_2$-3-indolyl, $C_{1-2}$ alkyl with an attached 2-furyl, $C_{1-2}$ alkyl with an attached 3-furyl, $C_{1-2}$ alkyl with an attached 2-thienyl, $C_{1-2}$ alkyl with an attached 3-thienyl, $C_{1-2}$ alkyl with an attached 2-furyl substituted with K, $C_{1-2}$ alkyl with an attached 3-furyl substituted with K, $C_{1-2}$ alkyl with an attached 2-thienyl substituted with K, $C_{1-2}$ alkyl with an attached 3-thienyl substituted with K, $C_{1-2}$ alkyl with an attached 2-furyl substituted with G, $C_{1-2}$ alkyl with an attached 3-furyl substituted with G, $C_{1-2}$ alkyl with an attached 2-thienyl substituted with G, $C_{1-2}$ alkyl with an attached 3-thienyl substituted with G, CH$_2$-2-imidazyl, $C_{1-10}$ alkyl substituted with G, $C_{1-10}$ alkyl with an attached phenyl substituted with G, $C_{1-10}$ alkyl with an attached naphthyl substituted with G, phenyl substituted with G, and naphthyl substituted with G;

$AA_4$ is a side chain blocked or unblocked amino acid with the L configuration, D configuration, or no chirality at the alpha-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutanoic acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, NH$_2$—CH(CH$_2$CHEt$_2$)-CO$_2$H, alpha-aminoheptanoic acid, NH$_2$—CH(CH$_2$-1-naphthyl)-CO$_2$H, NH$_2$—CH (CH$_2$-2-naphthyl)-CO$_2$H, NH$_2$—CH(CH$_2$CH$_2$CH$_2$-phenyl)-CO$_2$H, NH$_2$—CH(CH$_2$-cyclohexyl)-CO$_2$H, NH$_2$—CH(CH$_2$-cyclopentyl)-CO$_2$H, NH$_2$—CH(CH$_2$-cyclobutyl)-CO$_2$H, NH$_2$—CH(CH$_2$-cyclopropyl)-CO$_2$H, trifluoroleucine, 4-fluorophenylalanine, lysine substituted on the epsilon nitrogen with a biotinyl group, hexafluoroleucine.

4. A compound according to claim 1 wherein:
W is selected from the group consisting of hydrogen and halogen;
$R_2$ is selected from the group consisting of $C_{1-10}$ alkyl, $C_{1-10}$ perfluoroalkyl, $C_{1-10}$ alkyl substituted with Q, $C_{1-10}$ alkyl substituted with phenyl, $C_{1-10}$ alkyl with an attached phenyl substituted with K, $C_{1-10}$ alkyl substituted with naphthyl, $C_{1-10}$ alkyl with an attached naphthyl substituted with K, phenyl, phenyl substituted with K, naphthyl, naphthyl substituted with K, $C_{1-10}$ alkyl substituted with CONH$_2$, C$_{1-10}$ alkyl substituted with CONHR$_5$, C$_{1-10}$ alkyl substituted with CO$_2$H, C$_{1-10}$ alkyl substituted with SO$_2$NH$_2$, C$_{1-10}$ alkyl substituted with SO$_3$H, 2-furyl substituted with G, 3-furyl substituted with G, 2-thienyl substituted with G, 3-thienyl substituted with G, C$_{1-10}$ alkyl substituted with CO$_2$R$_5$, CH$_2$CH$_2$SCH$_3$, CH$_2$-3-indolyl, C$_{1-2}$ alkyl with an attached 2-furyl substituted with K, C$_{1-2}$ alkyl with an attached 3-furyl substituted with K, C$_{1-2}$ alkyl with an attached 2-thienyl substituted with K, C$_{1-2}$ alkyl with an attached 3-thienyl substituted with K, C$_{1-2}$ alkyl with an attached 2-furyl substituted with G, C$_{1-2}$ alkyl with an attached 3-furyl substituted with G, C$_{1-2}$ alkyl with an attached 2-thienyl substituted with G, C$_{1-2}$ alkyl with an attached 3-thienyl substituted with G, CH$_2$-2-imidazyl, C$_{1-10}$ alkyl substituted with G, C$_{1-10}$ alkyl with an attached phenyl substituted with G, C$_{1-10}$ alkyl with an attached naphthyl substituted with G, phenyl substituted with G, and naphthyl substituted with G.

5. A compound according to claim 4 wherein:

AA$_1$, AA$_2$, and AA$_3$ are side chain blocked or unblocked amino acids with the L configuration, D configuration, or no chirality at the alpha-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutanoic acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, NH$_2$—CH(CH$_2$CHEt$_2$)-CO$_2$H, alpha-aminoheptanoic acid, NH$_2$—CH(CH$_2$-1-naphthyl)-CO$_2$H, NH$_2$—CH(CH$_2$-2-naphthyl)-CO$_2$H, NH$_2$—CH(CH$_2$CH$_2$CH$_2$-phenyl)-CO$_2$H, NH$_2$—CH(CH$_2$-cyclohexyl)-CO$_2$H, NH$_2$—CH(CH$_2$-cyclopentyl)-CO$_2$H, NH$_2$—CH(CH$_2$-cyclobutyl)-CO$_2$H, NH$_2$—CH(CH$_2$-cyclopropyl)-CO$_2$H, trifluoroleucine, 4-fluorophenylalanine, lysine substituted on the epsilon nitrogen with a biotinyl group, hexafluoroleucine;

AA$_4$ is a side chain blocked or unblocked amino acid with the L configuration, D configuration, or no chirality at the alpha-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutanoic acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, NH$_2$—CH(CH$_2$CHEt$_2$)-CO$_2$H, alpha-aminoheptanoic acid, NH$_2$—CH(CH$_2$-1-naphthyl)-CO$_2$H, NH$_2$—CH(CH$_2$-2-naphthyl)-CO$_2$H, NH$_2$—CH(CH$_2$CH$_2$CH$_2$-phenyl)-CO$_2$H, NH$_2$—CH(CH$_2$-cyclohexyl)-CO$_2$H, NH$_2$—CH(CH$_2$-cyclopentyl)-CO$_2$H, NH$_2$—CH(CH$_2$-cyclobutyl)-CO$_2$H, NH$_2$—CH(CH$_2$-cyclopropyl)-CO$_2$H, trifluoroleucine, 4-fluorophenylalanine, lysine substituted on the epsilon nitrogen with a biotinyl group, hexafluoroleucine.

6. The compound of claim 1, wherein each of the double bond carbons stereochemistry selected from the group consisting of cis, trans, E, and Z.

7. The composition of claim 1, wherein said composition is substantially sterochemically pure at each of the double bonds.

8. The composition of claim 1, wherein said composition is a mixture of double bond isomers.

9. The composition of claim 1, wherein said composition substantially comprises a single optical isomer.

* * * * *

```
                       SEQUENCE LISTING

<160> NUMBER OF SEQ ID NOS: 4

<210> SEQ ID NO 1
<211> LENGTH: 5
<212> TYPE: PRT
<213> ORGANISM: artificial sequence
<220> FEATURE:
<223> OTHER INFORMATION: conserved active site of caspase
<220> FEATURE:
<221> NAME/KEY: misc_feature
<222> LOCATION: (4)..(4)
<223> OTHER INFORMATION: X=R, Q, G

<400> SEQUENCE: 1

Gln Ala Cys Xaa Gly
1               5

<210> SEQ ID NO 2
<211> LENGTH: 4
<212> TYPE: PRT
<213> ORGANISM: artificial sequence
<220> FEATURE:
<223> OTHER INFORMATION: group I caspase recognition site

<400> SEQUENCE: 2

Trp Glu His Asp
1

<210> SEQ ID NO 3
<211> LENGTH: 4
<212> TYPE: PRT
<213> ORGANISM: artificial sequence
<220> FEATURE:
<223> OTHER INFORMATION: group II caspase recognition site
<220> FEATURE:
<221> NAME/KEY: misc_feature
<222> LOCATION: (3)..(3)
<223> OTHER INFORMATION: Xaa can be any naturally occurring amino acid

<400> SEQUENCE: 3

Asp Glu Xaa Asp
1

<210> SEQ ID NO 4
<211> LENGTH: 4
<212> TYPE: PRT
<213> ORGANISM: artificial sequence
<220> FEATURE:
```

```
<223> OTHER INFORMATION: group III caspase recognition site
<220> FEATURE:
<221> NAME/KEY: misc_feature
<222> LOCATION: (1)..(1)
<223> OTHER INFORMATION: X=V or L
<220> FEATURE:
<221> NAME/KEY: misc_feature
<222> LOCATION: (3)..(3)
<223> OTHER INFORMATION: Xaa can be any naturally occurring amino acid

<400> SEQUENCE: 4

Xaa Glu Xaa Asp
1
```